US010240127B2

(12) United States Patent
Larocca et al.

(10) Patent No.: US 10,240,127 B2
(45) Date of Patent: Mar. 26, 2019

(54) EXOSOMES FROM CLONAL PROGENITOR CELLS

(71) Applicant: ReCyte Therapeutics, Inc., Alameda, CA (US)

(72) Inventors: Dana Larocca, Alameda, CA (US); Mohammad Hassanipour, Danville, CA (US); Paola A. Bignone, Alameda, CA (US)

(73) Assignee: ReCyte Therapeutics, Inc., Alameda, CA (US)

( * ) Notice: Subject to any disclaimer, the term of this patent is extended or adjusted under 35 U.S.C. 154(b) by 0 days.

(21) Appl. No.: 14/748,215

(22) Filed: Jun. 23, 2015

(65) Prior Publication Data

US 2016/0108368 A1 Apr. 21, 2016

Related U.S. Application Data

(60) Provisional application No. 62/020,869, filed on Jul. 3, 2014.

(51) Int. Cl.
*A61K 35/44* (2015.01)
*C12N 5/071* (2010.01)

(52) U.S. Cl.
CPC ............ *C12N 5/0692* (2013.01); *A61K 35/44* (2013.01); *C12N 2506/02* (2013.01); *C12N 2506/1353* (2013.01)

(58) Field of Classification Search
CPC ..... A61K 35/44; C12N 5/071; C12N 2506/02
USPC .... 424/193.1, 520, 450; 435/6.1, 6.12, 7.21, 435/7.23, 377, 91.1, 91.31, 17.1, 366, 435/455, 317.1; 536/23.1, 24.5; 514/44
See application file for complete search history.

(56) References Cited

U.S. PATENT DOCUMENTS

| | | | |
|---|---|---|---|
| 6,685,911 B1 | 2/2004 | Zitvogel et al. | |
| 7,625,573 B2 | 12/2009 | Zitvogel et al. | |
| 7,928,069 B2 | 4/2011 | Prestwich et al. | |
| 8,021,847 B2 | 9/2011 | Pietrzkowski | |
| 8,324,184 B2 | 12/2012 | Prestwich et al. | |
| 8,476,017 B2 | 7/2013 | Pietrzkowski | |
| 2005/0250727 A1* | 11/2005 | Tasken ................. | A61K 38/005 514/44 R |
| 2008/0070303 A1 | 3/2008 | West et al. | |
| 2010/0184033 A1 | 7/2010 | West et al. | |
| 2012/0093885 A1 | 4/2012 | Sahoo et al. | |
| 2014/0010801 A1 | 1/2014 | Niedernhofer et al. | |
| 2016/0002597 A1* | 1/2016 | Sinden ................... | A61K 35/30 424/93.7 |
| 2016/0193252 A1* | 7/2016 | Hicks .................... | A61K 35/30 424/450 |
| 2017/0108503 A1* | 4/2017 | Klass ................... | C12Q 1/6886 |
| 2017/0146529 A1* | 5/2017 | Nagrath ............ | G01N 33/54353 |

FOREIGN PATENT DOCUMENTS

| | | |
|---|---|---|
| EP | 1001806 B1 | 9/2004 |
| EP | 1523990 B1 | 9/2009 |
| EP | 2254586 B1 | 4/2015 |
| EP | 2496711 B1 | 2/2016 |
| WO | 1999/003499 A1 | 1/1999 |
| WO | 2003/076603 A2 | 9/2003 |
| WO | 2005/121369 A2 | 12/2005 |
| WO | 2009/105044 A1 | 8/2009 |
| WO | 2011/053257 A2 | 5/2011 |
| WO | 2012/020308 A2 | 2/2012 |
| WO | 2012/125471 A1 | 9/2012 |
| WO | 2013/003595 A1 | 1/2013 |
| WO | 2013/014691 A1 | 1/2013 |
| WO | 2013/150303 A1 | 10/2013 |
| WO | 2013/172793 A1 | 11/2013 |
| WO | 2014/013258 A1 | 1/2014 |
| WO | 2014/022852 A1 | 2/2014 |
| WO | 2014/028493 A2 | 2/2014 |
| WO | 2014/091373 A1 | 6/2014 |
| WO | 2014/125276 A1 | 8/2014 |
| WO | 2014/125277 A1 | 8/2014 |
| WO | 2015/052526 A1 | 4/2015 |
| WO | 2015/052527 A1 | 4/2015 |

OTHER PUBLICATIONS

Keller, et al, Immunol. Letters, vol. 107, pp. 102-108 (2006).*
Garcia, et al, PLOS One, vol. 10, No. 9, e0138849 (2015).*
Kucharzewska et al, PNAS, vol. 110, No. 18, pp. 7312-7317 (2013).*
Bian et al., "Extracellular vesicles derived from human bone marrow mesenchymal stem cells promote angiogenesis in a rat myocardial infarction model," *J Mol Med* DOI 10.1007/s00109-013-1110-5, 2013, pp. 1-11.
Bruno et al., "Mesenchymal Stem Cell-Derived Microvesicles Protect Against Acute Tubular Injury," *J Am Soc Nephrol* 20(5)1053-1067 (2009).
Camussi et al. "Exosomes/microvesicles as a mechanism of cell-to-cell communication" (2010) *Kidney International* 78:838.
Chen et al., "Enabling a robust scalable manufacturing process for therapeutic exosomes through oncogenic ," Journal of Translational Medicine 9:47 (2011).
Climent et al. "TGFβ Triggers miR-143/145 Transfer From Smooth Muscle Cells to Endothelial Cells, Thereby Modulating Vessel Stabilization" (2015) *Circ Res.* 116(11):1753.
Dai et al. "MicroRNA-223-3p Inhibits the Angiogenesis of Ischemic Cardiac Microvascular Endothelial Cells via Affecting RPS6KB1/hif-1a Signal Pathway" (2014) *Plos One* 9(10):e108468.
Deregibus et al. "Endothelial progenitor cell-derived microvesicles activate an angiogenic program in endothelial cells by a horizontal transfer of mRNA" (2007) *Blood* 110:2440.
Fish et al. "miR-126 Regulates Angiogenic Signaling and Vascular Integrity" (2008) *Dev. Cell* 15(2):272.
Forte et al. "MicroRNA-Mediated Transformation by the Kaposi's Sarcoma-Associated Herpesvirus Kaposin Locus" (2015) *J Virol* 89(4): 2333.
Garcia et al., "Glucose Starvation in Cardiomyocytes Enhances Exosome Secretion and Promotes Angiogenesis in Endothelial Cells," *PLOS One* 10(9): e0138849 (2015).

(Continued)

Primary Examiner — Jane J Zara
(74) Attorney, Agent, or Firm — McCarter & English, LLP; Jonathan M. Sparks; Wendy Thai

(57) ABSTRACT

The invention provides methods, compositions, uses and kits relating to exosomes isolated from progenitor cells.

20 Claims, 14 Drawing Sheets

(56) References Cited

OTHER PUBLICATIONS

George et al. "Isolation of Human Platelet Membrane Microparticles" (1982) *Blood* 60:834.

Guduric-Fuchs et al. "Selective extracellular vesicle-mediated export of an overlapping set of microRNAs from multiple cell types" (2012) *BMC Genomics* 13:357.

Haflidadottir et al. "Upregulation of miR-96 Enhances Cellular Proliferation of Prostate Cancer Cells through FOXO1" (2013) *Plos One* 8(8):e72400.

Herrera et al. "Human liver stem cell-derived microvesicles accelerate hepatic regeneration in hepatectomized rats" (2010) *J Cell Mol Med* 14:1605.

Ibrahim et al., "Exosomes as Critical Agents of Cardiac Regeneration Triggered by Cell Therapy," *Stem Cell Reports* 2: 606-619 (2014).

Jakob and Landmesser "Role of microRNAs in stem/progenitor cells and cardiovascular repair" (2012) *Cardiovasc. Res*. 93(4):614.

Jeong et al., "Nanovesicles engineered from ES cells for enhanced cell proliferation," *Biomaterials* 35:9302-9310 (2014).

Keller et al. "Exosomes: From biogenesis and secretion to biological function" (2006) *Immunol Lett*. 107(2):102.

Kim et al. "Extracellular Membrane Vesicles from Tumor Cells Promote Angiogenesis via Sphingomyelin" (2002) *Cancer Res*. 62:6312.

King et al. "Hypoxic enhancement of exosome release by breast cancer cells" (2012) *BMC Cancer* 12:421.

Kucharzewska et al., "Exosomes reflect the hypoxic status of glioma cells and mediate hypoxia-dependent activation of vascular cells during tumor development," PNAS 110(18):7312-7317 (2013).

Laine et al. "MicroRNAs miR-96, miR-124, and miR-199a regulate gene expression in human bone marrow-derived mesenchymal stem cells" (2012) *J Cell Biochem*. 113(8):2687.

Lee et al., "Exosomes Mediate the Cytoprotective Action of Mesenchymal Stromal Cells on Hypoxia-Induced Pulmonary Hypertension," *Circulation* 126(22):2601-2611 (2012).

Lin et al. "Unregulated miR-96 Induces Cell Proliferation in Human Breast Cancer by Downregulating Transcriptional Factor FOXO3a" (2010) *Plos One* 5(12):e15797.

Liu et al. "MiR-106b and MiR-15b Modulate Apoptosis and Angiogenesis in Myocardial Infarction" (2012) *Cell Physiol Biochem*. 29(5-6):851.

Lopatina et al., "Platelet-derived growth factor regulates the secretion of extracellular vesicles by adipose mesenchymal stem cells and enhances their angiogenic potential," *Cell Communication and Signaling* 12:26-10.1186 (2014).

Martinez et al. "Shed membrane microparticles from circulating and vascular cells in regulating vascular function" (2005) *Am J Physiol Health Cir Physiol* 288:H1004.

Nicoli et al. "microRNA-mediated integration of haemodynamics and VEGF signaling during angiogenesis" (2010) *Nature* 464(7292): 1196.

Ohshima et al. "Let-7 MicroRNA Family Is Selectively Secreted into the Extracellular Environment via Exosomes in a Metastatic Gastric Cancer Cell Line" (2010) *PloS One* 5(10):e13247.

Ong et al. "Cross Talk of Combined Gene and Cell Therapy in Ischemic Heart Disease. Role of Exosomal MicroRNA Transfer" (2014) *Circulation* 130 (11 Suppl 1):S60.

Panktraz et al. "MicroRNA-155 Exerts Cell-Specific Antiangiogenic but Proarteriogenic Effects During Adaptive Neovascularization" (2015) Circulation 131(18):1575.

Sahoo et al. "Exosomes From Human CD34 Stem Cells Mediate Their Proangiogenic Paracrine Activity" (2011) *Circ Res*. 109(7):724.

Semo et al. "The 106b~25 microRNA cluster is essential for neovascularization after hindlimb ischaemia in mice" (2014) *Eur Heart J*. 35(45):3212.

Spinetti et al. "MicroRNA-15a and MicroRNA-16 Impair Human Circulating Proangiogenic Cell Functions and Are Increased in the Proangiogenic Cells and Serum of Patients With Critical Limb Ischemia" (2013) Circ Res. 112(2):335.

Suarez and Sessa "MicroRNAs As Novel Regulators of Angiogenesis" (2009) *Circ Res*. 104(4):442.

Tadokoro et al. "Exosomes Derived from Hypoxic Leukemia Cells Enhance Tube Formation in Endothelial Cells" (2013) *J Biol Chem*. 288(48):34343.

Wagner et al. "Replicative Senescence of Mesenchymal Stem Cells: A Continuous and Organized Process" (2008) *Plos One* 3(5):e2213.

West et al., "The ACTCellerate initiative: large-scale combinatorial cloning of novel human embryonic stem cell derivatives," *Regen Med* 3(3):287-308 (2008).

Xin et al., "Systemic administration of exosomes released from mesenchymal stromal cells promote functional recovery and neurovascular plasticity after stroke in rats," *Journal of Cerebral Blood Flow & Metabolism* 33:1711-1715 (2013).

Zernecke, et al., "Delivery of MicroRNA-126 by Apoptotic Bodies Induces CXCL12-Dependent Vascular Protection," *Science Signaling* 2(100): ra81 (2009).

Zhang et al., "Microvesicles Derived from Human Umbilical Cord Mesenchymal Stem Cells Stimulated by Hypoxia Promote Angiogenesis Both In Vitro and In Vivo," *Stem Cells and Development* 21(18):3289-3297 (2012).

Zou et al. "Two Functional MicroRNA-126s Repress a Novel Target Gene p21-Activated Kinase 1 to Regulate Vascular Integrity in Zebrafish," *Circ. Res*. 108(2):201-209 (2011).

* cited by examiner

EXOSOMES FROM CLONAL PROGENITOR CELLS

CROSS-REFERENCE TO RELATED APPLICATIONS

This application claims priority to U.S. Provisional Application No. 62/020,869, filed on Jul. 3, 2014, the entire contents of which are hereby incorporated by reference.

FIELD OF THE INVENTION

The field of the invention relates to exosomes isolated from progenitor cells.

BACKGROUND

Exosomes are believed to contain important signaling molecules that may provide the source of trophic factors responsible for some regenerative benefits seen in cell replacement therapy. As such they would provide an alternative to some cell based therapies that would be easier to manufacture on a large scale and potentially safer to administer to a subject in need of cell therapy. In particular, the risk associated with transmission of infectious agents such as viruses may be lower compared to transplanting whole cells. Moreover, the risk of immune rejection of the exosomes relative to transplanted cells may also be lower. Accordingly, exosomes may provide an attractive alternative or adjunct to cell based therapies and cell based regenerative medicine.

Exosomes are 30 to 120 nm vesicles secreted by a wide range of mammalian cell types. Keller et al. (2006) *Immunol Lett.* 107(2):102; Camussi et al. (2010) *Kidney International* 78:838. The vesicles are enclosed by a lipid bilayer and are larger than LDL which has a size of 22 nm, but smaller than a red blood cell, which is 6000 to 8000 nm in diameter and has a thickness of 2000 nm Keller et al. (2006) *Immunol Lett.* 107(2):102.

Exosomes are found both in cells growing in vitro as well as in vivo. They can be isolated from tissue culture media as well as bodily fluids such as plasma, urine, milk and cerebrospinal fluid. George et al. (1982) *Blood* 60:834; Martinez et al. (2005) *Am J Physiol Health Cir Physiol* 288:H1004. Exosomes originate from the endosomal membrane compartment. They are stored in intraluminal vesicles within multivesicular bodies of the late endosome. Multivesicular bodies are derived from the early endosome compartment and contain within them smaller vesicular bodies that include exosomes. Exosomes are released from the cell when multivesicular bodies fuse with the plasma membrane. Methods of isolating exosomes from cells has been described, see e.g. US Patent Application Publication No. 20120093885

Exosomes contain a variety of molecules including proteins, lipids and nucleic acids such as DNA, mRNA and miRNA. Their contents are believed to play a part in cell to cell communication involving the release of the exosome from one cell and the binding/fusion of the exosome with a second cell, wherein the contents of the exosomal compartment are released within the second cell.

It has been reported that exosomes derived from endothelial progenitor cells may act as vehicle for mRNA transport among cells. These exosomes were shown to incorporate into normal endothelial cells by interacting with the $\alpha 4\beta 1$ integrin. Once incorporated into the endothelial cells, the exosomes stimulated an angiogenic program. Deregibus et al. (2007) *Blood* 110:2440. Similar results were obtained in vivo using severe combined immunodeficient mice. Exosome stimulated endothelial cells implanted subcutaneously in Matrigel (a murine sarcoma extract) organized into a patent vessel network connected with the murine vasculature. Deregibus, supra. Bruno et al. (2009) *J Am Soc Nephrol* 20:1053; Herrera et al. (2010) *J Cell Mol Med* 14:1605.

Of the various molecular cargo of exosomes, miRNAs have recently attracted a lot of attention due to their regulatory roles in gene expression. MiRNAs are small, non-coding regulatory RNAs that can have a wide range of effects on multiple RNA targets, thus having the potential to have greater phenotypic influence than coding RNAs. MiRNA profiles of exosomes often differ from those of the parent cells. Profiling studies have demonstrated that miRNAs are not randomly incorporated into exosomes but rather a subset of miRNAs is preferentially packaged into exosomes, suggesting an active sorting mechanism of exosomal miRNAs. Guduric-Fuchs et al. (2014) *Nucleic Acid Res.* 42:9195; Ohshima et al. (2010) *PloS One* 5(10):e13247.

Because exosomes contain a variety of molecules, many believed to play an important role in cell signaling, exosomes would prove useful in research and industry and would have applications as therapeutics, diagnostics and in screening assays. Frequently, however, the availability of reproducible, essentially identical populations of exosomes is limited by the fact that most sources of exosomes are cells that senesce and thus have limited replicative capacity. Accordingly, there is a need for exosomes that are derived from a clonal source that has an extended replicative capacity that is greater than most adult or fetal derived cells. The invention described infra meets this need and as well as other needs in the field.

SUMMARY OF THE INVENTION

In various embodiments described herein the invention provides compositions comprising exosomes obtained from progenitor cell lines, as well as methods of making and using exosomes obtained from progenitor cell lines.

The isolation of embryonic progenitor cells has been described. See West et al. (2008) *Regen Med* 3:287; US Patent Application Publication Nos. 20080070303 20100184033. Embryonic progenitors are cell lines derived under a variety of culture conditions from pluripotent stem cells, such as human embryonic stem (hES) cells or induced pluripotent stem (iPS) cells. The progenitor cell lines are clonal and while they do, in most instances, senesce, they also possess longer telomeres compared to adult or fetal derived tissue or cells (such as adult stem cells) and accordingly have enhanced replicative capacity relative to those cell types. Because of their clonality and their enhanced replicative capacity they provide a suitable source of exosomes that will offer the benefit of uniformity with regard to the exosome composition and abundance relative to exosomes derived from their typical sources such as adult cells or adult stem cells.

In certain embodiments the invention provides an exosome isolated from a progenitor cell line, such as clonal progenitor cell line.

In certain embodiments the invention provides an exosome isolated from a human progenitor cell line, such as a clonal human progenitor cell line.

In some embodiments the invention provides an exosome isolated from endothelial progenitor cell.

In some embodiments the invention provides an exosome isolated from a clonal human endothelial progenitor cell.

In other embodiments the invention provides an exosome isolated from the 30-MV2-6 human clonal progenitor cell line.

In further embodiments the invention provides an exosome isolated from a human clonal progenitor cell that expresses CD31 and CD34.

In certain embodiments the invention provides an exosome isolated from a human progenitor cell line, wherein the human progenitor cell is not an adult stem cell.

In further embodiments the invention provides an exosome isolated from a human progenitor cell line, wherein the human progenitor cell is not a mesenchymal stem cell (MSC).

In certain embodiments the invention provides an exosome isolated from a cell that has not been transfected with an exogenous gene.

In certain other embodiments the invention provides an exosome isolated from a cell that has been transfected with an exogenous gene, wherein the gene is not c-myc.

In yet other embodiments the invention provides an exosome isolated from a cell that does not overexpress c-myc.

In other embodiments the invention provides an exosome isolated from the 30-MV2-6 clonal human progenitor cell line.

In still other embodiments the invention provides an exosome isolated from a cell expressing one or more genes chosen from the genes listed in Table 1.

In further embodiments the invention provides an exosome isolated from a cell expressing a plurality of the genes chosen from the genes listed in Table 1.

In yet other embodiments the invention provides an exosome isolated from a cell expressing the genes listed in Table 1.

In some embodiments, the invention provides an exosome containing CD63.

In other embodiments, the invention provides an exosome containing one or more miRNAs listed in Table 2 or Table 4.

In further embodiments, the invention provides an exosome containing one or more angiogenic miRNAs.

In yet further embodiments, the invention provides an exosome containing miR-126.

In some embodiments the invention provides an exosome isolated from a human clonal progenitor cell, wherein the exosome contains one or more miRNAs listed in Table 2 or Table 4.

In other embodiments the invention provides an exosome isolated from a human clonal progenitor cell, wherein the exosome contains one or more angiogenic miRNAs.

In yet other embodiments the invention provides an exosome isolated from a human clonal progenitor cell, wherein the exosome contains miR-126.

In further embodiments the invention provides an exosome isolated from a human clonal progenitor cell, wherein the exosome contains CD63.

In some embodiments the invention provides an exosome that induces a cell to form vascular tube like structures.

In other embodiments the invention provides an exosome that induces a cell to form branching vascular tube like structures.

In yet other embodiments the invention provides a cell culture comprising an exosome isolated from a progenitor cell and a cell which was not the source of the isolated exosome.

In certain embodiments the invention provides a cell culture comprising an exosome isolated from a progenitor cell and a cell which was not the source of the isolated exosome, wherein the cell has the ability to form vascular tube like structures.

In further embodiments the invention provides a cell culture comprising an exosome isolated from a progenitor cell and a cell which was not the source of the isolated exosome, wherein the cell is an endothelial cell.

In still further embodiments the invention provides a cell culture comprising an exosome isolated from a progenitor cell and a cell which was not the source of the isolated exosome, wherein the cell is a human umbilical vein endothelial cell (HUVEC).

In the cell culture embodiments described above the progenitor cell may be a human progenitor cell, such as a human embryonic progenitor cell. One example of a human embryonic progenitor cell is the 30-MV2-6 cell line.

In the cell culture embodiments described above the progenitor cell may be, for example, a clonal progenitor cell line, an oligoprogenitor cell line. The progenitor cell may express one or more genes listed in Table 1. The progenitor cell may express a plurality of the genes listed in Table 1. The progenitor cell line may express the genes listed in Table 1. The progenitor cell line may express CD31 and CD34.

In some embodiments the invention provides a method of isolating an exosome from a progenitor cell, such as a clonal progenitor cell comprising 1) culturing the progenitor cell in a suitable media or buffer for a time sufficient to allow the cells to exocytose exosomes into the culture media; 2) harvesting the media from the cell culture of step 1; and 3) isolating the exosomes from the media of step 2, thereby isolating an exosome from a clonal progenitor cell.

In some embodiments the invention provides a method of isolating an exosome from a human clonal progenitor cell comprising 1) culturing the human clonal progenitor cell in a suitable media or buffer for a time sufficient to allow the human clonal progenitor cell to exocytose exosomes into the culture media; 2) harvesting the media from the cell culture of step 1; and 3) isolating the exosomes from the media of step 2, thereby isolating an exosome from a clonal progenitor cell.

In other embodiments the invention provides a method of isolating an exosome from a 30-MV2-6 human clonal progenitor cell line comprising 1) culturing the 30-MV2-6 human clonal progenitor cell line in a suitable media or buffer for a time sufficient to allow the 30-MV2-6 human clonal progenitor cell line to exocytose exosomes into the culture media; 2) harvesting the media from the cell culture of step 1; and 3) isolating the exosomes from the media of step 2, thereby isolating an exosome from a 30-MV2-6 human clonal progenitor cell line.

In still other embodiments the invention provides a method of isolating an exosome from a human clonal progenitor cell line expressing CD31 and CD34 comprising 1) culturing the human clonal progenitor cell line expressing CD31 and CD34 in a suitable media or buffer for a time sufficient to allow the human clonal progenitor cell line expressing CD31 and CD34 to exocytose exosomes into the culture media; 2) harvesting the media from the cell culture of step 1; and 3) isolating the exosomes from the media of step 2, thereby isolating an exosome from a human clonal progenitor cell line expressing CD31 and CD34.

In some embodiments the invention provides a method of isolating an exosome from a human clonal progenitor cell line expressing one or more of the genes listed in Table 1 comprising 1) culturing the human clonal progenitor cell line expressing one or more of the genes listed in Table 1 in a suitable media or buffer for a time sufficient to allow the human clonal progenitor cell line expressing one or more of the genes listed in Table 1 to exocytose exosomes into the culture media; 2) harvesting the media from the cell culture of step 1; and 3) isolating the exosomes from the media of step 2, thereby isolating an exosome from a human clonal progenitor cell line expressing one or more of the genes listed in Table 1.

In still other embodiments the invention provides a method of isolating an exosome from a human clonal progenitor cell line expressing a plurality of the genes listed in Table 1 comprising 1) culturing the human clonal progenitor cell line expressing a plurality of the genes listed in Table 1 in a suitable media or buffer for a time sufficient to allow the human clonal progenitor cell line expressing a plurality of the genes listed in Table 1 to exocytose exosomes into the culture media; 2) harvesting the media from the cell culture of step 1; and 3) isolating the exosomes from the media of step 2, thereby isolating an exosome from a human clonal progenitor cell line expressing a plurality of the genes listed in Table 1.

In further embodiments the invention provides a method of isolating an exosome from a human clonal progenitor cell line expressing the genes listed in Table 1 comprising 1) culturing the human clonal progenitor cell line expressing the genes listed in Table 1 in a suitable media or buffer for a time sufficient to allow the human clonal progenitor cell line expressing the genes listed in Table 1 to exocytose exosomes into the culture media; 2) harvesting the media from the cell culture of step 1; and 3) isolating the exosomes from the media of step 2, thereby isolating an exosome from a human clonal progenitor cell line expressing the genes listed in Table 1.

In some embodiments the invention provides a method of isolating an exosome from a human clonal progenitor cell wherein the human clonal progenitor cell line has not been transfected with an exogenous gene comprising 1) culturing the human clonal progenitor cell line that has not been transfected with an exogenous gene in a suitable media or buffer for a time sufficient to allow the human clonal progenitor cell line that has not been transfected with an exogenous gene to exocytose exosomes into the culture media; 2) harvesting the media from the cell culture of step 1; and 3) isolating the exosomes from the media of step 2, thereby isolating an exosome from a human clonal progenitor cell line that has not been transfected with an exogenous gene.

In other embodiments the invention provides a method of isolating an exosome from a human clonal progenitor cell, wherein the human clonal progenitor cell line has been transfected with an exogenous gene, wherein the gene is not c-myc, comprising 1) culturing the human clonal progenitor cell line that has been transfected with an exogenous gene, wherein the exogenous gene is not c-myc, in a suitable media or buffer for a time sufficient to allow the human clonal progenitor cell line that has been transfected with an exogenous gene, wherein the exogenous gene is not c-myc, to exocytose exosomes into the culture media; 2) harvesting the media from the cell culture of step 1; and 3) isolating the exosomes from the media of step 2, thereby isolating an exosome from a human clonal progenitor cell line that has been transfected with an exogenous gene, wherein the exogenous gene is not c-myc.

In still other embodiments the invention provides a method of isolating an exosome from a human clonal progenitor cell wherein the human clonal progenitor cell line does not overexpress c-myc comprising 1) culturing the human clonal progenitor cell line that does not overexpress c-myc in a suitable media or buffer for a time sufficient to allow the human clonal progenitor cell line that has not been transfected with an exogenous gene to exocytose exosomes into the culture media; 2) harvesting the media from the cell culture of step 1; and 3) isolating the exosomes from the media of step 2, thereby isolating an exosome from a human clonal progenitor cell line that does not overexpress c-myc.

In further embodiments the invention provides a method of inducing or enhancing a cells ability to form vascular tube like structures comprising contacting a cell capable of making vascular tube like structures with an exosome isolated from a progenitor cell thereby inducing or enhancing a cells ability to form vascular tube like structures.

In still further embodiments the invention provides a method of inducing or enhancing a cells ability to form vascular tube like structures comprising contacting an endothelial cell with an exosome isolated from a progenitor cell thereby inducing or enhancing an endothelial cells ability to form vascular tube like structures.

In other embodiments the invention provides a method of inducing or enhancing a cells ability to form vascular tube like structures comprising contacting a cell capable of making vascular tube like structures with an exosome isolated from a clonal progenitor cell thereby inducing or enhancing a cells ability to form vascular tube like structures.

In further embodiments the invention provides a method of inducing or enhancing a cells ability to form vascular tube like structures comprising contacting a cell capable of making vascular tube like structures with an exosome isolated from a human clonal progenitor cell thereby inducing or enhancing a cells ability to form vascular tube like structures.

In certain embodiments the invention provides a method of inducing or enhancing a cells ability to form vascular tube like structures comprising contacting a cell capable of making vascular tube like structures with an exosome isolated from a human endothelial progenitor cell thereby inducing or enhancing a cells ability to form vascular tube like structures.

In yet other embodiments the invention provides a method of inducing or enhancing a cells ability to form vascular tube like structures comprising contacting a cell capable of making vascular tube like structures with an exosome isolated from a human clonal endothelial progenitor cell thereby inducing or enhancing a cells ability to form vascular tube like structures.

In further embodiments the invention provides a method of inducing or enhancing a cells ability to form vascular tube like structures comprising contacting a cell capable of making vascular tube like structures with an exosome isolated from a cell expressing one or more genes listed in Table 1 thereby inducing or enhancing a cells ability to form vascular tube like structures.

In other embodiments the invention provides a method of inducing or enhancing a cells ability to form vascular tube like structures comprising contacting a cell capable of making vascular tube like structures with an exosome isolated from a cell expressing a plurality of genes listed in Table 1 thereby inducing or enhancing a cells ability to form vascular tube like structures.

In yet other embodiments the invention provides a method of inducing or enhancing a cells ability to form vascular tube like structures comprising contacting a cell capable of making vascular tube like structures with an exosome isolated from a cell expressing the genes listed in Table 1 thereby inducing or enhancing a cells ability to form vascular tube like structures.

In still other embodiments the invention provides a method of inducing or enhancing a cells ability to form vascular tube like structures comprising contacting a cell capable of making vascular tube like structures with an exosome isolated from a cell expressing the markers CD31 and CD34 thereby inducing or enhancing a cells ability to form vascular tube like structures.

In further embodiments the invention provides a method of inducing or enhancing a cells ability to form vascular tube like structures comprising contacting a cell capable of making vascular tube like structures with an exosome isolated from a 30-MV2-6 cell thereby inducing or enhancing a cells ability to form vascular tube like structures.

In still other embodiments the invention provides a method of regeneration a tissue or an organ comprising contacting one or more cells capable of regenerating a tissue or an organ with an exosome isolated from a progenitor cell.

In yet other embodiments the invention provides a method of regenerating a vascular tissue or organ comprising contacting a cell capable of regenerating a vascular tissue or organ with an exosome isolated from a progenitor cell.

In some embodiments the invention provides a method of regenerating a vascular tissue or organ comprising contacting a cell capable of regenerating a vascular tissue or organ with an exosome isolated from a human clonal endothelial progenitor cell.

In further embodiments the invention provides a method of regenerating a vascular tissue or organ comprising contacting a cell capable of regenerating a vascular tissue or organ with an exosome isolated from a 30-MV2-6 cell.

In certain embodiments the invention provides a method of treating a subject in need of vascular therapy comprising administering an exosome isolated from a progenitor cell.

In some embodiments the invention provides a method of treating a subject in need of vascular therapy comprising administering an exosome isolated from a human clonal progenitor cell.

In further embodiments the invention provides a method of treating a subject in need of vascular therapy comprising administering an exosome isolated from an endothelial progenitor cell.

In certain embodiments the invention provides a method of treating a subject in need of vascular therapy comprising administering an exosome isolated from human clonal endothelial progenitor cell.

In yet other embodiments the invention provides a method of treating a subject in need of vascular therapy comprising administering an exosome isolated from a 30-MV2-6 human endothelial progenitor cell.

In still other embodiments the invention provides a method of treating a subject in need of vascular therapy comprising administering an exosome isolated from a human clonal progenitor cell expressing CD31 and CD34.

In further embodiments the invention provides a method of treating a subject in need of vascular therapy comprising administering an exosome isolated from a human clonal progenitor cell expressing one or more genes listed in Table 1.

In some embodiments the invention provides a method of treating a subject in need of vascular therapy comprising administering an exosome isolated from a human clonal progenitor cell expressing a plurality of genes listed in Table 1.

In yet other embodiments the invention provides a method of treating a subject in need of vascular therapy comprising administering an exosome isolated from a human clonal progenitor cell expressing the markers listed in Table 1.

In further embodiments the invention provides a kit comprising an exosome isolated from a progenitor cell and at least one container.

BRIEF DESCRIPTION OF DRAWINGS

For a fuller understanding of the nature and advantages of the present invention, reference should be had to the following detailed description taken in connection with the accompanying drawings, in which.

DETAILED DESCRIPTION

Figure 1:
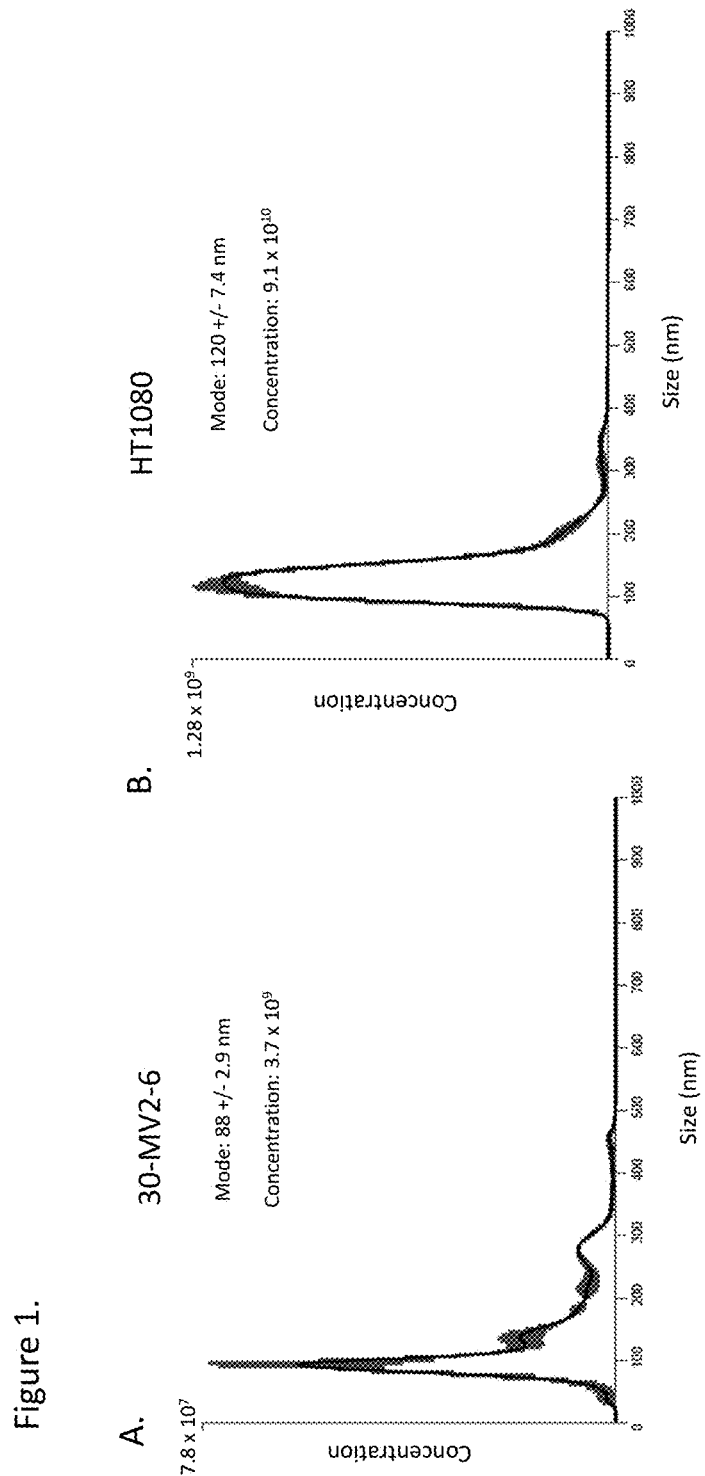
FIG. 1 shows a graph of the size and concentration of exosomes isolated from a) human embryonic progenitor cell line 30-MV2-6; and b) the HT1080 cell line.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Any methods and materials similar or equivalent to those described herein can be used in the practice or testing of embodiments of the present disclosure.

The invention provides exosomes isolated from clonal progenitor cells, such as human clonal progenitor cells derived from a human pluripotent stem cell. Because the cells are clonal and have enhanced replicative capacity in vitro, the invention provides a means of producing the same exosomes over and over again. This provides for a consistent product allowing either the researcher or clinician to alleviate any concerns regarding both the quality and the consistency of the exosomes in any application. Accordingly, the invention also provides methods of making the progenitor cells from which the exosomes are derived and methods of isolating the exosomes from these cells. The invention also contemplates uses, cell cultures and kits comprising the exosomes all of which are described infra.

Definitions

As used herein, the singular forms "a," "an," and "the" include plural reference unless the context clearly dictates otherwise. Thus, for example, reference to a "therapeutic" is a reference to one or more therapeutics and equivalents thereof known to those skilled in the art, and so forth.

As used herein, the term "about" means plus or minus 10% of the numerical value of the number with which it is being used. Therefore, about 50% means in the range of 45% to 55%.

"CD31", also known as PECAM-1 (platelet endothelial cell adhesion molecule) is a protein in the immunoglobulin superfamily found on the surface of platelets, monocytes, neutrophils, and some types of T-cells. CD31 makes up a large portion of endothelial cell intercellular junctions.

CD31 is encoded in humans by the PECAM-1 gene and is commonly used as a marker for endothelial cells.

"CD34" is a cell surface glycoprotein that functions as a cell-cell adhesion factor. The CD34 protein is a member of a family of single-pass transmembrane sialomucin proteins that are expressed on early hematopoietic and vascular-associated tissue. CD34 is encoded in humans by the CD34 gene. It is commonly used as a marker for hematopoietic and/or vascular endothelial cells.

As used herein, the term "clonal" refers to a population of cells obtained by the expansion of a single cell into a population of cells all derived from that original single cell and not containing other cells. The terms "clonal progenitor cell", "embryonic clonal progenitor cell", "clonal progenitor cell line" and "embryonic clonal progenitor cell line" each refer to progenitor cell lines that are derived clonally, i.e., derived by the expansion of a single cell into a population of cells all derived from that original single cell and not containing other cells.

The term "embryonic stem cell" as used herein refers to a pluripotent cell that is derived from a blastocysts, such as an in vitro fertilized blastocyst. Embryonic stem cells include human embryonic stem cells, which are available as established cell lines. The established cell lines are available commercially from numerous public cell banks, e.g. WiCell and private corporations, e.g. ESI BIO.

The term "human pluripotent cell" or "human pluripotent stem cell" as used herein refers to a human cell which is capable of differentiating into at least one cell type found in or derived from each of the three primary germ layers. Some human pluripotent stem cells have the ability to differentiate into all cells found in or derived from each of the three primary germ layers. Examples of human pluripotent stem cells include human embryonic stem cells (Thomson (1998) *Science* 282:1145), human embryonic germ cells (Shamblott et al. (2001) *PNAS* 98:113 and induced pluripotent cells (Takahashi et al. (2007) *Cell* 131:861.

The term "induced pluripotent stem cell" as used herein, refers to a pluripotent cell that has been genetically reprogrammed using any technique known in the art from an adult somatic cell back to the developmentally less mature pluripotent state.

The term "miRNA," as used herein, refers to microRNA which includes RNA species that are 21-25 nt long and may be single- or double-stranded. MicroRNAs are short, non-coding RNA molecules that have been found in animals, including humans, and in plants. The term encompasses small interfering RNA (siRNA) and small temporal RNA (stRNA), as well as miRNA proper. miRNAs are transcribed as parts of longer RNA molecules and processed in the nucleus by the dsRNA ribonuclease Drosha to hairpin structures 70-100 nucleotides long. These are transported to the cytoplasm where they are digested to 21-23-mers by the dsRNA ribonuclease Dicer. Single-stranded miRNAs bind to complementary sequences in mRNA thereby inhibiting translation.

"miR-126" is a human microRNA that is specifically expressed in endothelial cells, throughout capillaries and in larger blood vessels. miR-126 plays a role in angiogenesis by regulating the expression levels of various genes by pre- and post-transcription mechanisms. As used herein, the term "miR-126" refers to all of the following: the stem-loop miR-126, miR-126-3p (3' arm of the hairpin precursor) and miR-126-5p (5' arm of the hairpin precursor). miRNA naming conventions are described in Kozomara and Griffiths-Jones, (2014) *Nucleic Acids Res.* 42 (Database issue): D68. The terms "miR-126-3p" and "hsa-miR-126-3p" are also used interchangeably throughout this application.

The use of "nucleic acid," "polynucleotide" or "oligonucleotide" or equivalents herein means at least two nucleotides covalently linked together. In some embodiments, an oligonucleotide is an oligomer of 6, 8, 10, 12, 20, 30 or up to 100 nucleotides. In some embodiments, an oligonucleotide is an oligomer of at least 6, 8, 10, 12, 20, 30, 40, 50, 60, 70, 80, 90, 100, 150, 200, 300, 400, or 500 nucleotides. A "polynucleotide" or "oligonucleotide" may comprise DNA, RNA, cDNA, PNA or a polymer of nucleotides linked by phosphodiester and/or any alternate bonds.

The term "peptide," as used herein, refers to two or more amino acids joined by a peptide bond. A peptide can, in some instances, be a portion of a full length protein.

The term "protein" as used herein, refers to a full length protein, i.e. one having all of the amino acids coded for by the mRNA that encodes the particular protein. Also included in the definition are modified proteins where one or more amino acids have been cleaved (e.g. a signal sequence) as a result of the protein being secreted from a cell.

By "pharmaceutically acceptable", it is meant the carrier, diluent or excipient must be compatible with the other ingredients of the formulation and not deleterious to the recipient thereof.

The term "pluripotent cell" or "pluripotent stem cell" as used herein, refers to a cell which is capable of differentiating into at least one cell type found in or derived from each of the three primary germ layers. Some pluripotent stem cells have the ability to differentiate into all cells found in or derived from each of the three primary germ layers.

The term "progenitor cell line" as used herein refers to a line of cells that is more differentiated (developed) compared to a pluripotent cell, such as iPS cell or an hES cell, but is not terminally differentiated. Progenitor cells will have enhanced replicative capacity compared to a terminally differentiated cell which typically has senesced. Progenitor cells may also have longer telomere lengths compared to a cell that has terminally differentiated. Progenitor cell lines, when cultured, may be able double in population size at least 5, at least 10, at least 20, at least 30, at least 40, at least 50 times. In some instances progenitor cell lines may be able to double in population size 5-400 times, 10-300 times, 20-200 times, 30-80 times, 40-60 times. One example of a progenitor cell line is an embryonic progenitor cell. Embryonic progenitor cell is obtained from a pluripotent cell such as an iPS cell or a hES as previously described. See West et al. (2008) *Regen Med* 3:287; US Patent Application Publication Nos. 20080070303 20100184033.

The term "subject," as used herein includes, but is not limited to, humans, non-human primates and non-human vertebrates such as wild, domestic and farm animals including any mammal, such as cats, dogs, cows, sheep, pigs, horses, rabbits, rodents such as mice and rats. In some embodiments, the term "subject," refers to a male. In some embodiments, the term "subject," refers to a female.

The term "suitable media," as used herein, refers to a solution that can be used to grow cells in culture. A suitable media may include a formulation of salts and/or buffering reagents. A suitable media may include any or all of the following: salts, sugars, amino acids, proteins, growth factors, cytokines, and hormones, additives such as serum, albumin, antibiotics, insulin, selenium and transferrin. Suitable culture media includes for example commercially available culture media such as DMEM, MEM Stem Pro and the like.

A "therapeutically effective amount" of a composition such as a therapeutic agent described infra, e.g. an exosome, is a predetermined amount calculated to achieve the desired effect. In some embodiments, the effective amount is a prophylactic amount. In some embodiments, the effective amount is an amount used to medically treat the disease or condition. The specific dose of a composition administered according to this invention to obtain therapeutic and/or prophylactic effects will, of course, be determined by the particular circumstances surrounding the case, including, for example, the composition administered, the route of administration, and the condition being treated. It will be understood that the effective amount administered will be determined by the physician in the light of the relevant circumstances including the condition to be treated, the choice of composition to be administered, and the chosen route of administration. A therapeutically effective amount of composition of this invention is typically an amount such that when it is administered in a physiologically tolerable excipient composition, it is sufficient to achieve an effective systemic concentration or local concentration in the targeted tissue.

The terms "treat," "treated," or "treating," as used herein, can refer to both therapeutic treatment or prophylactic or preventative measures, wherein the object is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results may include, but are not limited to one or more of the following: alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response. Treatment also includes prolonging survival as compared to expected survival if not receiving treatment.

Exosomes

Exosomes of the invention are double membrane bound vesicles secreted from cells of plants and animals, such as mammals including humans, non-human primates, dogs, cats, sheep, cows, pigs, horses, rabbits, mice, rats and guinea pigs to name but a few. Thus exosomes may be isolated from any cell type from any source. In some embodiments of the invention the exosomes of the invention may be secreted from a human cell, such as a human clonal progenitor cell. In some embodiments the exosomes may be secreted from an endothelial human clonal progenitor cell.

The exosomes may contain one or more markers expressed by their cell of origin. In some embodiments the exosomes contain CD63.

The exosomes may contain one or more miRNAs. In some embodiments, the exosomes of the invention contain one or more miRNAs chosen from Table 2 or 4. In some embodiments, the exosomes of the invention contain one or more angiogenic miRNAs. In some embodiments, the exosomes of the invention contain miR-126.

Where the exosomes are derived from a clonal progenitor cell, the exosomes will be of uniform quality and composition. Thus the exosomes isolated from a clonal progenitor cell will not vary as a result of genetic variation of the source cell. The molecular composition of the contents and the bio-physical characteristics of the vesicles will be consistent and reproducible. Moreover, because of the replicative capacity of the human embryonic progenitor cells, the invention provides an overabundance of the exosomes of the invention. This is in direct contrast with exosomes obtained from other sources known in the art where the paucity of the cell type or the problem of senescence limits the availability of a reproducible exosome. Moreover, in certain embodiments the cells giving rise to the exosomes of the invention, are neither transformed nor malignant, thus avoiding any possible concern regarding carcinogenesis of the exosomes.

The exosomes of the invention may have diameter ranging from about 20 nm-130 nm; from about 30 nm-120 nm; about 40 nm-110 nm; about 50 nm-100 nm; about 85 nm-95 nm. In some embodiments the exosomes of the invention have a diameter of about 90 nm. In some embodiments the exosomes of the invention have a diameter of about 88 nm.

The exosomes may be comprised of a lipid bilayer containing trans-membrane proteins and may contain hydrophilic components within the vesicle of the exosome. The contents of the vesicle may be derived from the cytoplasm of the cell or from other vesicle structures within the cell, e.g., endosomes. The vesicle may contain nucleic acids, such as DNA, RNA including mRNA, miRNA as well as proteins and peptides.

The exosomes of the invention may serve as depots for the delivery of therapeutic molecules of any kind. The exosomes of the invention can be engineered to contain therapeutic molecules such as nucleic acids, proteins, peptides, small molecules such as drugs and the like. Any technique known in the art can be used to load the exosomes of the invention with a desired therapeutic molecule. For example cationic lipids could be used to transfect the exosomes with a desired nucleic acid such as DNA, RNA, include mRNA and miRNA. HIV that protein could be used to transport protein or peptide therapeutics into the exosomes of the invention. The therapeutic molecules can be chosen, engineered or designed to have any desired therapeutic effect. For example molecules associated with enhanced angiogenesis could be loaded into the exosomes of the invention, e.g. VEGF.

The secreted exosomes of the invention can be contacted with a target cell (e.g. a cell that is not the same as the cell of origin for the exosome) such that the exosome is taken up by the target cell, e.g. endocytosed. Once inside the cell, the contents of the vesicle may be released into the cytoplasm where the molecules contained within the vesicle may act as signaling molecules in one or more signaling pathways thereby inhibiting or enhancing gene expression. The signaling molecules may act at the level of transcription or translation for example. In some instances, where the vesicles contain RNA, the RNA can be transcribed by the target cell. In some instances where the RNA is a miRNA the miRNA can inhibit gene expression.

Methods of Isolating Exosomes

Exosomes may be isolated from any suitable cell that contains exosomes. Described infra are several exemplary cell and cell types that may be used to implement this method. The method may involve seeding the cell at an appropriate density in a tissue culture vessel and then incubating the cells in a suitable media or buffer for a suitable period of time. In some embodiments the cells may be permitted to attach to the culture vessel before the exosomes are isolated. In other embodiments the cells may be kept in suspension while the exosomes are isolated. The cells may be permitted to replicate in culture before the exosomes are isolated. Alternatively, the exosomes may be isolated from the cells that have not replicated, or replicated minimally (e.g. less than 1 doubling).

To initiate the method the cells are seeded in a tissue culture method at a suitable cell density. The cell density (cells per unit area) may range from about 5 k/cm$^2$, about 10 k/cm$^2$, about 15 k/cm$^2$, about 20 k/cm$^2$, about 25 k/cm$^2$, about 30 k/cm$^2$, about 35 k/cm$^2$, about 40 k/cm$^2$, about 45 k/cm$^2$, about 50 k/cm$^2$, about 55 k/cm$^2$, about 60 k/cm$^2$, about 70 k/cm$^2$, about 75 k/cm$^2$. In some embodiments the cell density (cells per unit area) may range from about 1 k/cm$^2$-100 k/cm$^2$, 10 k/cm$^2$-90 k/cm$^2$, 20 k/cm$^2$-80 k/cm$^2$, 30 k/cm$^2$-70 k/cm$^2$, 40 k/cm$^2$-60 k/cm$^2$. In one embodiment the cells are seeded at a density (cells per unit area) of 40 k/cm$^2$.

The cells may be seeded in any isotonic solution. In one embodiment a suitable solution may include a suitable buffer. Examples of suitable buffers may include phosphate buffered saline (PBS), HEPES and the like. In other embodiments the cells may be seeded in any suitable cell culture media, many of which are commercially available. Exemplary media include DMEM, RPMI, MEM, Media 199, HAMS and the like. In one embodiment the media is EGM-MV2. The media may be supplemented with one or more of the following: growth factors, cytokines, hormones, serum, such as fetal calf serum, serum substitutes such as knock out replacement serum or B27, antibiotics, vitamins and/or small molecule drugs. In one embodiment the media is supplemented with a TGFβ inhibitor, e.g. SB43154).

The method may be practiced by placing the cells in a suitable environment, such as a cell incubator heated to about 37° C. In some embodiments the cells may be incubated at room temperature. The incubator may be humidified and have an atmosphere that is about 5% $CO_2$ and about 1% $O_2$. In some embodiments the $CO_2$ concentration may range from about 1-20%, 2-10%, 3-5%. In some embodiments the $O_2$ concentration may range from about 1-20%, 2-10%, 3-5%.

The method may be practiced by incubating the cells in the media or buffer for about 1-72 hours, 1-48 hours, 2-24 hours, 3-18 hours, 4-16 hours, 5-10 hours. In some embodiments the cells are incubated for about 16 hours.

Incubation of the cells as described above allows for the exocytosis of the exosomes by the cells into the isotonic solution. After incubation of the cells in the isotonic solution as described above, the isotonic solution may be harvested. For example the isotonic solution may be pipetted or decanted into another vessel such as a centrifuge tube. A precipitating agent may be added to the isotonic solution at this time to facilitate the precipitation of the exosomes in the solution. Examples of precipitating agents include a solution that is about 15% polyethylene glycol. Alternatively, a commercially prepared precipitating agent may be used, e.g., Total Exosome Isolation Reagent (Life Technologies, Carlsbad, Calif.). The cells may then be incubated for a suitable time period e.g., 1-48 hours, 2-24 hours, 3-18 hours, 4-16 hours, 5-10 hours. In some embodiments the cells are incubated for about 16 hours. The cells may be incubated at a temperature of about 1° C., 5° C., 10° C., 15° C., 20° C., 25° C., 30° C. In one embodiment the cells are incubate at about 4° C.

After incubating the harvested cell conditioned isotonic solution with the precipitating reagent described above the harvested cell conditioned isotonic solution may be centrifuged at about 1,000×g, 2,000×g, 4,000×g, 6,000×g, 8,000×g; 10,0000×g; 12,000×g, 14,000×g, 16,000×g; 18,000×g. In one embodiment the harvested cell conditioned isotonic solution is centrifuged at about 10,000×g. The harvested cell conditioned isotonic solution may be centrifuged at about a temperature of 2° C., 4° C., 6° C., 8° C., 10° C., 12° C., 14° C., 16° C., 18° C., 20° C., 22° C., 24° C., 26° C. In one embodiment the harvested cell conditioned isotonic solution are centrifuged at about a temperature of 4° C.

After centrifugation the isotonic solution is removed and the exosomes are resuspended in a suitable buffer such as PBS. The volume of buffer may be about 0.01 volumes-about 0.09 volumes, about 0.02 volumes to about 0.08 volumes; about 0.03 volumes to about 0.07 volumes of the precipitating solution. In one embodiment the harvested cell conditioned isotonic solution is resuspended in PBS at a volume equivalent to about 0.01 volumes of the precipitating solution. The harvested exosomes may be used immediately or frozen and stored, e.g., at −20° C., for later use.

Progenitor Cells

In certain embodiments of the invention progenitor cells serve as the source of the exosomes described infra. The progenitor cell may be from any animal or plant. For example the exosome may be from a mammal, such as a human, a non-human primate, a horse, a cow, a sheep, a goat, a pig, a cat, a dog, a rabbit, a guinea pig, a rodent such as a mouse or a rat. Typically a progenitor cell will not have an essentially unlimited replicative capacity as typically found in embryonic stem cells, but will nonetheless have, a result of their longer telomeres, a greater replicative capacity compared to adult primary cells or tissues (e.g. primary cells) or adult stem cells.

The progenitor cell may be derived from a pluripotent stem cell, such as an embryonic stem cell or an induced pluripotent stem cell. The progenitor cell may be a clonal cell or an oligoclonal cell. An oligoclonal cell would include a population of cells similar cells, e.g. phenotypically or genetically. The progenitor cell may be a clonal human embryonic progenitor cell. The progenitor cell may be a clonal human embryonic endothelial progenitor cell. The progenitor cell may be a clonal embryonic progenitor cell that expresses CD31 and CD36. The progenitor cell may be a clonal embryonic progenitor cell expressing one or more genes listed in Table 1. The progenitor cell may be a clonal embryonic progenitor cell expressing a plurality of the genes listed in Table 1. The progenitor cell may be a clonal embryonic progenitor cell expressing the genes listed in Table 1.

Where the progenitor cells are clonal cells obtained from pluripotent stem cells they will provide an almost unlimited source of the same exosomes. This is due to two factors: the genetic identity of the original cellular source material and the enhanced telomere lengths found in early progenitors which provide for enhanced replicative capacity relative to adult tissue or cells or adult stem cells. Moreover, unlike adult stem cells which are typically available in very small numbers and are difficult to expand in culture, the clonal embryonic progenitors described infra are available in large numbers and are relatively easy to expand in culture.

In some embodiments the progenitor cell is not an adult stem cell. In some embodiments of the invention the progenitor cell is not an MSC. In some embodiments the clonal progenitor cell is not transfected or engineered to express an exogenous gene. In some embodiments the clonal progenitor cell is not transfected to express an oncogene. In some embodiments the clonal progenitor does not express c-myc. In other embodiments the clonal progenitor cell is transfected or engineered to express an exogenous gene. Examples of suitable exogenous genes include the catalytic component of human telomerase, e.g. hTERT.

Uses of Exosomes

The exosomes described herein may be used in therapeutic, research and diagnostic applications. For example the exosomes described infra may be added to a cell culture to enhance one or more phenotypic traits of the cells. The exosomes of the invention may be added to a cell culture to inhibit one or more phenotypic traits of the cells. The exosomes of the invention may be added to a cell culture to provide a new phenotypic trait of the cells.

The exosomes of the invention may be added to a culture of endothelial cells to enhance the ability of the cells to form vascular tube like structures. The exosomes of the invention may be added to any cell having the ability to form vascular tube like structures to enhance the cells ability to form tube like structures.

In some embodiments the exosomes of the invention are contacted with a cell thereby providing at least one new phenotypic trait to the cell. For example, the exosomes of the invention may confer the ability to form vascular tube like structures to cell lacking the ability to form vascular tube like structures before it was contacted with the exosomes of the invention.

In certain embodiments the exosomes of the invention may be added to a culture of perivascular cells to enhance the ability of the perivascular cells to form vascular tube like structures.

In some embodiments the invention provides a method of increasing the length of a vascular tube like structure formed by a cell such as an endothelial relative to an endothelial cell that has not been treated with the exosomes of the invention comprising contacting the endothelial cell with an exosome isolated from a progenitor cell such as a human clonal progenitor cell, e.g., 30-MV2-6 cells. In some embodiments the invention provides a method of increasing the length of a vascular tube like structure formed by a cell such as a perivascular cell relative to a perivascular cell that has not been treated with the exosomes of the invention comprising contacting the perivascular cell with an exosome isolated from a progenitor cell such as a human clonal progenitor cell, e.g., 30-MV2-6 cells. In some embodiments the invention provides a method of increasing the branching of a vascular tube like structure formed by an endothelial cell relative to an endothelial cell that has not been treated with the exosomes of the invention comprising contacting the endothelial cell with an exosome isolated from a progenitor cell such as a human clonal progenitor cell, e.g., 30-MV2-6 cells. In some embodiments the invention provides a method of increasing the branching of a vascular tube like structure formed by a perivascular cell relative to a perivascular cell that has not been treated with the exosomes of the invention comprising contacting the perivascular cell with an exosome isolated from a progenitor cell such as a human clonal progenitor cell, e.g., 30-MV2-6 cells. In still other embodiments the invention provides a method of increasing the number of loops in the vascular tube like structures formed by an endothelial cell relative to an endothelial cell that has not been treated with the exosomes of the invention comprising contacting the endothelial cell with an exosome isolated from a progenitor cell such as a human clonal progenitor cell, e.g., 30-MV2-6 cells. In yet other embodiments the invention provides a method of increasing the number of loops in the vascular tube like structures formed by a perivascular cell relative to a perivascular cell that has not been treated with the exosomes of the invention comprising contacting the perivascular cell with an exosome isolated from a progenitor cell such as a human clonal progenitor cell, e.g., 30-MV2-6 cells.

The exosomes of the invention may be administered therapeutically to a subject in need of treatment. For example the exosomes of the invention may be administered to a subject in need of treatment for any disease requiring the enhanced ability to form vascular tube like structures. The exosomes of the invention may be used to treat a subject suffering from cardiovascular disease, heart failure, infarction, chronic wounds, ulcer, clogged vessels or arteries, damaged vessels, stenotic vessels, arteriosclerosis, angina, peripheral vascular disease, Alzheimer's disease, ischemia, diabetes, cancer, cell replacement transplant or therapy, tissue and cell regenerative therapy and Parkinson's disease. The exosomes may be used as depot to deliver therapeutic molecules such as small molecules, nucleic acids, proteins and peptides.

The exosomes of the invention may be directly administered to a subject in need of treatment or an in vitro cell culture. Alternatively the exosomes can be provided enclosed within a matrix or scaffold. Suitable matrices or scaffolds may include a matrix or scaffold comprised of one or more extracellular matrix proteins, e.g. laminin, fibronectin and the like. Other suitable matrices or scaffolds include Matrigel® which is a murine sarcoma extract. The matrix or scaffold may be a hydrogel. The hydrogel may be comprised of hylauronate and gelatin (see U.S. Pat. Nos. 8,324,184; 7,928,069). In one embodiment the exosomes of the invention may be delivered in HyStem (Biotime, Inc., Alameda Calif.).

Using the methods described infra along with routine chromatographic techniques known in the art the exosomes of the invention may be used to isolate one or more nucleic acids, proteins or peptides expressed by a progenitor cell serving as the source of the exosome. Once isolated, the proteins or peptides isolated from the exosomes of the invention can be used to make antibodies to the isolated proteins or peptides (See Harlow et al. Antibodies: A Lab Manual $2^{nd}$ Edition; Cold Spring Harbor Press 2013).

The exosomes of the invention may be used in drug screening assays. For example where the exosomes described infra enhance vascular tube formation in vitro, the exosomes can be used to screen for drugs that enhance or inhibit this capability. A cell culture comprising cells having the ability to form vascular tube like structures may be contacted with the exosomes of the invention and a drug candidate may be applied to the same cell culture either before, after or simultaneously with the exosomes to determine the effect of the drug the ability of the exosomes to enhance vascular tube formation in the cell culture. The effects can be compared to untreated cells and cells treated only with the exosomes of the invention.

Pharmaceutical Compositions

Modes of administration for a therapeutic (either alone or in combination with other pharmaceuticals) can be, but are not limited to, sublingual, injectable (including short-acting, depot, implant and pellet forms injected subcutaneously or intramuscularly), or by use of vaginal creams, suppositories, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of therapeutic to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the therapeutic of the present disclosure and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compositions of the present disclosure can be formulated for parenteral administration by injection, e.g., by bolus injection or continuous infusion. The compositions can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compositions can be formulated readily by combining the therapeutic with pharmaceutically acceptable carriers well known in the art. Such carriers enable the therapeutic of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinyl pyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active therapeutic doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active therapeutic can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the pharmaceutical compositions can take the form of, e.g., tablets or lozenges formulated in a conventional manner.

For administration by inhalation, the therapeutic for use according to the present disclosure is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the therapeutic and a suitable powder base such as lactose or starch.

The compositions of the present disclosure can also be formulated in rectal compositions such as suppositories or retention enemas, e.g., containing conventional suppository bases such as cocoa butter or other glycerides.

In addition to the formulations described previously, the therapeutic of the present disclosure can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions of the present disclosure, for example, can be applied to a plaster, or can be applied by transdermal, therapeutic systems that are consequently supplied to the organism.

Pharmaceutical compositions can include suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compositions of the present disclosure can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component may include one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearylfumarate, fatty acid, fatty alcohol, fatty acid ester, glycerylbehenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

Kits

In some embodiments the invention provides a kit comprising exosomes isolated from a progenitor cell, such as a human clonal progenitor cell. The progenitor cell may be an endothelial progenitor cell, such as human clonal embryonic progenitor cell, e.g. 30MV2-6. The exosomes may be provided in one or more containers. The exosomes may be provided in a suitable buffer, e.g. PBS or a suitable media, such as a commercially available cell culture media, e.g. DMEM. The kit may further contain a cell having the ability to form vascular tube like structures. The cell may be an endothelial cell, e.g. HUVEC and/or a perivascular cell. The cells may be provided in a suitable media, e.g. DMEM or the like or alternatively the cells may be provided in a buffer such as PBS. In some embodiments the cells may be provided frozen in a suitable freezing media such as a commercially available media supplemented with DMSO. The kit may optionally include instructions as to how to reconstitute the exosomes, culture the cells and/or contact the cells with exosomes so as to enhance vascular tube like formation.

In other embodiments the invention provides a kit comprising a human clonal embryonic progenitor cell, such as 30-MV2-6. The cell may be provided in at least one container in suitable media or buffer. The kit may include buffers and/or media for isolating exosomes from the cells. The kit may contain one or more vessels, e.g. a multi-well plate for culturing the cells. The kit may further contain a cell line capable of forming vascular tube like structures such as endothelial cells. Suitable cells include endothelial cells such as HUVEC and/or a a perivascular cell. Any or all of the cells may be provided frozen in a suitable media, e.g. freezing media such as a commercially available media supplemented with DMSO. The kit may optionally include instructions as to how to culture the cells and/or contact the endothelial cells with exosomes isolated from the progenitor cells so as to enhance or induce vascular tube like formation.

Additional Embodiments of the Invention.

1. An exosome isolated from a progenitor cell line.
2. The exosome of 1, wherein the progenitor cell line is a human progenitor cell line.
3. The exosome of 1, wherein the progenitor cell line is a clonal progenitor cell line.
4. The exosome of 1, wherein the progenitor cell line is an endothelial progenitor cell line.
5. The exosome of 1, wherein the exosome contains CD63.
6. The exosome of 1, wherein the exosome contains one or more miRNAs listed in Table 2 or Table 4.
7. The exosome of 1, wherein the exosome contains one or more angiogenic miRNAs.
8. The exosome of 1, wherein the exosome contains miR-126.
9. The exosome of 1, wherein the progenitor cell line expresses CD31 and CD34.
10. The exosome of 1, wherein the progenitor cell line expresses one or more genes listed in Table 1.
11. The exosome of 1, wherein the progenitor cell line is 30-MV2-6.
12. The exosome of 1, wherein the exosome enhances the formation of vascular tube like formations when contacted with an endothelial cell.
13. The exosome of 1 further comprising a pharmaceutical carrier.
14. A method of isolating an exosome from a clonal progenitor cell comprising 1) culturing the clonal progenitor cell in a suitable media or buffer for a time sufficient to allow the clonal progenitor cell to exocytose exosomes into the culture media or buffer; 2) harvesting the media or buffer from the cell culture of step 1; and 3) isolating the exosomes from the media or buffer of step 2, thereby isolating an exosome from a clonal progenitor cell.
15. The method of 14, wherein the suitable media or buffer is PBS.
16. The method of 14, wherein the suitable media or buffer is EGM-MV2.
17. The method of 14, wherein after step 2 a precipitating agent is added to the media or buffer.
18. The method of 14, wherein the precipitating agent comprises polyethylene glycol.
19. The method of 14, wherein step 3 comprises centrifuging the harvested media of buffer.
20. The method of 14, wherein the suitable time of step 1 is about 16 hours.
21. The method of 14, wherein after step 2, the method further comprises a step of incubating harvested media or buffer.
22. The method of 21, wherein the incubation step is performed for about 16 hours.
23. The method of 21, wherein the incubation step is performed at about 4° C.
24. A cell culture comprising an exosome isolated from a progenitor cell and a cell which was not the source of the isolated exosome.
25. The exosome of 24, wherein the progenitor cell line is a human progenitor cell line.
26. The exosome of 24, wherein the progenitor cell line is a clonal progenitor cell line.
27. The exosome of 24, wherein the progenitor cell line is an endothelial progenitor cell line.
28. The exosome of 24, wherein the exosome contains CD63.
29. The exosome of 24, wherein the exosome contains one or more miRNAs listed in Table 2 or Table 4.
30. The exosome of 24, wherein the exosome contains one or more angiogenic miRNAs.
31. The exosome of 24, wherein the exosome contains miR-126.
32. The exosome of 24, wherein the progenitor cell line expresses CD31 and CD34.
33. The exosome of 24, wherein the progenitor cell line expresses one or more genes listed in Table 1.

34. The exosome of 24, wherein the progenitor cell line is 30-MV2-6.

35. The exosome of 24, wherein the exosome enhances the formation of vascular tube like formations when contacted with an endothelial cell.

36. A method of inducing or enhancing a cell's ability to form vascular tube like structures comprising contacting a cell capable of making vascular tube like structures with an exosome isolated from a progenitor cell thereby inducing or enhancing a cells ability to form vascular tube like structures.

37. The method of 36, wherein the cell capable of making vascular tube like structures is an endothelial cell.

38. The method of 37, wherein the endothelial cell is a HUVEC.

39. A method of treating a subject in need of vascular therapy comprising administering an exosome isolated from a progenitor cell.

40. The method of 39, wherein the subject is human.

41. The method of 39, wherein the subject exosome is administered to the subject to treat a condition chosen from cardiovascular disease, heart failure, infarction, chronic wounds, ulcer, clogged vessels or arteries, damaged vessels, stenotic vessels, arteriosclerosis, angina, peripheral vascular disease, Alzheimer's disease, ischemia, diabetes, cancer, cell replacement transplant or therapy, tissue and cell regenerative therapy and Parkinson's disease.

42. The method of 39, wherein the progenitor cell line is a human progenitor cell line.

43. The method of 39, wherein the progenitor cell line is a clonal progenitor cell line.

44. The method of 39, wherein the progenitor cell line is an endothelial progenitor cell line.

45. The method of 39, wherein the exosome contains CD63.

46. The method of 39, wherein the exosome contains one or more miRNAs listed in Table 2 or Table 4.

47. The method of 39, wherein the exosome contains one or more angiogenic miRNAs.

48. The method of 39, wherein the exosome contains miR-126.

49. The method of 39, wherein the progenitor cell line expresses CD31 and CD34.

50. The method of 39, wherein the progenitor cell line expresses one or more genes listed in Table 1.

51. The method of 39, wherein the progenitor cell line is 30-MV2-6.

52. The method of 39, wherein the exosome enhances the formation of vascular tube like formations when contacted with an endothelial cell.

53. The method of 39 further comprising a pharmaceutical carrier.

EXAMPLES

Example 1: Preparation of Exosomes Derived from a Human Embryonic Progenitor Cell Line Exosomes were prepared from a human embryonic progenitor cell line (PureStem® cell line, ESI Bio, Alameda, Calif.). PureStem® cell lines are scalable clonally pure embryonic progenitor cell lines derived from human embryonic stem (hES) cells (West et al. (2008) *Regen Med.* 3(3):287). The 30-MV2-6 PureStem® cell line is a CD31 positive, CD34 positive, endothelial progenitor line derived from the ESI-017 embryonic stem cell line. A gene expression profile of the 30-MV2-6 cells as analyzed by microarray is provided herein in Table 1, and includes genes yielding relative fluorescence units >1000 rfu.

TABLE 1

| Gene symbol | 30-MV2-6 P6, MBA_3877 |
|---|---|
| EEF1A1 | 29470.94 |
| EEF1A1 | 28581.27 |
| EEF1A1 | 28032.06 |
| TMSB4X | 27627.77 |
| GNB2L1 | 27295.94 |
| TPT1 | 26985.77 |
| LOC100129758 | 26697.4 |
| LAIR1 | 26461.51 |
| F2R | 26252 |
| LOC285176 | 26055.83 |
| RPL41 | 25872.51 |
| NAG18 | 25689.47 |
| LOC649150 | 25513.84 |
| FTL | 25344.95 |
| LOC91561 | 25177.92 |
| LOC100132593 | 25023.94 |
| RPLP2 | 24889.1 |
| LOC388474 | 24755.51 |
| MGC16703 | 24611.59 |
| UBC | 24480.02 |
| LOC389342 | 24350.84 |
| CLUAP1 | 24238.08 |
| RPS27 | 24117.06 |
| ZNF674 | 23992.58 |
| IMAA | 23881.17 |
| RRP7B | 23769.37 |
| C19orf31 | 23655.06 |
| ANXA2P2 | 23547.03 |
| LOC401206 | 23440.4 |
| LOC100133876 | 23333.52 |
| GGA1 | 23233.85 |
| MSH3 | 23140.74 |
| LOC729439 | 23047.74 |
| LOC440589 | 22950.21 |
| UBC | 22847.36 |
| FTL | 22745.35 |
| LOC100130553 | 22658.54 |
| LOC728658 | 22562.38 |
| ACTG1 | 22481.09 |
| LOC644604 | 22386.22 |
| RPL38 | 22292.94 |
| LOC642210 | 22201 |
| LOC148430 | 22112.95 |
| LOC100133465 | 22026.54 |
| LOC400963 | 21937.41 |
| TMSB10 | 21854.66 |
| LOC284393 | 21771.97 |
| RN7SL1 | 21682.27 |
| RPS29 | 21599.25 |
| LOC100133931 | 21519.28 |
| RPS12 | 21431.97 |
| ITIH5 | 21348.51 |
| LOC341457 | 21263.76 |
| LOC642250 | 21185.09 |
| KIAA0101 | 21102.53 |
| LOC389435 | 21019.57 |
| LOC100132488 | 20946.02 |
| ANXA2 | 20864.81 |
| LOC441034 | 20786.82 |
| RPS19 | 20710.05 |
| ACTB | 20640.19 |
| LOC440589 | 20572.73 |
| LOC388720 | 20496.3 |
| LOC728658 | 20419.73 |
| FAM177A1 | 20346.14 |
| LOC387930 | 20271.08 |
| LOC440595 | 20196.18 |
| LOC653232 | 20127 |
| ORC6L | 20058.03 |
| RPS25 | 19986.5 |
| ACTB | 19922.52 |
| LOC100130980 | 19848.39 |
| PDCD7 | 19772.26 |

TABLE 1-continued

| Gene symbol | 30-MV2-6 P6, MBA__3877 |
|---|---|
| RPL18A | 19703.81 |
| LOC642892 | 19628.75 |
| LOC727808 | 19558.66 |
| LOC389223 | 19478.59 |
| ROCK2 | 19416.46 |
| CCR6 | 19350.04 |
| RPS15A | 19290.37 |
| RPS11 | 19219.96 |
| RPL18 | 19149.27 |
| RPL6 | 19086.13 |
| RPS29 | 19022.98 |
| RPL38 | 18959.29 |
| RPL27A | 18894.7 |
| RPS27 | 18834.63 |
| LOC387841 | 18770.86 |
| TUBA1A | 18706.36 |
| LOC647361 | 18639.92 |
| RPL11 | 18576.44 |
| LOC100130446 | 18517.91 |
| LOC728553 | 18455.8 |
| UBA52 | 18391.57 |
| LOC728576 | 18328.88 |
| LOC100129553 | 18269.35 |
| MYL6 | 18203.91 |
| ACTG1 | 18140.81 |
| FTHL16 | 18076.95 |
| LOC441876 | 18016.04 |
| LOC343184 | 17954.72 |
| LOC391777 | 17893.68 |
| RPL9 | 17830.68 |
| RPS27A | 17768.43 |
| LOC643863 | 17711.83 |
| RPS6 | 17652.27 |
| PSMD12 | 17594.21 |
| MYL6 | 17535.65 |
| LOC646195 | 17476.44 |
| RPL32 | 17418.94 |
| RPLP0 | 17356.64 |
| LOC729402 | 17294.36 |
| RPS17 | 17236.98 |
| RPL35A | 17181.16 |
| RPL11 | 17118.82 |
| RPL18A | 17060.66 |
| LOC100129158 | 17003.18 |
| LOC401019 | 16944.5 |
| LOC100133607 | 16889.64 |
| LOC729324 | 16834.91 |
| LOC645895 | 16775.01 |
| LOC649076 | 16721.19 |
| RPS16 | 16662.93 |
| PPIAL4A | 16607.66 |
| RPL17 | 16550.82 |
| RPS10 | 16491.53 |
| LOC440733 | 16435.98 |
| RPL18A | 16384.7 |
| LOC645899 | 16331.75 |
| LOC644029 | 16276.86 |
| VIM | 16220.75 |
| LOC100129902 | 16168.98 |
| LOC440027 | 16117.11 |
| LOC728517 | 16063.24 |
| C10orf58 | 16009.07 |
| LOC728368 | 15951.03 |
| LOC439953 | 15892.32 |
| LOC651894 | 15837.98 |
| LOC644745 | 15784.83 |
| FARSLB | 15733.5 |
| LOC388524 | 15675.03 |
| FTHL7 | 15621.63 |
| RPL27 | 15573.05 |
| RPL12 | 15524.71 |
| RPL37A | 15473.36 |
| RPLP1 | 15423.13 |
| RPS20 | 15371.34 |
| RPS14 | 15315.83 |
| XPNPEP3 | 15265.39 |
| LOC389101 | 15209.69 |
| LOC402057 | 15164.27 |
| LOC643509 | 15114.24 |
| LOC284230 | 15063.66 |
| LOC642357 | 15015.66 |
| LOC652071 | 14963.6 |
| RPL39 | 14914.66 |
| LOC728576 | 14864.7 |
| LOC644464 | 14816.74 |
| ACTB | 14769.08 |
| RPL30 | 14718.38 |
| RPS3 | 14668.78 |
| IFITM2 | 14620.77 |
| LOC644039 | 14568.97 |
| LOC645683 | 14518.14 |
| FAM115A | 14471.98 |
| RPL19 | 14423.17 |
| LOC653162 | 14375.34 |
| LOC441775 | 14323.48 |
| LGALS1 | 14273.15 |
| RPS24 | 14227.73 |
| RPL3 | 14179.84 |
| RPS15 | 14130.03 |
| GNG11 | 14079.57 |
| CAV1 | 14033.15 |
| LOC729090 | 13979.81 |
| TM4SF1 | 13927.96 |
| NACA | 13881.36 |
| ATP5EP2 | 13834.41 |
| LOC653881 | 13785.78 |
| RPL17 | 13738.14 |
| OAZ1 | 13689.32 |
| LOC645296 | 13641.2 |
| S100A10 | 13595.26 |
| RPL31 | 13545.91 |
| RPL24 | 13494.67 |
| LOC100128505 | 13442.05 |
| LOC645174 | 13394.88 |
| LOC648729 | 13345.11 |
| RPL8 | 13298.89 |
| LOC731096 | 13253.78 |
| LOC642741 | 13211.35 |
| LOC647276 | 13169.46 |
| LOC729903 | 13121.3 |
| LOC401019 | 13076.43 |
| LOC728128 | 13029.34 |
| CD81 | 12985.19 |
| LOC731542 | 12939.34 |
| LOC651436 | 12894.54 |
| RPL10A | 12850.49 |
| LOC441013 | 12803.59 |
| RPS4X | 12755.92 |
| GJC1 | 12710.73 |
| LDB2 | 12664.08 |
| RPS8 | 12614.56 |
| BTF3 | 12567.71 |
| WBP5 | 12522.85 |
| LOC650276 | 12477.88 |
| PFN1 | 12433.05 |
| RPL6 | 12389.93 |
| LOC100129141 | 12346.77 |
| ATP5B | 12304.98 |
| CD93 | 12259.89 |
| VIM | 12217.76 |
| LOC730754 | 12172.71 |
| HSPB1 | 12127.76 |
| LOC728453 | 12085.1 |
| EIF4A1 | 12041.45 |
| LOC389404 | 11999.19 |
| CD151 | 11957.83 |
| LOC647276 | 11912.95 |
| LOC729789 | 11868.46 |
| LOC728937 | 11828.98 |
| IFITM3 | 11788.35 |
| LILRB3 | 11744.43 |
| LOC646294 | 11705.26 |
| RPS2 | 11661.18 |
| FSCN1 | 11621.16 |

TABLE 1-continued

| Gene symbol | 30-MV2-6 P6, MBA__3877 |
|---|---|
| LOC441246 | 11578.21 |
| LOC645387 | 11538.01 |
| LOC647099 | 11499.43 |
| PRCP | 11460.34 |
| SOX18 | 11422.95 |
| LOC440575 | 11382.54 |
| LOC641814 | 11344.01 |
| KCNH6 | 11306.56 |
| LOC653314 | 11266.4 |
| LOC100133649 | 11225.89 |
| LOC729603 | 11184.33 |
| TUBA1C | 11147.33 |
| LOC286444 | 11110.15 |
| LOC643531 | 11068.19 |
| LOC643284 | 11030.72 |
| AP2S1 | 10993.52 |
| PTRF | 10952.09 |
| H3F3A | 10913.04 |
| LOC100132742 | 10876.23 |
| LOC648210 | 10835.95 |
| EIF3E | 10798.77 |
| RPL3 | 10762.44 |
| TXN | 10725.63 |
| RPS29 | 10688.26 |
| MYL12A | 10651.34 |
| GABPB2 | 10615.8 |
| RPS9 | 10581.37 |
| ATP5EP2 | 10543.17 |
| LOC647000 | 10509.38 |
| UBB | 10473.09 |
| LOC388556 | 10436.98 |
| LOC728693 | 10403.82 |
| NGFRAP1 | 10370.85 |
| COX7C | 10337.94 |
| GAPDH | 10305.26 |
| GNAS | 10271.86 |
| LOC400721 | 10233.35 |
| ICAM2 | 10200.27 |
| RPS3A | 10164.91 |
| LOC100131713 | 10128.06 |
| B2M | 10097.39 |
| UBB | 10066.7 |
| CLEC2D | 10033.68 |
| MGC26356 | 10004.77 |
| LOC100133273 | 9971.113 |
| TPT1 | 9939.753 |
| RPSA | 9911.836 |
| RPS13 | 9882.49 |
| ENO1 | 9852.533 |
| LOC100132742 | 9822.571 |
| LOC729617 | 9790.951 |
| S100A10 | 9759.989 |
| LOC730187 | 9729.674 |
| LOC648000 | 9697.648 |
| LOC644464 | 9669.355 |
| RPS5 | 9640.032 |
| RPL14L | 9608.673 |
| RPL36AL | 9578.568 |
| NEDD8 | 9548.513 |
| RPS6 | 9520.098 |
| TGFBR2 | 9492.364 |
| RPLP1 | 9463.913 |
| LOC440926 | 9432.986 |
| TUBA1B | 9407.654 |
| LOC284821 | 9377.909 |
| BTF3 | 9350.254 |
| LOC730246 | 9325.183 |
| LOC731365 | 9295.564 |
| LOC729466 | 9265.775 |
| LOC646200 | 9235.456 |
| ADAM15 | 9210.81 |
| RPS27L | 9182.401 |
| AKR1D1 | 9154.34 |
| CYB5R3 | 9128.27 |
| RPS3A | 9101.282 |
| RPS4X | 9076.407 |
| CREB1 | 9049.403 |
| PDE4C | 9022.809 |
| TFPI | 8997.954 |
| LOC728782 | 8971.264 |
| LOC645387 | 8944.967 |
| SEPT2 | 8917.304 |
| GLTSCR2 | 8894.782 |
| SLC25A5 | 8867.191 |
| LOC646294 | 8843.528 |
| PECAM1 | 8815.434 |
| H3F3A | 8791.886 |
| LOC649548 | 8767.153 |
| POTEF | 8740.947 |
| TGFBR2 | 8714.794 |
| VWF | 8689.385 |
| ITGB1 | 8666.613 |
| LOC729301 | 8641.795 |
| LOC100133812 | 8618.085 |
| EIF3L | 8594.98 |
| LOC642947 | 8573.153 |
| DNCL1 | 8550.102 |
| TFPI | 8526.81 |
| CDKN2AIPNL | 8504.479 |
| VAMP5 | 8479.908 |
| CDH5 | 8455.61 |
| LRAP | 8433.076 |
| RHOC | 8409.996 |
| CDKN1A | 8386.336 |
| S100A6 | 8366.138 |
| LOC645385 | 8343.072 |
| SNRPD2 | 8321.468 |
| ATP5A1 | 8298.988 |
| LDHA | 8275.572 |
| EEF2 | 8253.723 |
| LOC389141 | 8231.352 |
| COX4I1 | 8212.02 |
| RPS9 | 8190.523 |
| LOC650152 | 8168.617 |
| CDC37 | 8145.008 |
| LOC643358 | 8121.837 |
| LOC100133233 | 8102.312 |
| YWHAQ | 8082.7 |
| SNX3 | 8061.547 |
| AV762104 | 8040.466 |
| H3F3A | 8017.827 |
| PFN1 | 7996.922 |
| GAPDH | 7973.344 |
| YWHAZ | 7953.511 |
| RPS14 | 7934.452 |
| RPL15 | 7915.846 |
| FAU | 7885.26 |
| GPX1 | 7885.26 |
| LOC728620 | 7854.277 |
| RPL12 | 7833.73 |
| LOC648294 | 7816.09 |
| SLC16A12 | 7795.425 |
| LOC645715 | 7775.663 |
| RPS3A | 7756.622 |
| ALDOA | 7737.847 |
| CDK2AP1 | 7718.065 |
| TCEAL4 | 7699.396 |
| EEF1G | 7679.361 |
| LOC646766 | 7659.651 |
| LOC100190938 | 7640.343 |
| C21orf55 | 7621.212 |
| EIF4G2 | 7602.998 |
| LOC100128731 | 7583.863 |
| LOC100133177 | 7566.641 |
| ZNF430 | 7547.497 |
| CCNI | 7529.735 |
| RPL36 | 7510.359 |
| SERPINB6 | 7494.061 |
| LOC285053 | 7475.076 |
| EEF1B2 | 7455.902 |
| C11orf10 | 7436.825 |
| CALM3 | 7420.417 |
| LOC441087 | 7403.128 |
| TUBA1A | 7386.972 |

TABLE 1-continued

| Gene symbol | 30-MV2-6 P6, MBA__3877 |
|---|---|
| ZMAT3 | 7370.062 |
| KLF6 | 7351.817 |
| LOC643031 | 7336.027 |
| PABPC1 | 7319.402 |
| FKTN | 7301.646 |
| CFL1 | 7282.935 |
| LOC644863 | 7265.614 |
| RPS27A | 7248.343 |
| RPS17 | 7229.865 |
| COX7A2 | 7213.416 |
| RPS15A | 7198.388 |
| LOC100134134 | 7180.453 |
| ATP5G2 | 7162.671 |
| IL18 | 7144.369 |
| LOC283412 | 7127.359 |
| NUCB1 | 7110.135 |
| LOC729798 | 7092.872 |
| LOC387867 | 7076.424 |
| PCBP1 | 7060.549 |
| MRLC2 | 7043.793 |
| LOC389517 | 7027.69 |
| LOC399900 | 7013.314 |
| SERF2 | 6997.182 |
| EEF1B2 | 6981.873 |
| MARCKS | 6967.221 |
| NACA | 6951.604 |
| LOC100129424 | 6936.077 |
| NPC2 | 6920.058 |
| RPL35 | 6904.67 |
| GPX4 | 6889.884 |
| C10orf58 | 6874.525 |
| TOMM7 | 6860.304 |
| SLC25A3 | 6845.603 |
| MDH2 | 6832.719 |
| RPL26 | 6817.137 |
| ATP5I | 6800.876 |
| CTNNA1 | 6785.87 |
| RALA | 6771.026 |
| FAM69B | 6754.661 |
| CALM1 | 6738.351 |
| SHCBP1 | 6723.184 |
| SRP14 | 6708.369 |
| LOC646531 | 6693.502 |
| TACC1 | 6679.065 |
| DPYSL2 | 6663.472 |
| LOC100127993 | 6648.476 |
| LOC100130168 | 6634.481 |
| LOC285900 | 6620.755 |
| RPL7L1 | 6604.924 |
| PCBP2 | 6590.635 |
| PNPT1 | 6575.888 |
| HCG2P7 | 6562.18 |
| GPR116 | 6548.164 |
| H2AFZ | 6534.282 |
| COX6C | 6521.256 |
| ANXA5 | 6508.408 |
| NQO1 | 6495.337 |
| DAD1 | 6480.547 |
| COL4A1 | 6468.127 |
| ATP5A1 | 6454.348 |
| ZNF549 | 6440.91 |
| MYH9 | 6426.936 |
| SEC61G | 6412.935 |
| FKBP1A | 6399.774 |
| ARPC2 | 6387.262 |
| EIF4A2 | 6373.784 |
| EMP1 | 6360.16 |
| LOC729102 | 6346.829 |
| DDX5 | 6333.568 |
| HINT1 | 6318.728 |
| LOC645436 | 6305.671 |
| NOP10 | 6292.858 |
| PMP22 | 6279.687 |
| PSMB1 | 6265.957 |
| SQSTM1 | 6253.051 |
| LOC653737 | 6240.21 |
| HSPA8 | 6226.94 |
| TUBB | 6214.39 |
| SHANK3 | 6201.642 |
| UQCRH | 6188.65 |
| LOC730313 | 6176.263 |
| ATP5L | 6163.733 |
| LOC100133372 | 6150.941 |
| LOC550643 | 6139.155 |
| TXN | 6126.585 |
| DBI | 6113.103 |
| TMBIM6 | 6100.574 |
| SEPT2 | 6088.34 |
| LOC642489 | 6075.764 |
| CDAN1 | 6062.012 |
| PLSCR3 | 6050.002 |
| LOC649049 | 6038.353 |
| JUND | 6026.033 |
| YWHAH | 6013.875 |
| GSTP1 | 6002.531 |
| HSP90AA1 | 5991.17 |
| SLC44A4 | 5979.221 |
| PSAP | 5967.178 |
| CLDN5 | 5954.744 |
| LOC100130445 | 5943.334 |
| HNRNPD | 5931.25 |
| SOD1 | 5919.922 |
| EEF1AL7 | 5909.133 |
| LOC647856 | 5897.997 |
| TM4SF18 | 5886.761 |
| PTBP1 | 5875.687 |
| RAN | 5864.145 |
| RPL4 | 5852.968 |
| RAC1 | 5840.897 |
| CSTB | 5829.299 |
| C14orf156 | 5817.476 |
| NME1-NME2 | 5807.022 |
| ITM2B | 5796.124 |
| BGN | 5785.701 |
| SCD | 5776.214 |
| LOC645317 | 5764.427 |
| CMTM7 | 5753.074 |
| TOMM7 | 5741.794 |
| SEC61G | 5730.923 |
| PPM1F | 5719.127 |
| SLC25A3 | 5709.5 |
| ACVRL1 | 5699.607 |
| COMMD6 | 5689.162 |
| CLIC1 | 5677.854 |
| C17orf45 | 5667.08 |
| PRDX1 | 5656.452 |
| SAT1 | 5645.519 |
| SEPT9 | 5634.972 |
| ATP6AP2 | 5624.128 |
| CSDA | 5613.424 |
| PRDX1 | 5602.954 |
| BTG1 | 5592.841 |
| MTCH1 | 5582.283 |
| LOC134997 | 5573.499 |
| LOC286444 | 5563.255 |
| RPS18 | 5552.792 |
| HLA-E | 5543.25 |
| EDF1 | 5532.461 |
| ITGB1 | 5522.71 |
| MGST2 | 5511.287 |
| EIF3L | 5500.726 |
| TM4SF18 | 5490.636 |
| NONO | 5480.652 |
| ECSCR | 5470.367 |
| PSAP | 5460.726 |
| PSMA6 | 5451.676 |
| MARCKSL1 | 5442.01 |
| LOC729742 | 5432.988 |
| LOC100131387 | 5423.154 |
| NGFRAP1 | 5413.279 |
| MAP4K2 | 5402.065 |
| BEXL1 | 5392.217 |
| TBCA | 5382.14 |
| EIF1 | 5371.946 |

TABLE 1-continued

| Gene symbol | 30-MV2-6 P6, MBA__3877 |
|---|---|
| MCART1 | 5360.794 |
| MCM8 | 5351.053 |
| PSMB6 | 5340.972 |
| DAZAP2 | 5331.065 |
| QARS | 5320.504 |
| LOC440055 | 5310.703 |
| APLNR | 5301.342 |
| RPL13A | 5290.971 |
| C14orf85 | 5281.173 |
| CNN3 | 5271.19 |
| LOC100132795 | 5260.873 |
| LAMA5 | 5251.119 |
| SLC44A1 | 5241.342 |
| LOC100131609 | 5232.272 |
| ARL16 | 5222.225 |
| LOC100129362 | 5212.558 |
| WSB1 | 5203.553 |
| TSPO | 5193.677 |
| LOC645173 | 5184.411 |
| PRCP | 5175.037 |
| ESD | 5165.838 |
| HNRNPD | 5156.636 |
| LOC648771 | 5148.032 |
| CST3 | 5139.557 |
| PRKAR1A | 5130.244 |
| EPAS1 | 5121.617 |
| HSPA8 | 5112.767 |
| TPI1 | 5103.14 |
| NFIB | 5094.79 |
| LOC646942 | 5086.126 |
| NCOA4 | 5077.186 |
| FLOT2 | 5069.23 |
| LOC729978 | 5060.045 |
| IGFBP4 | 5051.913 |
| LOC650646 | 5043.719 |
| ANP32B | 5034.827 |
| CCND1 | 5026.154 |
| ATP5J | 5017.307 |
| SHFM1 | 5008.422 |
| ATP5O | 5000.003 |
| LOC440927 | 4992.161 |
| RHOA | 4983.717 |
| H2AFY | 4975.798 |
| CTGF | 4966.956 |
| LOC728809 | 4957.689 |
| RALB | 4949.349 |
| FABP5L2 | 4940.152 |
| NDUFB2 | 4932.081 |
| LOC646483 | 4923.669 |
| GNAI2 | 4916.183 |
| MRPL33 | 4908.738 |
| DDB1 | 4900.69 |
| LOC441073 | 4892.921 |
| LOC649447 | 4885.438 |
| WDR1 | 4877.46 |
| LOC400948 | 4868.795 |
| TIMP1 | 4860.48 |
| LOC402251 | 4852.983 |
| GNB1 | 4845.2 |
| RPL36AL | 4837.16 |
| NOP10 | 4828.969 |
| CHCHD2 | 4821.331 |
| HIST1H4C | 4813.682 |
| FLJ46309 | 4805.906 |
| ANGPT2 | 4798.277 |
| C20orf52 | 4790.903 |
| HOXB5 | 4782.823 |
| NDUFS5 | 4774.766 |
| UQCRQ | 4766.396 |
| LOC402694 | 4758.111 |
| LOC644914 | 4750.406 |
| CXCR4 | 4742.489 |
| WBP2 | 4733.885 |
| COX5B | 4725.663 |
| LOC646630 | 4717.094 |
| PRDX5 | 4704.898 |
| RPS26P11 | 4704.898 |
| NFKBIA | 4694.165 |
| LOC728481 | 4686.756 |
| LOC100128084 | 4679.009 |
| SRGN | 4670.712 |
| LOC645452 | 4663.261 |
| ARHGDIB | 4655.951 |
| SUMO2 | 4648.817 |
| TRAM1 | 4641.106 |
| LDHA | 4633.259 |
| MYH9 | 4625.853 |
| CTGLF7 | 4618.362 |
| LOC388654 | 4611.233 |
| CALM2 | 4604.143 |
| POFUT1 | 4596.614 |
| HDAC1 | 4588.697 |
| ROMO1 | 4581.606 |
| SHANK3 | 4574.51 |
| RPL5 | 4566.714 |
| NDUFAF3 | 4559.808 |
| GSTO1 | 4551.681 |
| SRP9 | 4544.382 |
| CCDC72 | 4537.007 |
| EIF3F | 4529.952 |
| SRGN | 4518.68 |
| RPS6P1 | 4518.68 |
| PFDN5 | 4508.432 |
| SCARB2 | 4500.946 |
| ESAM | 4494.812 |
| HNRNPAB | 4487.656 |
| EGLN2 | 4480.514 |
| LOC401537 | 4473.142 |
| EMP3 | 4466.904 |
| COX5A | 4459.584 |
| SHC1 | 4452.944 |
| LOC648249 | 4445.896 |
| ANXA1 | 4438.55 |
| LOC728428 | 4431.064 |
| COMMD7 | 4424.43 |
| LOC392437 | 4417.459 |
| CSNK1E | 4410.571 |
| GNS | 4403.982 |
| LAMP1 | 4397.37 |
| DNAJA1 | 4390.667 |
| SPARC | 4384.334 |
| SNRPG | 4377.093 |
| RNF7 | 4367.271 |
| LOC729679 | 4367.271 |
| CAP1 | 4356.992 |
| LOC613037 | 4350.417 |
| FAM129B | 4343.163 |
| PRDX5 | 4336.744 |
| SNHG5 | 4330.19 |
| LILRB1 | 4323.835 |
| ATP5J | 4317.569 |
| CCT7 | 4311.306 |
| VDAC3 | 4304.92 |
| GIMAP8 | 4298.598 |
| PTTG1IP | 4291.833 |
| PEA15 | 4285.228 |
| MDK | 4279.023 |
| LOC728672 | 4272.423 |
| LTA4H | 4265.782 |
| ARPC3 | 4259.694 |
| SFRS5 | 4253.734 |
| FABP5 | 4247.866 |
| B2M | 4241.581 |
| JAM3 | 4235.323 |
| ATP5H | 4229.135 |
| ZFAND5 | 4223.899 |
| UBE2E1 | 4217.975 |
| LOC100128266 | 4211.829 |
| NDUFA1 | 4206.047 |
| FKSG30 | 4199.931 |
| TUBB | 4194.265 |
| LOC389168 | 4188.835 |
| C21orf24 | 4182.646 |
| PAM | 4176.248 |

TABLE 1-continued

| Gene symbol | 30-MV2-6 P6, MBA__3877 |
|---|---|
| LOC647340 | 4170.147 |
| ZNF14 | 4164.111 |
| MIF | 4158.17 |
| COX6B1 | 4151.975 |
| NDUFS8 | 4145.751 |
| SF3B14 | 4139.69 |
| LOC389168 | 4132.783 |
| PSMD10 | 4126.234 |
| ATP5H | 4119.575 |
| LOC644315 | 4113.929 |
| LOC643357 | 4107.532 |
| COX8A | 4101.995 |
| HSP90B1 | 4095.739 |
| SAE1 | 4090.083 |
| YWHAB | 4084.048 |
| LOC390345 | 4077.921 |
| RPS26L | 4072.481 |
| SFRS6 | 4066.232 |
| CMTM3 | 4060.137 |
| NDUFB8 | 4054.134 |
| RPL7A | 4048.417 |
| LASP1 | 4042.834 |
| LOC730029 | 4037.351 |
| GSTO1 | 4031.487 |
| HMGN1 | 4026.092 |
| HBXIP | 4020.532 |
| LOC390557 | 4014.99 |
| KLF6 | 4009.341 |
| RTN4 | 4003.429 |
| AP2S1 | 3997.423 |
| TMEM17 | 3991.647 |
| LOC100132795 | 3986.28 |
| DYNLL1 | 3980.465 |
| UBE2D3 | 3973.772 |
| LOC92755 | 3968.05 |
| GPX4 | 3962.772 |
| APLN | 3956.977 |
| LYVE1 | 3951.747 |
| AHNAK | 3946.472 |
| LOC652624 | 3940.562 |
| ATP6V0E1 | 3934.799 |
| EIF4G2 | 3929.242 |
| FAM43A | 3923.254 |
| LOC728873 | 3917.709 |
| PFDN5 | 3912.337 |
| LOC440737 | 3906.923 |
| HNRPM | 3898.701 |
| CYB5B | 3898.701 |
| LOC728126 | 3890.699 |
| RALGDS | 3885.374 |
| GIMAP4 | 3880.145 |
| PPP2CA | 3874.804 |
| CIRBP | 3869.011 |
| C9orf80 | 3863.877 |
| CD34 | 3858.429 |
| ATP6AP1 | 3852.803 |
| MRFAP1 | 3847.485 |
| LOC649821 | 3842.339 |
| EZR | 3837.019 |
| C20orf24 | 3831.573 |
| CD99L2 | 3825.978 |
| AIRE | 3820.74 |
| PSMC1 | 3815.655 |
| C10orf10 | 3810.431 |
| LOC23117 | 3805.025 |
| ATP1A1 | 3799.669 |
| TKT | 3794.411 |
| PSMB7 | 3789.396 |
| JUP | 3784.532 |
| LOC643433 | 3779.673 |
| TMEM66 | 3774.548 |
| PSMC1 | 3769.582 |
| NDUFA3 | 3764.494 |
| MAGED1 | 3759.579 |
| C20orf24 | 3754.453 |
| LOC646785 | 3746.863 |
| LOC653226 | 3746.863 |
| SET | 3739.565 |
| CRIP2 | 3734.717 |
| GLRX5 | 3730.108 |
| LOC100131196 | 3725.29 |
| PGD | 3720.447 |
| TCEB2 | 3715.75 |
| BX537698 | 3711.047 |
| TMEM59 | 3706.181 |
| C8orf37 | 3701.639 |
| ZNF428 | 3696.942 |
| PHLDA1 | 3692.216 |
| TUBA1C | 3687.356 |
| ERP29 | 3682.382 |
| RPL21 | 3677.297 |
| ESM1 | 3672.187 |
| LOC728139 | 3666.905 |
| FAM50A | 3661.865 |
| LAMC1 | 3657.38 |
| UBE2I | 3652.873 |
| ACTR2 | 3648.318 |
| RPS15A | 3643.939 |
| C8orf45 | 3639.256 |
| B4GALT5 | 3635.08 |
| ADD1 | 3628.227 |
| FAM119A | 3628.227 |
| LOC646819 | 3621.287 |
| EIF3B | 3617.007 |
| C6orf48 | 3611.933 |
| HLA-A | 3607.342 |
| ALKBH5 | 3602.68 |
| KHDRBS1 | 3598.262 |
| LOC100134648 | 3593.131 |
| SNRK | 3588.844 |
| MAPRE1 | 3584.246 |
| APP | 3579.695 |
| ATP5F1 | 3574.877 |
| DYNLRB1 | 3570.567 |
| RASIP1 | 3565.849 |
| LOC729926 | 3561.556 |
| CS | 3556.809 |
| NUCKS1 | 3552.277 |
| C20orf100 | 3547.784 |
| SFRS5 | 3543.466 |
| FCGRT | 3539.09 |
| ALDH9A1 | 3534.536 |
| JTB | 3530.451 |
| DCTN2 | 3525.898 |
| FAM127A | 3521.184 |
| EPN1 | 3516.76 |
| LOC402112 | 3512.346 |
| RRAGA | 3507.74 |
| ARHGEF2 | 3503.294 |
| ITGB1 | 3498.718 |
| FKBP1A | 3493.963 |
| NDUFA12 | 3489.713 |
| VEGFB | 3485.396 |
| FEZ2 | 3480.915 |
| FKBP1A | 3476.397 |
| TRMT112 | 3471.984 |
| PRKCH | 3467.297 |
| LOC391370 | 3462.874 |
| RAB11A | 3458.473 |
| S100A16 | 3454.14 |
| ROBLD3 | 3449.96 |
| TALDO1 | 3445.991 |
| RPL22 | 3441.584 |
| LOC644511 | 3437.516 |
| LOC127295 | 3431.188 |
| ANXA2 | 3431.188 |
| ARF4 | 3424.504 |
| AHR | 3420.322 |
| TXNDC5 | 3415.883 |
| LOC646688 | 3411.785 |
| NDUFB3 | 3407.559 |
| AP1S2 | 3403.573 |
| DNAJC8 | 3399.217 |
| SFRS2 | 3394.83 |

TABLE 1-continued

| Gene symbol | 30-MV2-6 P6, MBA__3877 |
|---|---|
| MATR3 | 3390.652 |
| ATP6V0C | 3386.519 |
| C3orf34 | 3382.759 |
| NDUFB3 | 3378.886 |
| LOC728553 | 3374.77 |
| HNRPA2B1 | 3370.461 |
| OCIAD1 | 3366.672 |
| TMEM14C | 3362.56 |
| IGFBP2 | 3358.728 |
| VAMP8 | 3354.294 |
| UQCRFS1 | 3350.384 |
| EIF3D | 3346.006 |
| CTNNA1 | 3341.683 |
| SQLE | 3337.535 |
| TSPAN18 | 3333.603 |
| RNASE1 | 3329.575 |
| CD99 | 3325.701 |
| ATP6V1E1 | 3321.748 |
| OSTC | 3318.133 |
| PRR13 | 3313.96 |
| HNRPA1P4 | 3310.016 |
| LOC440353 | 3306.287 |
| ERGIC3 | 3301.974 |
| C2orf69 | 3297.976 |
| LOC100133477 | 3293.898 |
| LOC728698 | 3289.942 |
| LOC648390 | 3286.072 |
| HK1 | 3282.036 |
| PDHB | 3278.294 |
| FLJ44124 | 3274.603 |
| TUG1 | 3270.77 |
| MORF4L2 | 3266.977 |
| AL15748 | 3263.189 |
| MYADM | 3259.222 |
| DEGS1 | 3255.744 |
| LOC727865 | 3251.966 |
| LOC729236 | 3248.111 |
| LOC158345 | 3244.281 |
| PARK7 | 3240.659 |
| CS | 3236.723 |
| BMS1P5 | 3233.004 |
| LOC390354 | 3229.485 |
| SNRPB2 | 3226.027 |
| PCBP2 | 3222.358 |
| LOC440043 | 3218.805 |
| LOC402175 | 3215.17 |
| TMBIM4 | 3211.304 |
| LOC730004 | 3207.415 |
| LOC374395 | 3203.745 |
| ZDHHC8 | 3200.006 |
| MFNG | 3196.474 |
| AMY1C | 3192.522 |
| VCL | 3188.645 |
| GABARAPL2 | 3185.102 |
| TUBB2B | 3181.562 |
| RCN1 | 3176.229 |
| PTK2 | 3176.229 |
| C14orf173 | 3170.849 |
| LOC399804 | 3166.942 |
| VKORC1 | 3163.391 |
| CCNY | 3159.724 |
| PRNP | 3156.361 |
| PTP4A2 | 3152.617 |
| NDUFB5 | 3148.956 |
| LOC100131801 | 3145.122 |
| NDUFA4 | 3141.587 |
| GAPDH | 3137.906 |
| MRPS21 | 3134.596 |
| HSPD1 | 3131.109 |
| DARS | 3127.618 |
| PLOD1 | 3124.315 |
| LOC347544 | 3120.537 |
| DUXAP3 | 3116.969 |
| POMP | 3113.4 |
| GPIHBP1 | 3109.723 |
| PLS3 | 3106.332 |
| PGK1 | 3101.494 |
| ITPR3 | 3101.494 |
| HIATL2 | 3096.506 |
| ZNF486 | 3092.927 |
| MFSD10 | 3089.188 |
| PON2 | 3085.436 |
| NME1 | 3082.096 |
| LOC731985 | 3078.831 |
| ILF2 | 3075.404 |
| DSTN | 3071.802 |
| SFRS9 | 3068.507 |
| DUSP19 | 3064.885 |
| GHITM | 3061.454 |
| FAM124B | 3057.985 |
| ATP6V1E1 | 3054.703 |
| PTTG1IP | 3051.21 |
| HPCAL1 | 3047.698 |
| ZNF394 | 3042.981 |
| RAB7A | 3042.981 |
| CAV1 | 3037.999 |
| DYNC1LI2 | 3033.362 |
| FASN | 3033.362 |
| PTBP1 | 3028.638 |
| CCDC130 | 3025.44 |
| PSMA4 | 3022.079 |
| HMGN1 | 3018.673 |
| TMED3 | 3015.24 |
| CCT8 | 3011.764 |
| IL10 | 3008.282 |
| LOC645058 | 3005.028 |
| MORF4L1 | 3001.861 |
| SLC44A2 | 2998.583 |
| TMEM123 | 2995.415 |
| MAT2A | 2992.155 |
| ADM | 2988.951 |
| PRND | 2985.625 |
| HNRNPK | 2982.658 |
| NOL7 | 2979.434 |
| YBX1 | 2976.279 |
| LOC391656 | 2973.021 |
| CAMLG | 2969.814 |
| FLNB | 2966.365 |
| ARL6IP1 | 2963.044 |
| LOC399988 | 2959.773 |
| LOC100130562 | 2956.718 |
| RWDD1 | 2953.291 |
| LOC650518 | 2949.922 |
| TCEAL3 | 2947.075 |
| S100A4 | 2944.066 |
| EIF2S3 | 2940.487 |
| PRDX6 | 2937.178 |
| TSPAN9 | 2934.115 |
| GLO1 | 2931.327 |
| PSMD6 | 2928.123 |
| ILK | 2924.745 |
| ACADVL | 2921.625 |
| RHOC | 2918.659 |
| PSME1 | 2915.555 |
| LOC387820 | 2912.308 |
| LDLR | 2909.147 |
| TPM2 | 2904.888 |
| LOC728888 | 2904.888 |
| SEC11A | 2900.347 |
| TEAD2 | 2897.152 |
| SLC25A6 | 2894.058 |
| BTBD2 | 2890.722 |
| NCL | 2887.878 |
| LOC100132391 | 2884.602 |
| RPN1 | 2881.471 |
| TRIM8 | 2878.486 |
| HEXB | 2875.395 |
| ZMAT3 | 2872.252 |
| MGST3 | 2869.117 |
| APP | 2866.02 |
| LOC728244 | 2863.085 |
| ARGLU1 | 2860.002 |
| LEPROT | 2857.123 |
| DDX51 | 2854.073 |

TABLE 1-continued

| Gene symbol | 30-MV2-6 P6, MBA__3877 |
|---|---|
| CXXC5 | 2850.969 |
| AP1S2 | 2847.996 |
| LOC653314 | 2845.126 |
| SRP14P1 | 2842.19 |
| ACP1 | 2838.992 |
| C14orf153 | 2836.086 |
| C20orf30 | 2832.782 |
| UBA1 | 2829.927 |
| SNRPB | 2826.874 |
| TXNIP | 2823.728 |
| NUDT14 | 2820.921 |
| LOC642817 | 2818.102 |
| ATP1B1 | 2815.268 |
| CSNK2B | 2812.341 |
| SNRPF | 2809.605 |
| UXT | 2806.481 |
| EIF3M | 2803.284 |
| ALDOA | 2800.582 |
| EFEMP1 | 2797.68 |
| STAU1 | 2794.503 |
| ANAPC13 | 2791.876 |
| DMC1 | 2788.981 |
| HNRNPH1 | 2785.906 |
| LPP | 2783.35 |
| KRTCAP2 | 2780.536 |
| RPL14L | 2777.793 |
| RPRC1 | 2774.822 |
| DKK3 | 2771.896 |
| BUB3 | 2769.109 |
| CAPZA2 | 2766.271 |
| MGC16121 | 2763.458 |
| EIF4B | 2760.512 |
| MYH10 | 2757.669 |
| LOC100134159 | 2754.867 |
| ARL2 | 2751.979 |
| COLEC12 | 2749.382 |
| RHOJ | 2746.622 |
| LOC401115 | 2743.952 |
| TIMM23 | 2741.358 |
| CARM1 | 2738.743 |
| PJA2 | 2736.055 |
| CMIP | 2733.33 |
| TINP1 | 2730.681 |
| COPA | 2728.078 |
| SSR4 | 2725.157 |
| LOC645688 | 2722.435 |
| PALM | 2719.394 |
| UBE2D3 | 2716.675 |
| TMSL3 | 2714.115 |
| EID2B | 2711.423 |
| TGM2 | 2708.749 |
| P4HB | 2706.261 |
| NAT5 | 2703.492 |
| LOC653079 | 2700.971 |
| STX16 | 2698.241 |
| PUF60 | 2695.483 |
| SEC61B | 2692.776 |
| KLF2 | 2690.108 |
| LOC441506 | 2687.565 |
| PSMA1 | 2684.755 |
| DAPP1 | 2682.076 |
| RAB10 | 2679.581 |
| TIMP2 | 2677.038 |
| NDUFA8 | 2674.402 |
| PRDX5 | 2671.801 |
| PSMA5 | 2668.989 |
| PIGY | 2666.487 |
| PRSS23 | 2663.739 |
| ATP6V1F | 2661.253 |
| C2orf28 | 2658.504 |
| PLS3 | 2655.947 |
| STARD7 | 2653.165 |
| FDFT1 | 2649.481 |
| LOC100130003 | 2649.481 |
| NUP62 | 2645.797 |
| PSMB3 | 2643.409 |
| FAM39E | 2640.664 |
| LOC653505 | 2637.95 |
| TOMM6 | 2635.176 |
| AK095855 | 2631.407 |
| CAPNS1 | 2631.407 |
| LOC649553 | 2627.467 |
| RPL17 | 2625.058 |
| RBX1 | 2622.313 |
| CYBA | 2619.898 |
| ARPC1A | 2617.495 |
| VAMP3 | 2614.954 |
| LOC100133772 | 2612.487 |
| SUMO3 | 2609.9 |
| CD34 | 2607.309 |
| PRMT1 | 2605.064 |
| CD63 | 2602.476 |
| TPI1 | 2599.884 |
| BRI3 | 2597.245 |
| LMNA | 2594.722 |
| SNRNP70 | 2592.098 |
| ID3 | 2589.513 |
| LOC442454 | 2587.179 |
| CAV2 | 2584.557 |
| POLR2G | 2582.077 |
| LOC388707 | 2579.665 |
| ATP6V0E1 | 2577.161 |
| LOC654194 | 2574.714 |
| PHPT1 | 2572.017 |
| POLR2F | 2569.517 |
| APEX1 | 2567.108 |
| EIF3K | 2564.684 |
| LOC653226 | 2562.343 |
| C15orf24 | 2559.838 |
| IMPDH2 | 2557.397 |
| DUSP3 | 2553.815 |
| KPNB1 | 2553.815 |
| NDUFA11 | 2549.928 |
| CTGF | 2547.565 |
| NDUFS4 | 2544.957 |
| BLZF1 | 2542.604 |
| RHEB | 2540.184 |
| PRICKLE4 | 2537.998 |
| PTPLAD1 | 2535.534 |
| HSP90AA1 | 2533.024 |
| BANF1 | 2530.587 |
| COL4A5 | 2528.138 |
| SDCBP | 2525.598 |
| LRRC37B2 | 2523.156 |
| LRRC32 | 2520.757 |
| GSTM1 | 2518.524 |
| TTC3 | 2516.152 |
| DYSF | 2513.921 |
| ETS1 | 2511.662 |
| PON2 | 2509.463 |
| PDCD6 | 2507.209 |
| TOMM20 | 2504.969 |
| REPIN1 | 2502.723 |
| BOLA2 | 2499.166 |
| LOC391126 | 2499.166 |
| SIVA1 | 2495.534 |
| HPRT1 | 2493.245 |
| PRDX3 | 2491.116 |
| CDC16 | 2488.933 |
| ATOX1 | 2486.616 |
| RBM22 | 2484.209 |
| NUAK1 | 2481.962 |
| VPS29 | 2479.728 |
| VDAC1 | 2477.395 |
| EVL | 2475.158 |
| TAGLN2 | 2473.013 |
| LY6E | 2470.802 |
| GPR56 | 2468.456 |
| REEP5 | 2466.211 |
| ZNF69 | 2464.034 |
| LOC728590 | 2461.808 |
| EEF1D | 2459.394 |
| POLR2H | 2457.249 |
| PPP2R1A | 2454.819 |

TABLE 1-continued

| Gene symbol | 30-MV2-6 P6, MBA_3877 |
|---|---|
| PSMB5 | 2452.568 |
| C20orf43 | 2450.369 |
| SPCS1 | 2448.261 |
| ATF4 | 2444.895 |
| EIF4A1 | 2444.895 |
| OSTC | 2441.645 |
| RASGRP3 | 2438.988 |
| LOC100128353 | 2436.823 |
| LOC648024 | 2434.574 |
| EHD4 | 2432.192 |
| VPS26A | 2429.896 |
| ARAP3 | 2427.613 |
| SDHB | 2425.444 |
| RPS6KA2 | 2423.269 |
| MRPS6 | 2420.95 |
| LOC648210 | 2418.767 |
| EIF3G | 2416.711 |
| CNBP | 2414.27 |
| GPR56 | 2412.085 |
| SH2B3 | 2409.804 |
| REXO2 | 2407.484 |
| RNF181 | 2405.349 |
| TSPAN3 | 2403.161 |
| ADCY4 | 2401.073 |
| HNRPUL1 | 2398.99 |
| LOC388339 | 2397.042 |
| DDX3X | 2394.857 |
| GALK1 | 2392.643 |
| PPP1CC | 2390.58 |
| HSP90AB1 | 2388.513 |
| FAM107B | 2386.169 |
| CREB1 | 2384.065 |
| VIL2 | 2381.946 |
| SNRPF | 2379.903 |
| TST | 2377.882 |
| LOC730534 | 2375.733 |
| MKNK2 | 2373.554 |
| STC1 | 2371.352 |
| EIF3I | 2369.413 |
| PPP1R11 | 2367.293 |
| MYLIP | 2365.426 |
| SNRPB | 2363.423 |
| SDCBP | 2361.481 |
| PSMB4 | 2359.383 |
| YY1 | 2357.516 |
| NDUFS3 | 2355.493 |
| H1F0 | 2353.539 |
| THBS1 | 2351.476 |
| SMS | 2349.239 |
| LOC391075 | 2347 |
| ARF1 | 2345.002 |
| ZMIZ1 | 2343.074 |
| RHOG | 2341.097 |
| EIF4H | 2339.187 |
| RAC2 | 2336.985 |
| PPA2 | 2334.924 |
| MSN | 2332.827 |
| RPL23 | 2330.874 |
| ITGB4BP | 2328.691 |
| MYL6B | 2326.759 |
| MFGE8 | 2324.612 |
| ADSL | 2322.313 |
| RPL10A | 2320.322 |
| SHISA5 | 2318.275 |
| SGSM2 | 2316.145 |
| ARL5A | 2314.145 |
| LOC644063 | 2312.122 |
| DHX15 | 2310.085 |
| LOC642956 | 2307.807 |
| DDOST | 2305.894 |
| SDHALP1 | 2303.914 |
| EIF4H | 2302.04 |
| MRPL22 | 2300.216 |
| LOC100132528 | 2298.284 |
| LOC653658 | 2296.237 |
| DYNC1I2 | 2294.276 |
| C20orf30 | 2292.387 |
| HNRNPR | 2290.423 |
| G3BP2 | 2288.484 |
| ZNF682 | 2286.593 |
| PGRMC1 | 2284.582 |
| LOC728492 | 2282.552 |
| BAX | 2280.554 |
| MGC4677 | 2278.547 |
| NNAT | 2276.699 |
| SRRM2 | 2274.895 |
| GUK1 | 2272.81 |
| S100A4 | 2270.843 |
| TMEM14C | 2268.872 |
| TIE1 | 2267.041 |
| IL32 | 2265.217 |
| RPS27 | 2263.252 |
| GSTM2 | 2261.182 |
| SUMF2 | 2259.346 |
| DDT | 2257.489 |
| C20orf199 | 2255.455 |
| ARCN1 | 2253.645 |
| CSNK1G2 | 2251.65 |
| UCHL1 | 2249.632 |
| MDH1 | 2247.564 |
| ARL2BP | 2245.594 |
| TEK | 2243.715 |
| TCEB1 | 2241.851 |
| M6PRBP1 | 2239.955 |
| CAV2 | 2238.078 |
| HYAL2 | 2236.148 |
| PRKCDBP | 2234.444 |
| NUDC | 2232.664 |
| NBPF10 | 2230.705 |
| NDUFA2 | 2228.844 |
| LXN | 2227.013 |
| LOC647000 | 2225.325 |
| C20orf160 | 2223.387 |
| PPM1G | 2220.516 |
| UBL5 | 2220.516 |
| URM1 | 2217.626 |
| VASH1 | 2215.82 |
| XRCC6 | 2213.876 |
| PSMB2 | 2212.134 |
| TCEAL8 | 2210.404 |
| ZNHIT1 | 2208.435 |
| SETD3 | 2206.564 |
| NHP2 | 2204.765 |
| LOC100128288 | 2202.999 |
| SNRK | 2200.977 |
| SDPR | 2199.231 |
| ESYT1 | 2197.376 |
| GDI2 | 2195.532 |
| LOC100130561 | 2193.647 |
| CUTA | 2191.759 |
| GJA4 | 2189.946 |
| SFRS4 | 2187.892 |
| TMED9 | 2186.194 |
| CATSPER2 | 2184.456 |
| RAI14 | 2182.639 |
| PSMD10 | 2180.94 |
| AB074172 | 2179.276 |
| UQCRHL | 2177.506 |
| ARMET | 2175.753 |
| MAP1LC3A | 2173.799 |
| ZNF652 | 2172.067 |
| TPM1 | 2170.117 |
| LMO2 | 2168.384 |
| WDR18 | 2166.626 |
| PODXL | 2164.78 |
| PCMT1 | 2163.02 |
| FERMT2 | 2161.297 |
| SNHG6 | 2158.576 |
| ACLY | 2158.576 |
| TMEM98 | 2155.966 |
| GYPC | 2154.276 |
| HNRNPM | 2152.428 |
| FAM171A1 | 2150.789 |
| PXDN | 2148.125 |

TABLE 1-continued

| Gene symbol | 30-MV2-6 P6, MBA__3877 |
|---|---|
| NGRN | 2148.125 |
| LSM2 | 2145.52 |
| CIB1 | 2143.783 |
| NDUFB7 | 2142.01 |
| ANKS1A | 2140.256 |
| NPTN | 2138.669 |
| EFNB2 | 2137.024 |
| C12orf57 | 2135.199 |
| PRDX4 | 2133.33 |
| BEX4 | 2131.534 |
| RDX | 2129.679 |
| TPM1 | 2128.18 |
| LOC391811 | 2126.614 |
| HNRNPA0 | 2124.898 |
| RAB5B | 2123.318 |
| AARS | 2121.396 |
| RBM10 | 2119.742 |
| CKLF | 2117.921 |
| C15orf63 | 2116.23 |
| ARPC5 | 2114.352 |
| DAB2 | 2112.622 |
| HLX | 2110.92 |
| CD46 | 2109.263 |
| ARHGAP23 | 2107.661 |
| ERH | 2105.924 |
| GLTP | 2104.153 |
| OXA1L | 2102.456 |
| ADAMTS9 | 2100.784 |
| TUBB6 | 2098.927 |
| PRPSAP1 | 2097.122 |
| LOC728533 | 2095.487 |
| CETN2 | 2092.925 |
| COMT | 2092.925 |
| MIR1978 | 2090.444 |
| ATP1B3 | 2088.676 |
| TCF25 | 2086.963 |
| GSPT1 | 2085.414 |
| LOC728031 | 2083.839 |
| HOXB7 | 2082.164 |
| LOC644907 | 2080.516 |
| XPNPEP1 | 2078.884 |
| ZNF22 | 2077.23 |
| DPY30 | 2075.5 |
| LOC653773 | 2073.876 |
| LOC100128410 | 2072.218 |
| CCL14 | 2070.749 |
| LOC648622 | 2069.157 |
| CRCP | 2067.613 |
| COMMD3 | 2066.041 |
| LOC728661 | 2064.404 |
| FEZ2 | 2062.769 |
| QRFPR | 2061.197 |
| CD2BP2 | 2059.596 |
| LOC645138 | 2057.918 |
| ANXA2P1 | 2056.255 |
| ACTN1 | 2054.614 |
| SASH1 | 2052.96 |
| TPM2 | 2051.325 |
| RBM5 | 2049.709 |
| CTSL1 | 2048.076 |
| HSPD1 | 2046.443 |
| LOC728554 | 2044.892 |
| TEK | 2043.162 |
| LOC148430 | 2041.445 |
| CLTA | 2039.745 |
| DDX1 | 2038.117 |
| MGC87895 | 2036.414 |
| ENY2 | 2034.704 |
| C21orf58 | 2033.058 |
| EIF3H | 2031.374 |
| PTOV1 | 2029.659 |
| C19orf10 | 2027.986 |
| NSA2 | 2026.356 |
| SLC2A3 | 2024.764 |
| PRDX3 | 2023.325 |
| GTF2A2 | 2021.712 |
| BCKDK | 2019.916 |
| SPTLC1 | 2018.472 |
| SPCS2 | 2016.07 |
| C17orf61 | 2016.07 |
| C13orf15 | 2013.725 |
| GRAP | 2012.201 |
| TXNDC17 | 2010.558 |
| GLG1 | 2009.077 |
| RING1 | 2007.525 |
| CDC16 | 2005.976 |
| FTHL12 | 2004.417 |
| JMJD8 | 2002.931 |
| DYNLRB1 | 2001.493 |
| LOC730740 | 2000 |
| GTPBP6 | 1998.578 |
| ADAM19 | 1997.024 |
| OCIAD1 | 1995.423 |
| ALPP | 1993.895 |
| LOC645452 | 1992.252 |
| LOC730455 | 1990.712 |
| CIP29 | 1989.102 |
| HDHD1A | 1987.7 |
| PRDX2 | 1986.069 |
| SSU72 | 1984.546 |
| TBCB | 1983.009 |
| UBXN4 | 1981.49 |
| LAMP2 | 1979.835 |
| SOX7 | 1978.374 |
| TSPAN4 | 1977.045 |
| SH3BGRL | 1975.596 |
| JAG2 | 1974.152 |
| LDHB | 1972.673 |
| ANKRD30B | 1971.064 |
| STOML2 | 1969.434 |
| MT2A | 1967.846 |
| CKAP4 | 1966.368 |
| PABPC4 | 1965.115 |
| COX7A2L | 1963.582 |
| BCAP31 | 1962.06 |
| VPS35 | 1960.581 |
| LOC730316 | 1959.032 |
| HSPE1 | 1957.463 |
| DECR1 | 1956.08 |
| NBPF20 | 1954.56 |
| HDAC2 | 1953.03 |
| DYNLT1 | 1951.625 |
| MTPN | 1950.182 |
| ATP5E | 1948.728 |
| CLCN7 | 1947.253 |
| KDELR1 | 1944.949 |
| GARS | 1944.949 |
| FNTA | 1941.981 |
| NME4 | 1941.981 |
| ADAR | 1939.685 |
| SS18L2 | 1938.165 |
| SNHG7 | 1936.806 |
| CLIC4 | 1935.304 |
| MRPL22 | 1933.809 |
| PLIN2 | 1932.481 |
| NDEL1 | 1930.949 |
| LOC100131531 | 1929.469 |
| BC036485 | 1928.086 |
| UNC84B | 1926.666 |
| SEC61A1 | 1925.247 |
| PPP2R2A | 1923.752 |
| CCT2 | 1922.433 |
| HGS | 1921.051 |
| RNASEK | 1919.6 |
| EIF4A3 | 1918.241 |
| TUBB2C | 1916.747 |
| APEX1 | 1915.376 |
| CCND3 | 1913.884 |
| RPAIN | 1912.433 |
| LOC729841 | 1911.051 |
| UNC50 | 1909.61 |
| RPP21 | 1908.262 |
| LZTR1 | 1907.012 |
| ABCA1 | 1905.602 |

TABLE 1-continued

| Gene symbol | 30-MV2-6 P6, MBA_3877 |
|---|---|
| NDUFV2 | 1904.214 |
| TAF15 | 1902.111 |
| F2R | 1902.111 |
| GSTK1 | 1900.015 |
| LSM1 | 1898.52 |
| GRK5 | 1897.066 |
| RPS23 | 1895.565 |
| RPLP0 | 1894.206 |
| SRPX | 1892.791 |
| SRP14 | 1891.423 |
| LOC642590 | 1890.132 |
| MRPL51 | 1888.738 |
| MTSS1 | 1887.426 |
| SPG7 | 1886.074 |
| ETFA | 1884.622 |
| NCSTN | 1883.33 |
| ARS2 | 1882.034 |
| LOC90586 | 1880.692 |
| TPD52L2 | 1879.422 |
| RHBDF1 | 1878.106 |
| MAPK3 | 1876.805 |
| RSL24D1 | 1875.555 |
| PIN1 | 1874.261 |
| CTSB | 1872.918 |
| CCDC90B | 1871.493 |
| NAP1L4 | 1870.159 |
| ATP9A | 1868.852 |
| EVI1 | 1866.765 |
| POLR1D | 1866.765 |
| SSTR1 | 1864.751 |
| PCID2 | 1863.457 |
| HIGD1A | 1861.98 |
| MGC10997 | 1860.583 |
| STRAP | 1859.285 |
| MRPL36 | 1857.963 |
| ARHGEF7 | 1856.522 |
| ATP5D | 1855.212 |
| NR2F2 | 1853.965 |
| FNBP1 | 1852.702 |
| LMBRD1 | 1851.216 |
| LOC392437 | 1849.863 |
| DNAJB11 | 1847.944 |
| ELTD1 | 1847.944 |
| ZNF358 | 1846.034 |
| PPP6C | 1844.683 |
| LOC646567 | 1843.41 |
| GOLGA7 | 1842.093 |
| ID1 | 1840.693 |
| UBXN1 | 1839.336 |
| IPO11 | 1838.036 |
| TNFRSF10B | 1836.729 |
| C7orf59 | 1835.465 |
| SYT11 | 1834.199 |
| OSTF1 | 1832.859 |
| ZNHIT3 | 1831.481 |
| GOT2 | 1828.835 |
| LOC399748 | 1827.599 |
| HSBP1 | 1826.317 |
| EFNA1 | 1825.115 |
| IDH1 | 1823.88 |
| HNRPK | 1822.669 |
| ANGPTL2 | 1821.346 |
| HOXB8 | 1820.111 |
| TMEM85 | 1818.718 |
| SIAH1 | 1817.475 |
| LOC285741 | 1816.02 |
| CFDP1 | 1814.757 |
| LOC652489 | 1813.434 |
| BANP | 1812.163 |
| C2orf25 | 1810.833 |
| ARHGAP17 | 1809.513 |
| SMS | 1808.21 |
| ATP6V1G1 | 1806.998 |
| TMED2 | 1805.879 |
| CTDSP2 | 1804.656 |
| PPP2CB | 1803.45 |
| PSMD4 | 1802.198 |
| FKBP14 | 1800.996 |
| LUZP1 | 1799.739 |
| CTSL1 | 1798.517 |
| GLCE | 1797.266 |
| DCTPP1 | 1795.899 |
| PCNP | 1794.674 |
| MRPL37 | 1793.311 |
| SSBP1 | 1792.031 |
| BZW2 | 1790.698 |
| GLB1 | 1789.417 |
| STOM | 1788.173 |
| ZYX | 1786.884 |
| EIF5A | 1785.669 |
| NUMB | 1784.498 |
| PSMD7 | 1783.367 |
| FXR1 | 1782.152 |
| PARP4 | 1780.857 |
| RARS | 1779.561 |
| RBMS1 | 1778.275 |
| FAM175A | 1776.427 |
| SF3B1 | 1776.427 |
| LOC100128936 | 1774.579 |
| LOC644191 | 1773.38 |
| CHRNA5 | 1772.196 |
| EIF2AK1 | 1771.002 |
| MGC71993 | 1769.83 |
| LOC255167 | 1768.607 |
| CAB39 | 1767.443 |
| FGD5 | 1766.278 |
| HNRPR | 1765.174 |
| RPS26 | 1763.91 |
| TAX1BP3 | 1762.65 |
| PSMC5 | 1761.404 |
| LOC642755 | 1760.256 |
| LOC202781 | 1758.944 |
| DKK3 | 1757.831 |
| ZMYND11 | 1756.637 |
| C19orf70 | 1755.48 |
| SVIL | 1754.196 |
| SELS | 1753.02 |
| NDUFB11 | 1751.891 |
| CPNE3 | 1750.703 |
| MRI1 | 1749.53 |
| LOC401397 | 1748.318 |
| TPRG1L | 1747.141 |
| VAT1 | 1746.025 |
| TNFRSF1B | 1744.824 |
| C5orf28 | 1743.673 |
| NOSIP | 1742.474 |
| FER1L3 | 1741.29 |
| RPS28 | 1740.056 |
| TCEAL4 | 1738.878 |
| FAHD1 | 1737.738 |
| PQLC1 | 1736.625 |
| ATP6V1A | 1734.904 |
| TAX1BP1 | 1734.904 |
| WDR6 | 1733.152 |
| GPS1 | 1731.944 |
| DAB2 | 1730.771 |
| LOC338870 | 1729.516 |
| HNRNPM | 1728.303 |
| PUM1 | 1727.184 |
| SLC9A1 | 1725.915 |
| TRMT5 | 1724.831 |
| ATP1B1 | 1723.685 |
| EMD | 1722.585 |
| PSMG2 | 1720.345 |
| CCDC23 | 1720.345 |
| C20orf24 | 1720.345 |
| UROD | 1718.176 |
| PPP2R2B | 1717.048 |
| COPB1 | 1715.868 |
| PUM1 | 1714.76 |
| CASP2 | 1713.646 |
| TFG | 1712.523 |
| LOC728820 | 1711.473 |
| CHCHD9 | 1710.374 |

TABLE 1-continued

| Gene symbol | 30-MV2-6 P6, MBA_3877 |
|---|---|
| CSE1L | 1709.265 |
| LOC100131785 | 1708.063 |
| FAM120A | 1706.955 |
| TMEM111 | 1705.855 |
| HMGN2 | 1704.702 |
| TNK2 | 1703.603 |
| PTPRF | 1702.506 |
| C19orf56 | 1701.464 |
| C1orf85 | 1700.401 |
| CLDND1 | 1699.33 |
| SF3B5 | 1698.141 |
| CCDC56 | 1696.976 |
| HIGD2A | 1695.904 |
| SRP54 | 1694.673 |
| MRPS18C | 1693.505 |
| SLC38A2 | 1692.344 |
| SYPL1 | 1691.19 |
| PWP1 | 1690.03 |
| CYC1 | 1688.812 |
| VPS28 | 1687.69 |
| BSG | 1686.67 |
| TRIOBP | 1685.549 |
| IDH3B | 1684.483 |
| FAM65A | 1683.363 |
| IMP3 | 1682.299 |
| SCRN1 | 1681.224 |
| PLOD3 | 1680.136 |
| TSC22D1 | 1679.005 |
| UCKL1 | 1677.916 |
| C3orf54 | 1676.807 |
| TCEAL3 | 1675.69 |
| ZRANB2 | 1674.65 |
| SFRS18 | 1673.475 |
| PSMC2 | 1672.436 |
| TMEM147 | 1671.356 |
| CNDP2 | 1670.377 |
| BAT1 | 1669.32 |
| PSMD4 | 1667.617 |
| SYPL1 | 1667.617 |
| FAM96A | 1666.04 |
| PFDN1 | 1664.983 |
| MRPS12 | 1663.866 |
| MXD4 | 1662.821 |
| PSMA6 | 1661.627 |
| LOC729279 | 1660.481 |
| LRP10 | 1659.336 |
| MRPL17 | 1658.299 |
| WSB1 | 1657.178 |
| ARL6IP5 | 1656.15 |
| HSD17B7 | 1655.049 |
| CYP1A1 | 1654.03 |
| RGL1 | 1653.014 |
| ARHGDIA | 1651.931 |
| LSM3 | 1650.846 |
| LOC440359 | 1649.8 |
| LOC730744 | 1648.793 |
| SFRS14 | 1647.759 |
| LOC653566 | 1646.763 |
| LOC651894 | 1645.664 |
| CLDND1 | 1644.57 |
| PTDSS1 | 1643.545 |
| SSB | 1642.473 |
| GRIPAP1 | 1641.337 |
| RRAS | 1640.329 |
| PRPF8 | 1639.153 |
| CRTAP | 1638.192 |
| AV737317 | 1637.094 |
| PDIA5 | 1635.993 |
| GYPC | 1634.996 |
| LOC653086 | 1633.937 |
| SULT1A1 | 1632.887 |
| EXOSC10 | 1631.823 |
| SEC14L1 | 1630.73 |
| CMTM7 | 1629.708 |
| CDK4 | 1628.643 |
| SLC12A2 | 1627.639 |
| LOC100128062 | 1626.109 |
| DUSP22 | 1626.109 |
| LOC100129379 | 1624.099 |
| TMEM158 | 1624.099 |
| SH3GLB1 | 1622.482 |
| TGFBR3 | 1621.398 |
| SFRS1 | 1620.42 |
| C1QBP | 1619.375 |
| MMS19L | 1618.318 |
| FABP4 | 1617.363 |
| SYF2 | 1615.805 |
| LOC647285 | 1615.805 |
| POM121C | 1614.33 |
| CTXN1 | 1613.323 |
| PMP22 | 1612.342 |
| DCTN3 | 1611.336 |
| EI24 | 1610.259 |
| SNURF | 1609.211 |
| PFKP | 1608.135 |
| AK3 | 1607.133 |
| NAP1L1 | 1606.141 |
| PSMB10 | 1605.125 |
| FIS1 | 1604.15 |
| RCN2 | 1603.109 |
| COPS5 | 1602.015 |
| UBE1 | 1600.951 |
| METAP2 | 1599.995 |
| DEGS1 | 1598.954 |
| TPP1 | 1597.891 |
| TCF4 | 1596.551 |
| PLD3 | 1596.551 |
| SLC20A1 | 1595.085 |
| BRD2 | 1593.958 |
| GTF2E2 | 1592.892 |
| CARHSP1 | 1591.833 |
| KIAA1949 | 1590.829 |
| PSMF1 | 1589.926 |
| DCTN1 | 1588.867 |
| LOC643668 | 1587.862 |
| C11orf59 | 1586.41 |
| CDC42EP4 | 1586.41 |
| LOC729317 | 1584.87 |
| ATXN2 | 1584.024 |
| ZDHHC16 | 1582.96 |
| KLHL3 | 1581.971 |
| FBXO11 | 1581.021 |
| HSD17B12 | 1579.986 |
| WDR54 | 1578.996 |
| THOC7 | 1578.022 |
| LOC286157 | 1577.048 |
| PGAM1 | 1576.049 |
| RRBP1 | 1575.086 |
| COPS3 | 1574.042 |
| TGOLN2 | 1572.574 |
| ATP5J2 | 1572.574 |
| PAICS | 1571.114 |
| MYCT1 | 1570.123 |
| CCNG1 | 1569.125 |
| EIF1B | 1568.22 |
| PTPLAD1 | 1567.188 |
| GLUD1 | 1566.225 |
| SRRM1 | 1565.277 |
| BCL2L1 | 1564.333 |
| SDHAF2 | 1563.342 |
| TMEM126B | 1562.454 |
| COX6A1 | 1561.487 |
| LOC651198 | 1560.508 |
| TSC22D3 | 1559.555 |
| ACAT1 | 1558.552 |
| LOC389787 | 1557.626 |
| RALY | 1556.622 |
| SSR2 | 1555.669 |
| MTUS1 | 1554.711 |
| RNF144 | 1553.795 |
| LOC100132727 | 1552.848 |
| JUN | 1551.928 |
| NDUFAB1 | 1550.977 |
| MCM3 | 1550.039 |

TABLE 1-continued

| Gene symbol | 30-MV2-6 P6, MBA_3877 |
|---|---|
| MRFAP1L1 | 1549.157 |
| PRNP | 1548.212 |
| COL18A1 | 1547.275 |
| ECH1 | 1546.324 |
| LOC650369 | 1545.353 |
| CDC42EP5 | 1543.892 |
| ZNF738 | 1543.892 |
| HSPA9 | 1542.471 |
| KCTD12 | 1541.497 |
| SUZ12 | 1540.117 |
| RABGAP1 | 1540.117 |
| GTF2H5 | 1538.645 |
| DDA1 | 1537.81 |
| BIN1 | 1536.906 |
| DUSP1 | 1535.978 |
| STK24 | 1535.023 |
| ITGA5 | 1534.085 |
| DDX47 | 1533.17 |
| SEC31A | 1532.248 |
| PNPT1 | 1531.378 |
| SPTBN1 | 1530.478 |
| GPSM1 | 1529.602 |
| EXOC7 | 1528.681 |
| PSMC6 | 1527.768 |
| GTPBP4 | 1526.921 |
| DBN1 | 1525.956 |
| GLT25D1 | 1525.037 |
| EIF2A | 1523.676 |
| LIMCH1 | 1523.676 |
| CCNDBP1 | 1522.32 |
| TROVE2 | 1521.457 |
| RPS26L | 1520.508 |
| AURKAIP1 | 1519.568 |
| WBP5 | 1518.619 |
| RPAIN | 1517.721 |
| TPM3 | 1516.876 |
| KIAA1671 | 1516.034 |
| LOC653994 | 1515.152 |
| DBNL | 1514.297 |
| NTAN1 | 1513.386 |
| BOLA2 | 1512.461 |
| TMEM44 | 1511.551 |
| EDN1 | 1510.177 |
| ITGB1BP1 | 1510.177 |
| CCDC109B | 1508.421 |
| ZNF22 | 1508.421 |
| C4orf18 | 1507.078 |
| APOA1BP | 1506.23 |
| SH3BGRL3 | 1505.32 |
| UBE2M | 1504.415 |
| CAPNS1 | 1503.518 |
| SPOP | 1502.701 |
| GNG10 | 1501.888 |
| PLSCR4 | 1500.944 |
| TMEM181 | 1500.131 |
| LOC388275 | 1499.324 |
| FEZ1 | 1498.408 |
| COX17 | 1497.494 |
| LMNA | 1496.663 |
| C21orf33 | 1495.672 |
| ITM2C | 1494.223 |
| DNMT1 | 1494.223 |
| ITM2C | 1492.824 |
| PRR14 | 1492.013 |
| CYR61 | 1491.16 |
| BNIP3 | 1490.33 |
| IGF2R | 1489.489 |
| SON | 1488.169 |
| GFOD1 | 1488.169 |
| LOC641700 | 1486.891 |
| MRI1 | 1486.039 |
| PROCR | 1485.086 |
| LOC732007 | 1484.229 |
| CTTN | 1483.402 |
| LOC644799 | 1482.539 |
| RUSC1 | 1481.565 |
| GRN | 1480.712 |
| ITGB5 | 1479.823 |
| GYG1 | 1478.946 |
| MRPL23 | 1478.119 |
| ASAP1 | 1477.166 |
| KPNA4 | 1476.338 |
| PSME2 | 1475.46 |
| PRAGMIN | 1474.691 |
| RCC2 | 1473.898 |
| INPP1 | 1472.989 |
| LOC100132291 | 1472.102 |
| NHP2L1 | 1471.226 |
| ANAPC11 | 1470.023 |
| CGNL1 | 1470.023 |
| NFATC2IP | 1468.795 |
| IARS2 | 1467.883 |
| TJP1 | 1467.001 |
| LOC729768 | 1466.205 |
| ATP6V1B2 | 1465.338 |
| LOC644774 | 1464.489 |
| CSF2RA | 1463.664 |
| ANGPT2 | 1462.786 |
| ATP5J2 | 1462.035 |
| ANAPC5 | 1461.197 |
| BRMS1 | 1460.376 |
| ADRM1 | 1459.571 |
| C2orf28 | 1458.684 |
| DGUOK | 1457.91 |
| SLC25A39 | 1456.678 |
| CHCHD10 | 1456.678 |
| DGUOK | 1455.463 |
| PEBP1 | 1454.59 |
| PPP1R14B | 1453.763 |
| TMEM205 | 1453.072 |
| GNL2 | 1452.202 |
| LOC646723 | 1451.384 |
| BCLAF1 | 1450.526 |
| PAPSS2 | 1449.722 |
| ROD1 | 1448.848 |
| C8orf59 | 1448.044 |
| CLNS1A | 1447.207 |
| TAX1BP1 | 1446.445 |
| BNIP3L | 1445.532 |
| NFKB1 | 1444.768 |
| LOC644934 | 1443.99 |
| ADAM15 | 1443.15 |
| PPP1CA | 1442.281 |
| C17orf49 | 1441.421 |
| CGGBP1 | 1440.555 |
| AP3B1 | 1439.754 |
| ARPC4 | 1439.019 |
| TMEM87A | 1438.202 |
| LOC440093 | 1437.389 |
| PRDX2 | 1436.503 |
| CENPB | 1435.284 |
| RIOK3 | 1435.284 |
| PEPD | 1434.051 |
| C7orf30 | 1433.277 |
| SF3B4 | 1432.503 |
| C7orf50 | 1431.741 |
| PAICS | 1430.9 |
| DHRS7 | 1430.109 |
| SCHIP1 | 1429.311 |
| SMARCA4 | 1428.443 |
| LOC391833 | 1427.659 |
| CD151 | 1426.918 |
| C14orf112 | 1426.134 |
| CCT3 | 1425.327 |
| TSPAN17 | 1424.433 |
| HEBP1 | 1423.707 |
| PALMD | 1422.87 |
| PSMA3 | 1422.059 |
| HCFC1R1 | 1420.912 |
| FAM96B | 1420.912 |
| LOC728532 | 1419.695 |
| TRAPPC2L | 1418.904 |
| BASP1 | 1418.075 |
| ZFYVE21 | 1416.821 |

TABLE 1-continued

| Gene symbol | 30-MV2-6 P6, MBA__3877 |
|---|---|
| EDF1 | 1416.821 |
| TMEM43 | 1415.619 |
| KIAA1191 | 1414.827 |
| COMMD1 | 1414.003 |
| VEZF1 | 1413.213 |
| TMCO1 | 1412.417 |
| PSMD6 | 1411.674 |
| PAFAH1B3 | 1410.928 |
| C19orf43 | 1410.128 |
| CWC15 | 1409.341 |
| PHB2 | 1408.51 |
| FAM45A | 1407.765 |
| SPTLC1 | 1407.045 |
| C2orf29 | 1406.196 |
| PGLS | 1405.486 |
| GNPDA1 | 1404.659 |
| AIDA | 1403.945 |
| FNBP1L | 1403.256 |
| TCEAL8 | 1402.467 |
| WFS1 | 1401.669 |
| CYTSA | 1400.85 |
| IFNGR2 | 1400.118 |
| MRPS24 | 1399.314 |
| SASH1 | 1398.612 |
| LOC728590 | 1397.854 |
| LSM5 | 1397.054 |
| NDUFB10 | 1396.327 |
| PTPRM | 1395.602 |
| BIN1 | 1394.867 |
| MLLT11 | 1394.156 |
| KLHL5 | 1393.377 |
| CAMK2N1 | 1392.62 |
| IFI16 | 1391.929 |
| RAB2B | 1391.157 |
| TSG101 | 1390.367 |
| ARHGAP21 | 1389.62 |
| TXNL2 | 1388.918 |
| EIF2B4 | 1388.222 |
| AKR7A2 | 1387.016 |
| PPP4C | 1387.016 |
| MARCH7 | 1385.806 |
| EWSR1 | 1385.086 |
| MGEA5 | 1383.891 |
| JMJD8 | 1383.891 |
| TSPAN3 | 1382.76 |
| FAM62B | 1381.996 |
| PLVAP | 1381.302 |
| ATP1B1 | 1380.575 |
| LOC220433 | 1379.767 |
| KIAA1751 | 1378.533 |
| NOX4 | 1378.533 |
| BCAT1 | 1377.397 |
| TRAPPC5 | 1376.299 |
| DIABLO | 1376.299 |
| ATG4A | 1375.226 |
| EWSR1 | 1374.548 |
| LOC100130919 | 1373.854 |
| EIF6 | 1373.121 |
| SERF1B | 1372.435 |
| C2orf25 | 1371.71 |
| ISCU | 1370.6 |
| EMCN | 1370.6 |
| NAE1 | 1369.468 |
| CBX2 | 1368.713 |
| GTF3A | 1367.917 |
| FXYD5 | 1367.183 |
| RNU6-1 | 1366.377 |
| CIAO1 | 1365.645 |
| SF3A2 | 1364.954 |
| LOC729217 | 1364.264 |
| SMARCD1 | 1363.514 |
| YPEL5 | 1362.416 |
| MAT2B | 1362.416 |
| CD9 | 1361.367 |
| CLK1 | 1360.635 |
| SHE | 1359.905 |
| ARPC4 | 1359.19 |

TABLE 1-continued

| Gene symbol | 30-MV2-6 P6, MBA__3877 |
|---|---|
| ENG | 1358.525 |
| DPM1 | 1357.848 |
| RPS26L | 1356.814 |
| SEC24C | 1356.814 |
| WDFY1 | 1355.688 |
| ABCF1 | 1354.999 |
| SEPN1 | 1354.331 |
| CTPS2 | 1353.527 |
| JAK1 | 1352.825 |
| IGF2BP2 | 1352.016 |
| CALU | 1351.325 |
| NSUN2 | 1350.603 |
| ETS2 | 1349.889 |
| PSMA4 | 1349.159 |
| NOTCH4 | 1348.37 |
| PPIL3 | 1347.714 |
| EBPL | 1346.925 |
| UBE2A | 1346.266 |
| TMEM14D | 1345.427 |
| TSPO | 1344.7 |
| UBE2E3 | 1344.022 |
| SNX17 | 1343.293 |
| AHCY | 1342.54 |
| APH1A | 1341.847 |
| CTTN | 1341.154 |
| SH3GLB2 | 1340.142 |
| LOC646347 | 1340.142 |
| TUBB3 | 1339.084 |
| LSM4 | 1338.417 |
| MCM7 | 1337.661 |
| UBE2G2 | 1336.937 |
| CCL15 | 1336.199 |
| VPS37C | 1335.507 |
| MRPL43 | 1334.784 |
| AKT1 | 1334.044 |
| TSC22D1 | 1333.376 |
| GLRX3 | 1332.713 |
| C3orf21 | 1332.065 |
| UFC1 | 1331.382 |
| DDEF2 | 1330.627 |
| HNRPDL | 1329.926 |
| OAT | 1329.173 |
| SAMM50 | 1328.509 |
| DDX42 | 1327.8 |
| TMEM189-UBE2V1 | 1327.136 |
| BRD9 | 1326.459 |
| TRABD | 1325.811 |
| LYN | 1325.106 |
| LOC100130516 | 1324.409 |
| UBAP2L | 1323.751 |
| LYL1 | 1323.043 |
| NAT5 | 1322.032 |
| C19orf43 | 1322.032 |
| C22orf13 | 1320.994 |
| PAFAH1B1 | 1320.273 |
| HECW2 | 1319.607 |
| DDX39 | 1318.904 |
| NSMCE4A | 1318.229 |
| NRP1 | 1317.531 |
| NLRP8 | 1316.868 |
| IFFO1 | 1316.188 |
| SERPINH1 | 1315.531 |
| TOMM20 | 1314.873 |
| SLC35B1 | 1314.205 |
| BMP6 | 1313.502 |
| ACTR10 | 1312.85 |
| AIMP2 | 1312.181 |
| PLRG1 | 1311.423 |
| TUBB6 | 1310.078 |
| SWAP70 | 1310.078 |
| LOC345041 | 1310.078 |
| PPA1 | 1308.715 |
| CUTA | 1308.027 |
| MAGT1 | 1307.382 |
| LOC388621 | 1306.728 |
| TSPO | 1306.076 |
| CKLF | 1305.451 |

TABLE 1-continued

| Gene symbol | 30-MV2-6 P6, MBA__3877 |
|---|---|
| ACTR1A | 1304.807 |
| HSPA1B | 1304.1 |
| DYNLRB1 | 1303.429 |
| LOC651149 | 1302.787 |
| TINF2 | 1302.134 |
| ACTL6A | 1301.494 |
| CNIH4 | 1300.809 |
| NECAP2 | 1300.112 |
| AKT1 | 1299.402 |
| FLOT1 | 1298.767 |
| C6orf153 | 1298.085 |
| CUEDC2 | 1297.413 |
| AK90694 | 1296.433 |
| LOC728903 | 1296.433 |
| TXNRD1 | 1295.501 |
| AFAP1L1 | 1294.547 |
| CAPN11 | 1294.547 |
| UBE2L6 | 1293.604 |
| KIAA0355 | 1292.622 |
| LAPTM4B | 1292.622 |
| RNU6-15 | 1291.31 |
| TGFB1I1 | 1291.31 |
| TNFRSF21 | 1290.303 |
| HNRNPAB | 1289.261 |
| C14orf166 | 1289.261 |
| C3orf10 | 1288.225 |
| MAPK3 | 1287.591 |
| BUD31 | 1286.944 |
| CCDC50 | 1286.227 |
| DPM1 | 1285.552 |
| TSEN34 | 1284.894 |
| FAM32A | 1284.298 |
| PTGR1 | 1283.698 |
| BTBD6 | 1283.024 |
| COQ5 | 1282.389 |
| DNAJA2 | 1281.734 |
| YTHDC1 | 1281.127 |
| CXCR4 | 1280.516 |
| SNCA | 1279.908 |
| C19orf53 | 1279.337 |
| TMED10P | 1278.664 |
| PIP5K2B | 1278.034 |
| CTDSPL | 1277.381 |
| CSE1L | 1276.724 |
| LOC728973 | 1276.059 |
| ITM2A | 1275.44 |
| SEPT15 | 1274.779 |
| DERA | 1274.102 |
| THOC4 | 1273.114 |
| SNRPN | 1273.114 |
| ATG12 | 1272.123 |
| SUPT16H | 1271.505 |
| NINJ1 | 1270.853 |
| TRAF3IP2 | 1270.277 |
| LOC100132247 | 1269.647 |
| MMP1 | 1269.005 |
| GPN1 | 1268.349 |
| C16orf61 | 1267.703 |
| ZFP91 | 1267.065 |
| CLTA | 1266.103 |
| RBM3 | 1266.103 |
| STK25 | 1265.098 |
| CD99L2 | 1264.439 |
| SEMA3E | 1263.804 |
| MMRN1 | 1263.233 |
| FAM38A | 1262.61 |
| CXXC5 | 1261.953 |
| FAM125A | 1261.062 |
| COPE | 1261.062 |
| CNRIP1 | 1260.09 |
| NDUFB6 | 1259.195 |
| AKR1A1 | 1259.195 |
| ATP2B4 | 1257.931 |
| SF3A3 | 1257.931 |
| ACSS2 | 1256.642 |
| SGSH | 1256.642 |
| MRPL32 | 1255.638 |
| FBLN1 | 1254.976 |
| CKAP5 | 1254.373 |
| PPP1R15A | 1253.721 |
| PCDHB2 | 1253.122 |
| FBXO21 | 1252.554 |
| TMEM183B | 1251.959 |
| TYK2 | 1251.349 |
| EIF2B4 | 1250.723 |
| KIAA1310 | 1250.124 |
| UBE3C | 1249.545 |
| ZNF207 | 1248.609 |
| TOMM22 | 1248.609 |
| AP2M1 | 1247.656 |
| RBM9 | 1247.018 |
| NAGK | 1246.158 |
| SIVA | 1246.158 |
| PGAM4 | 1245.267 |
| BRPF1 | 1244.707 |
| LOC653232 | 1244.138 |
| MRPL24 | 1243.487 |
| ITPRIPL2 | 1242.837 |
| RANBP1 | 1242.19 |
| PIR | 1241.579 |
| NDUFS7 | 1241.024 |
| MRPL33 | 1240.402 |
| LOC731777 | 1239.449 |
| ACSL3 | 1239.449 |
| SYNCRIP | 1238.21 |
| SCAMP1 | 1238.21 |
| HSPH1 | 1237.276 |
| SNORD13 | 1236.367 |
| ATP5C1 | 1236.367 |
| RNPS1 | 1235.512 |
| YRDC | 1234.929 |
| FNBP4 | 1234.016 |
| SLC27A3 | 1234.016 |
| SNTB2 | 1233.115 |
| AK2 | 1232.525 |
| C9orf78 | 1231.887 |
| SHROOM4 | 1231.273 |
| CHMP5 | 1230.644 |
| KLHDC3 | 1229.734 |
| COL5A2 | 1229.734 |
| MKRN1 | 1228.856 |
| CLPTM1L | 1228.232 |
| FZD4 | 1227.591 |
| AHCYL1 | 1226.997 |
| C11orf2 | 1226.102 |
| TCEA2 | 1226.102 |
| SERTAD2 | 1225.225 |
| ZNF581 | 1224.638 |
| TXNRD1 | 1224.021 |
| MRPS22 | 1223.439 |
| COPB2 | 1222.825 |
| EIF2B2 | 1222.166 |
| MPDZ | 1221.614 |
| RABAC1 | 1220.997 |
| LRRFIP1 | 1220.45 |
| CCT7 | 1219.851 |
| LOC643336 | 1219.27 |
| EIF4E2 | 1218.658 |
| SNRNP70 | 1218.084 |
| UNC45A | 1217.535 |
| EPRS | 1216.981 |
| LOC653147 | 1216.359 |
| EIF4G2 | 1215.815 |
| CHIC2 | 1215.238 |
| RALY | 1214.672 |
| COMMD4 | 1214.132 |
| HAGH | 1213.555 |
| ATIC | 1212.981 |
| SEMA6A | 1212.362 |
| SDAD1 | 1211.776 |
| TMEM173 | 1211.176 |
| WDR61 | 1210.555 |
| UQCRC1 | 1209.94 |
| ERGIC3 | 1209.292 |

TABLE 1-continued

| Gene symbol | 30-MV2-6 P6, MBA__3877 |
|---|---|
| C16orf58 | 1208.466 |
| FTHL12 | 1208.466 |
| TIGA1 | 1207.301 |
| ITGB5 | 1207.301 |
| ATP2B4 | 1206.435 |
| HSPC268 | 1205.868 |
| ACP5 | 1205.3 |
| CHST7 | 1204.734 |
| LOC728643 | 1204.165 |
| TMEM93 | 1203.577 |
| RNF5P1 | 1203.002 |
| IMMT | 1202.47 |
| NOP56 | 1201.878 |
| STX5 | 1201.322 |
| TXNDC5 | 1200.716 |
| LOC100131905 | 1200.21 |
| PLEKHM2 | 1199.673 |
| LSM7 | 1199.112 |
| SPRY1 | 1198.584 |
| C19orf60 | 1198.021 |
| LSM14A | 1197.449 |
| SRP54 | 1196.849 |
| AMZ2 | 1196.268 |
| FKBP9L | 1195.389 |
| RAB8A | 1195.389 |
| SPSB3 | 1194.239 |
| GIPC1 | 1194.239 |
| SLC29A1 | 1193.425 |
| MRPL3 | 1192.832 |
| CNIH | 1192.266 |
| FAM127B | 1191.741 |
| ATP6V0B | 1191.148 |
| ATP1B3 | 1190.628 |
| IDH3B | 1190.099 |
| TFDP1 | 1189.245 |
| TECR | 1189.245 |
| GAR1 | 1188.402 |
| CDR2L | 1187.799 |
| KIAA1147 | 1187.189 |
| IGFBP7 | 1186.642 |
| HRASLS3 | 1186.117 |
| PFN2 | 1185.528 |
| RPL7L1 | 1184.957 |
| TDP1 | 1184.364 |
| RASA1 | 1183.793 |
| BMS1 | 1183.25 |
| DRAP1 | 1182.717 |
| POLE3 | 1182.185 |
| NARF | 1181.617 |
| EBNA1BP2 | 1181.081 |
| LOC644563 | 1180.512 |
| HECTD1 | 1179.933 |
| ATG4A | 1179.092 |
| IRAK1 | 1179.092 |
| CCDC92 | 1178.273 |
| SNRPA1 | 1177.46 |
| CAPZB | 1177.46 |
| SCAMP3 | 1176.606 |
| LOC642975 | 1176.084 |
| CNIH | 1175.454 |
| TRAPPC4 | 1174.829 |
| NISCH | 1174.275 |
| ADARB1 | 1173.705 |
| ECHS1 | 1173.163 |
| GSN | 1172.576 |
| GOLGA3 | 1171.965 |
| TMEM183A | 1171.472 |
| PREI3 | 1170.618 |
| COPZ1 | 1170.618 |
| RNF149 | 1169.794 |
| PRKRIR | 1169.219 |
| KLHL9 | 1168.706 |
| RPL9 | 1168.134 |
| ANKRD9 | 1167.583 |
| MRPL14 | 1167.011 |
| CCBE1 | 1166.449 |
| VBP1 | 1165.62 |
| LAMB1 | 1165.62 |
| C12orf10 | 1164.491 |
| MRPS10 | 1164.491 |
| TWSG1 | 1163.691 |
| LOC100132585 | 1163.139 |
| MED6 | 1162.643 |
| GAK | 1162.143 |
| HPS6 | 1161.618 |
| SOX4 | 1161.072 |
| CLSTN1 | 1160.531 |
| TAF1C | 1159.974 |
| LIMS1 | 1159.434 |
| TRIM44 | 1158.63 |
| TNPO2 | 1158.63 |
| CHMP1B | 1157.806 |
| ATP5G1 | 1157.298 |
| TUBG1 | 1156.749 |
| NDUFV1 | 1156.212 |
| MAP2K1 | 1155.693 |
| NOTCH1 | 1155.126 |
| UBE2F | 1154.596 |
| POLR2I | 1154.025 |
| RSL1D1 | 1153.5 |
| MRPL21 | 1152.919 |
| LOC648695 | 1152.101 |
| POLR2J3 | 1152.101 |
| DNAJB6 | 1151.286 |
| TMEM131 | 1150.796 |
| CHMP5 | 1150.222 |
| UNC84A | 1149.634 |
| FAM84B | 1149.095 |
| SOX7 | 1148.576 |
| NEDD8 | 1148.045 |
| CRELD2 | 1147.203 |
| EEF2K | 1147.203 |
| SH2D3C | 1146.37 |
| ACSS2 | 1145.794 |
| CNIH | 1145.304 |
| RPL13 | 1144.794 |
| ARF4 | 1144.238 |
| ASAP2 | 1143.712 |
| HCFC1 | 1143.163 |
| SLC41A3 | 1142.617 |
| ARID1A | 1142.087 |
| MRPL54 | 1141.562 |
| SNRPB2 | 1140.987 |
| PAIP2 | 1140.448 |
| ULK1 | 1139.961 |
| CALD1 | 1139.447 |
| MAPBPIP | 1138.939 |
| HARS | 1138.45 |
| HCLS1 | 1137.98 |
| SFRS17A | 1137.448 |
| ASH2L | 1136.926 |
| LOC441131 | 1136.194 |
| AIF1L | 1136.194 |
| METAP1 | 1135.416 |
| TTC37 | 1134.883 |
| RNASET2 | 1134.356 |
| CARD10 | 1133.855 |
| ATP5SL | 1133.309 |
| CTSC | 1132.787 |
| GDPD5 | 1132.295 |
| C5orf15 | 1131.76 |
| C1orf123 | 1131.216 |
| MED28 | 1130.738 |
| ADD3 | 1130.209 |
| HES4 | 1129.346 |
| VPS28 | 1129.346 |
| SIRPA | 1128.332 |
| PPP1R16B | 1128.332 |
| ATP1A1 | 1127.569 |
| TOP2B | 1127.102 |
| CLDN14 | 1126.581 |
| BRIX1 | 1126.127 |
| GLRX | 1125.649 |
| PHRF1 | 1125.135 |

TABLE 1-continued

| Gene symbol | 30-MV2-6 P6, MBA__3877 |
|---|---|
| ANXA7 | 1124.618 |
| PEX11B | 1124.07 |
| LOC390466 | 1123.317 |
| FTHL8 | 1123.317 |
| RBM4 | 1122.305 |
| ACO1 | 1122.305 |
| FAF2 | 1121.286 |
| ZSCAN18 | 1121.286 |
| USO1 | 1120.278 |
| PDCD4 | 1120.278 |
| BOLA3 | 1119.499 |
| GIMAP6 | 1118.759 |
| EXOSC1 | 1118.759 |
| TNPO1 | 1117.953 |
| MRPL21 | 1117.431 |
| ETF1 | 1116.964 |
| TMEM109 | 1116.22 |
| PICALM | 1116.22 |
| PPP2R5E | 1115.468 |
| DHX15 | 1115.038 |
| RANGAP1 | 1114.519 |
| NUAK1 | 1114.015 |
| RAPGEF1 | 1113.275 |
| C1orf43 | 1113.275 |
| FAM38B | 1112.526 |
| ATP1B3 | 1111.986 |
| AW276479 | 1111.51 |
| CNPY2 | 1111.025 |
| CORO1B | 1110.552 |
| AV737943 | 1110.036 |
| ARL6IP6 | 1109.565 |
| SRF | 1109.065 |
| GALNT11 | 1108.587 |
| DIMT1L | 1108.078 |
| SEC14L1 | 1107.615 |
| PTS | 1107.107 |
| PHF5A | 1106.657 |
| NIPA2 | 1106.208 |
| LOC728564 | 1105.495 |
| LOC728666 | 1105.495 |
| CCM2 | 1104.829 |
| PLDN | 1104.368 |
| TMEM189 | 1103.863 |
| LOC647302 | 1103.405 |
| ACOT9 | 1102.912 |
| EHD1 | 1102.392 |
| TMEM88 | 1101.651 |
| RIOK3 | 1101.651 |
| CHMP2A | 1100.961 |
| LOC729495 | 1100.251 |
| LOC100129211 | 1100.251 |
| C11orf74 | 1099.23 |
| DHRS4 | 1099.23 |
| ALDH7A1 | 1098.483 |
| RYBP | 1098.015 |
| CISD1 | 1097.296 |
| NCBP2 | 1097.296 |
| PLCG1 | 1096.586 |
| FBXW11 | 1096.097 |
| LAMP2 | 1095.627 |
| C11orf67 | 1095.123 |
| TXLNA | 1094.675 |
| ST13 | 1094.182 |
| ASNSD1 | 1093.703 |
| THAP11 | 1093.181 |
| SCYL1 | 1092.677 |
| C20orf20 | 1092.201 |
| ANKRD11 | 1091.664 |
| KIAA0494 | 1090.984 |
| ATP6V1D | 1090.984 |
| MAGED1 | 1090.273 |
| TIA1 | 1089.785 |
| HPRT1 | 1089.321 |
| C1orf128 | 1088.849 |
| STIP1 | 1088.359 |
| LAPTM4B | 1087.642 |
| MED16 | 1087.642 |
| SLC16A3 | 1086.895 |
| EFCAB4A | 1086.425 |
| ERAL1 | 1085.952 |
| AKR1B1 | 1085.496 |
| GLIPR2 | 1085.028 |
| SNRPC | 1084.522 |
| SLC41A3 | 1084.067 |
| C12orf35 | 1083.54 |
| SMTN | 1083.064 |
| SCAP | 1082.62 |
| UBAC1 | 1082.171 |
| CLINT1 | 1081.704 |
| TNFRSF25 | 1081.222 |
| MRPL45 | 1080.789 |
| C4orf32 | 1080.313 |
| LOC100128196 | 1079.856 |
| CHFR | 1079.43 |
| FUBP3 | 1078.945 |
| FLJ35390 | 1078.417 |
| ARSD | 1077.77 |
| IMPDH1 | 1077.77 |
| TSPAN6 | 1077.097 |
| GLB1 | 1076.624 |
| SFRS2IP | 1076.142 |
| RHOJ | 1075.704 |
| TIMM22 | 1075.007 |
| ARAP3 | 1075.007 |
| MYC | 1074.047 |
| PRICKLE1 | 1074.047 |
| LOC728620 | 1073.366 |
| ZNF467 | 1072.903 |
| FAM160B1 | 1072.44 |
| PRPF31 | 1071.962 |
| LOC100129742 | 1071.49 |
| FOXO1 | 1071.02 |
| P4HA2 | 1070.563 |
| C19orf2 | 1070.108 |
| XLKD1 | 1069.626 |
| NOS3 | 1069.22 |
| FXYD5 | 1068.745 |
| RAB32 | 1068.311 |
| CPNE1 | 1067.883 |
| ARPC1B | 1067.446 |
| LOC729406 | 1067.012 |
| LSM3 | 1066.554 |
| MYOF | 1066.106 |
| POGK | 1065.674 |
| SFRS2B | 1065.215 |
| GPR137 | 1064.777 |
| FAM189B | 1064.313 |
| TOMM40 | 1063.822 |
| CRK | 1063.404 |
| DSTN | 1062.951 |
| UGP2 | 1062.271 |
| ORMDL1 | 1062.271 |
| LOC653566 | 1061.591 |
| RBMX | 1061.134 |
| ASAP1 | 1060.679 |
| CDC25B | 1059.996 |
| UTP11L | 1059.996 |
| U2AF2 | 1059.358 |
| ARF5 | 1058.938 |
| ERCC1 | 1058.498 |
| VGLL4 | 1058.016 |
| CREB3L2 | 1057.327 |
| NSL1 | 1057.327 |
| AKR1A1 | 1056.706 |
| NUDT5 | 1056.246 |
| UBQLN1 | 1055.836 |
| VPS41 | 1055.356 |
| PDIA6 | 1054.718 |
| LOC100133516 | 1054.718 |
| PELO | 1054.057 |
| LACTB | 1053.587 |
| XRCC2 | 1053.146 |
| HIGD1A | 1052.714 |
| SEC22C | 1052.285 |

TABLE 1-continued

| Gene symbol | 30-MV2-6 P6, MBA_3877 |
|---|---|
| CARD8 | 1051.832 |
| MAP1B | 1051.378 |
| DRG1 | 1050.899 |
| STMN1 | 1050.489 |
| LOC440345 | 1050.027 |
| DCAF7 | 1049.575 |
| BOLA3 | 1049.18 |
| APRT | 1048.483 |
| ZDHHC9 | 1048.483 |
| SFT2D1 | 1047.81 |
| ZNF207 | 1047.343 |
| FLJ36131 | 1046.928 |
| C6orf125 | 1046.454 |
| YIPF3 | 1045.998 |
| LOC729992 | 1045.539 |
| IGF2BP3 | 1045.127 |
| TM9SF2 | 1044.687 |
| DCTN6 | 1044.225 |
| FXR1 | 1043.764 |
| RPL34 | 1043.313 |
| AP2M1 | 1042.912 |
| LOC644330 | 1042.479 |
| TXNDC12 | 1042.033 |
| BEX1 | 1041.572 |
| PGM1 | 1041.145 |
| NRBP2 | 1040.679 |
| IRF2BP2 | 1040.249 |
| ITFG1 | 1039.802 |
| MRPL20 | 1039.355 |
| MRPS17 | 1038.91 |
| FAM3A | 1038.477 |
| MAN2B2 | 1037.795 |
| S100A13 | 1037.795 |
| PTPN11 | 1037.141 |
| NPEPL1 | 1036.503 |
| DPAGT1 | 1036.503 |
| STUB1 | 1035.88 |
| CDK5RAP3 | 1035.203 |
| LOC100128266 | 1035.203 |
| LRRC41 | 1034.576 |
| RPS21 | 1034.106 |
| PIAS4 | 1033.669 |
| CHP | 1033.24 |
| CPSF4 | 1032.79 |
| FRMD4A | 1032.13 |
| CDK10 | 1032.13 |
| LOC650157 | 1031.44 |
| LOC100132717 | 1030.745 |
| G6PD | 1030.745 |
| UROS | 1030.116 |
| BC035081 | 1029.698 |
| LOC730255 | 1029.265 |
| ENPP2 | 1028.837 |
| CNN2 | 1028.433 |
| OSBPL9 | 1027.99 |
| TRPT1 | 1027.561 |
| RN7SK | 1027.133 |
| COPS7A | 1026.742 |
| NHP2 | 1026.284 |
| PAPSS1 | 1025.863 |
| MACF1 | 1025.215 |
| ACOT7 | 1025.215 |
| SERINC3 | 1024.519 |
| LAMA4 | 1024.067 |
| MRPS15 | 1023.652 |
| TM9SF4 | 1023.053 |
| ACAT2 | 1023.053 |
| LOC645166 | 1022.43 |
| NCOA7 | 1022.016 |
| TBC1D4 | 1021.59 |
| RHOQ | 1021.206 |
| FAM39DP | 1020.8 |
| TNFRSF1A | 1020.394 |
| FKBP5 | 1019.963 |
| FAM120B | 1019.554 |
| LCMT1 | 1019.166 |
| CCDC59 | 1018.55 |
| AK022936 | 1018.55 |
| RPUSD4 | 1017.934 |
| IGFBP3 | 1017.538 |
| SLC35E1 | 1017.154 |
| CCDC125 | 1016.336 |
| RIN2 | 1016.336 |
| MBTPS1 | 1016.336 |
| TMEM126B | 1015.509 |
| GPR177 | 1015.087 |
| LOC728661 | 1014.67 |
| XPO1 | 1014.219 |
| ATG4B | 1013.813 |
| DAP3 | 1013.397 |
| CISD1 | 1012.933 |
| STK19 | 1012.524 |
| AES | 1011.867 |
| NDUFA13 | 1011.867 |
| NDRG4 | 1011.251 |
| FIBP | 1010.835 |
| VHL | 1010.439 |
| RNF38 | 1009.799 |
| PRMT1 | 1009.799 |
| VPS4B | 1009.162 |
| SHMT2 | 1008.756 |
| MRPL34 | 1008.353 |
| OCIAD2 | 1007.943 |
| PSMD1 | 1007.326 |
| HSD17B4 | 1007.326 |
| VBP1 | 1006.484 |
| MCRS1 | 1006.484 |
| TNFAIP1 | 1005.872 |
| TNRC6B | 1005.446 |
| COASY | 1005.033 |
| ST3GAL1 | 1004.617 |
| RHBDD2 | 1003.993 |
| SURF4 | 1003.993 |
| KLHDC8B | 1003.384 |
| TSPAN4 | 1002.961 |
| KDM5B | 1002.552 |
| STK4 | 1002.151 |
| LPHN2 | 1001.764 |
| POLR2A | 1001.35 |
| CD59 | 1000.938 |
| DNAL4 | 1000.492 |
| RHBDF2 | 1000.062 |

The 30-MV2-6 cells were maintained in EGM-MV2 media (PromoCell) plus TGFβ inhibitor (SB43154) (Cayman Chemical Co., Ann Arbor, Mich.) in a 5% $CO_2$, 5% $O_2$ humidified cell culture incubator. The 30-MV2-6 cells were seeded at a density of 40 k/cm$^2$. The culture media was removed and after two washes with phosphate buffered saline (PBS), (PBS) was added at 0.1 ml/cm$^2$ to produce conditioned medium from which exosomes were isolated. Alternatively, basal EGM-MV2 medium (PromoCell, Heidelberg, Germany) without fetal calf serum or growth factor additives was substituted for PBS. The media was conditioned by the cells in a humidified tissue culture incubator for 16 hours at 37° C. at 5% $CO_2$ and 1% $O_2$. The conditioned medium was collected and 0.5 volumes of Total Exosome Isolation Reagent (Life Technologies) was added and mixed well by vortexing until there was a homogenous solution. Alternatively, a solution of 15% polyethylene glycol (Hampton Research, Aliso Viejo, Calif.), 1.5 M NaCl (Sigma, St Louis, Mo.) was substituted for the Total Exosome Isolation Reagent. The sample was incubated at 4° C. for at least 16 hours to precipitate the exosomes, followed by centrifugation at 10,000×g for 1 hour at 4° C. The supernatant was removed and the pellet is resuspended in 0.01 volume of PBS.

Exosome particle size and concentration were measured using nanoparticle tracking analysis (NTA; Nanosight, Malvern Instrument, Ltd, Malvern Worcestershire, UK) and by ELISA. The experiments were repeated using commercially available HT1080 cells (ATCC) as a comparison. HT1080 cells are a human fibrosarcoma cell line known to form exosomes with vesicle forming ability (see, e.g. Kim et al. (2002) *Cancer Res.* 62:6312).

The results of the Nanosight NTA (triplicates) for exosome preparations derived from 30-MV2-6 and HT1080 cells (ATCC, Manassas, Va.) are shown in FIG. 1. The results indicate that particles prepared from 30-MV2-6 are from 80 to 110 nm with predominant peak at 88 nm+/−2.9 nm. The particles prepared from a HT1080 human fibrosarcoma cells were larger by comparison with a mode of 120 nm+/−7.4 nm. The concentration of exosomes bearing the exosome marker CD63 was measured by ELISA, using samples of known concentrations of HT1080 exosomes as a standard curve. Samples were adsorbed to the ELISA plate by incubation overnight in PBS. The PBS was removed and wells were washed 3 times in ELISA wash buffer (Thermo Scientific, Waltham, Mass.) followed by incubation with primary anti-CD63 antibody (BD Pharmingen, Franklin Lakes, N.J.) for 1 hour at room temperature. The primary antibody was removed followed by washing 3 times in wash buffer and incubation with secondary antibody (HRP conjugated anti-mouse) (Invitrogen, Grand Island, N.Y.)) at 1:3000 dilution for 1 hour at room temperature. The wells were washed 3 additional times with wash buffer and incubated in Super sensitive TMB ELISA substrate (Sigma, St Louis, Mo.) for 0.5 hour followed by addition of ELISA stop solution (InVitrogen, Grand Island, N.Y.). The concentration of exosomes was determined by reading optical density in a standard plate reader at wavelength of 450 nm.

Example 2: Angiogenic Activity of Exosomes Prepared from a Human Embryonic Progenitor Cell Line Angiogenic activity of exosomes was assayed using an in-vitro endothelial tube forming assay. The assay was performed in triplicate in a µ well slide (Ibidi, Verona, Wis.) or in single wells of a 96-well plate. The wells were coated with reduced growth factor Matrigel (BD, Franklin Lakes, N.J.). Human umbilical cord vascular endothelial cells (HUVEC) that were grown to 70-80% confluence were plated at 5000-7000 cells per well in a µ well slide in 50 ul of EGM-MV2 basal medium (Promocell, Heidelberg, Germany) (no supplements) containing up to 10 µl of exosomes in PBS or equivalent volume of PBS without exosomes as a negative control or in 50 µl of complete EGM-MV2 medium with growth factor supplements as a positive control. Alternatively, the assay was performed in a 96-well plate using 60,000 to 90,000 cells per well in 280 µl of medium and 20 µl of exosomes or PBS. The cells are incubated at 37° C. in a 5% CO2 incubator for 16-18 hours. The cells were photographed under phase contrast at low power or stained with calcein and photographed using a fluorescence microscope. The images were scored for cell covered area, total tube length, number of branch points, and number of loops using Wimasis image analysis (Ibidi, Verona, Wis.). At least 3 random images were quantified per well.

Figure 2B:
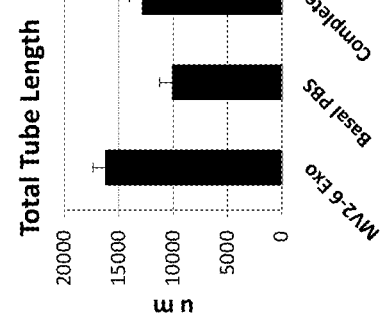
FIG. 2B is a graph quantifying four parameters: cell covered area; total tube length; total number of branching points and total number of loops in HUVECs grown in the presence of exosomes isolated from human embryonic progenitor cell line 30-MV2-6 ("MV2-6 EXO"); HUVECs grown in basal media +PBS, but without exposure to exosomes isolated from human embryonic progenitor cell line 30-MV2-6 ("Basal PBS"); and HUVECs grown in complete media, but without exposure to exosomes isolated from human embryonic progenitor cell line 30-MV2-6 ("Complete").
Figure 2B:
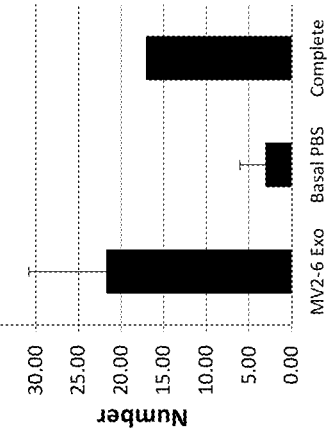
Figure 2B:
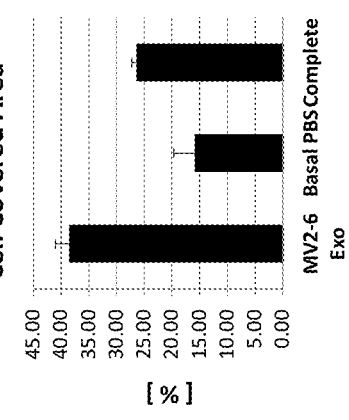
Figure 2B:
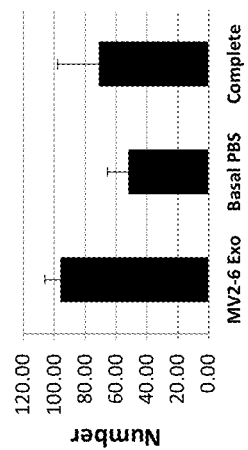
Figure 2A:
FIG. 2A shows three photomicrographs, the first showing the effects on vascular tube like formation in HUVECs grown in the presence of basal media supplemented with exosomes isolated from human embryonic progenitor cell line 30-MV2-6 (top); the second showing the effects on vascular tube formation in HUVECs grown in base media supplemented with PBS, but without exposure to exosomes isolated from human embryonic progenitor cell line 30-MV-2-6 (middle); and the third showing the effects on vascular tube like formation in HUVECs grown in complete medium, but without exposure to exosomes isolated from human embryonic progenitor cell line 30-MV2-6 (bottom).
Figure 2A:

FIG. 2A shows an increase in HUVEC endothelial tube formation when grown in the presence of 30-MV2-6 derived exosomes (in PBS) compared to basal medium with an equivalent amount of PBS (with no exosomes) added (negative control). The quantified results (FIG. 2B) indicate that total tube length, cell covered area, branch points and the number of loops were all increased by the addition of exosomes compared to basal medium indicating that the 30-MV2-6 exosomes are angiogenic.

Figure 3B:
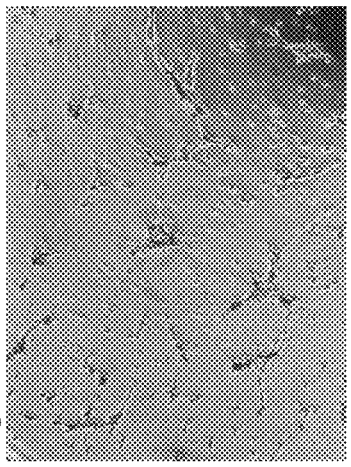
FIG. 3B is a photomicrograph showing that hES derived perivascular cells form incomplete tubes when cultured in EGM-MV2 basal media.
Figure 3A:
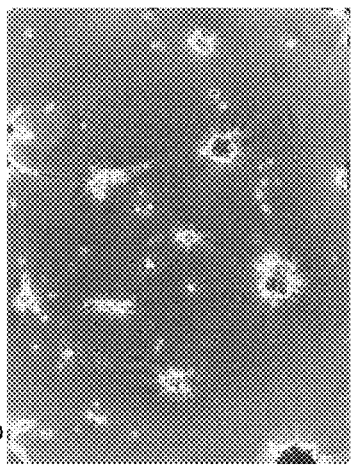
FIG. 3A is photomicrograph showing that hES derived perivascular cells form aggregates when cultured in the presence of complete EGM-MV2 media with serum and growth factors.
Figure 3E:
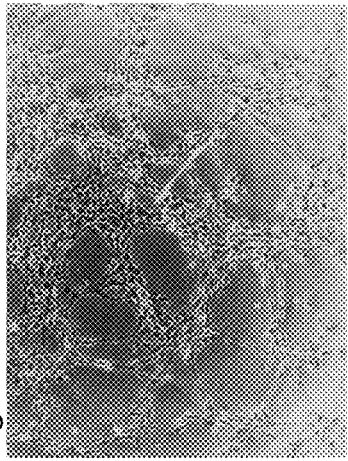
FIGS. 3C-E are photomicrographs showing that increasing doses of exosomes isolated from the human clonal endothelial progenitor cell line 30-MV2-6 resulted in increasing tube formation in hES derived perivascular cells.
Figure 3D:
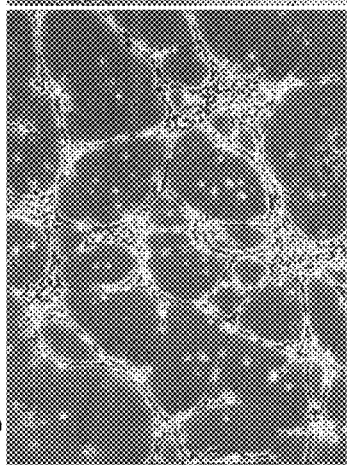
Figure 3C:
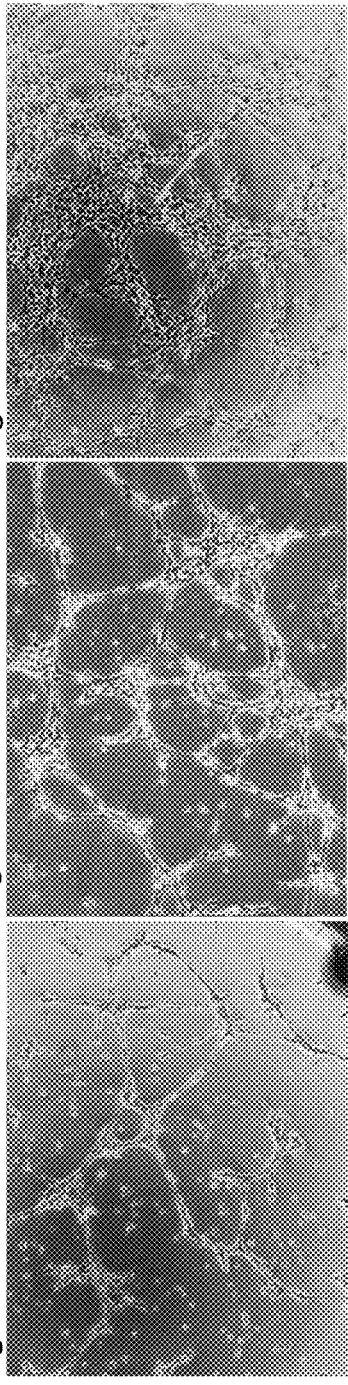
Figure 3G:
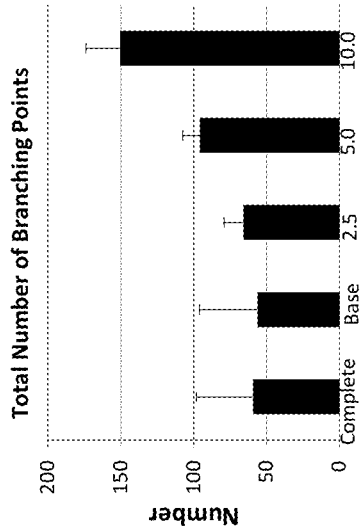
FIG. 3G is a graph showing the total number of branching points in hES derived perivascular cells grown either in complete media (complete); basal media (base) or basal media supplemented with increasing doses ($2.5 \times 10^7$, $5.0 \times 10^7$, $10.0 \times 10^7$) of exosomes isolated from the human clonal endothelial progenitor cell line 30-MV2-6.
Figure 3I:
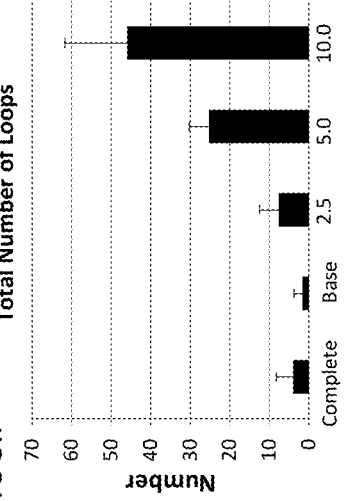
FIG. 3I is a graph showing the total number of loops formed by hES derived perivascular cells grown either in complete media (complete); basal media (base) or basal media supplement with increasing doses ($2.5 \times 10^7$, $5.0 \times 10^7$, $10.0 \times 10^7$) of exosomes isolated from the human clonal endothelial progenitor cell line 30-MV2-6.
Figure 3F:
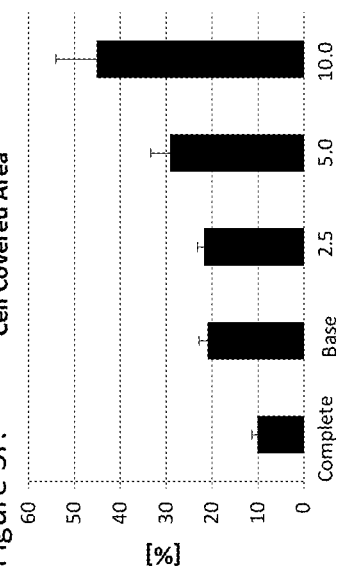
FIG. 3F is a graph showing the cell covered area of hES derived perivascular cells grown either in complete media (complete); basal media (base) or basal media supplemented with increasing doses ($2.5 \times 10^7$, $5.0 \times 10^7$, $10.0 \times 10^7$) of exosomes isolated from the human clonal endothelial progenitor cell line 30-MV2-6.
Figure 3H:
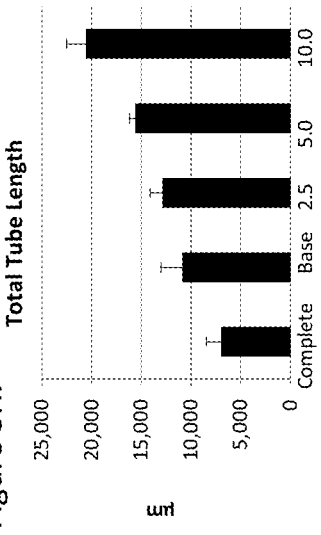
FIG. 3H is a graph showing the total tube length of vascular tube like structures formed by hES derived perivascular cells grown either in complete media (complete); basal media (base) or basal media supplemented with increasing doses ($2.5 \times 10^7$, $5.0 \times 10^7$, $10.0 \times 10^7$) of exosomes isolated from the human clonal endothelial progenitor cell line 30-MV2-6.

Angiogenic activity of exosomes was also assessed by their ability to stimulate in vitro tube formation using human embryonic stem (hES) cell derived perivascular embryonic progenitor cells (PEPCs) (also called 017-PC-A) cells bearing pericyte and stemness markers (CD146, CD133, Podoplanin)(U.S. patent application Ser. No. 14/625,621, filed on Feb. 18, 2015). The assay was performed as described for HUVECs except that hES cell derived PEPCs were used instead of HUVECs. The assay was performed in triplicate using µ well slides (Ibidi, Verona, Wis.). The hES pericytes that were grown in defined medium differ from HUVECs in their response to complete medium. HUVECs respond to complete EGM-MV2 medium in the tube forming assay with robust tube formation (FIG. 2A). In contrast, hES PEPCs migrate to form foci consisting of cellular aggregates (FIG. 3A) when grown on Matrigel in complete EGM-MV2 medium and thus exhibited reduced tube formation. The hES PEPCs grown in defined medium form incomplete tubes (FIG. 3B) similar to HUVEC in basal medium (FIG. 2A). Like HUVECs, the hES PEPCs grown in the presence of 30-MV2-6 exosomes displayed an increase in tube formation as shown in FIG. 3C-3E. The tube formation was dose responsive and quantitative analysis indicated an increase in all 4 tube formation parameters (FIG. 3F-3I). Unlike HUVECs which respond to both exosomes and complete medium with increased tube formation, hES derived PEPCs respond to exosomes with increased tube formation but respond to complete medium with reduced tube formation compared to basal medium. Thus, 30-MV2-6 exosomes induce angiogenesis in a non-angiogenic cell type that does not respond to the angiogenic factors present in EGM-MV2 complete medium. These data indicate that 30-MV2-6 derived exosomes do not simply mimic the factors in complete medium but instead are capable of stimulating hES derived PEPC tube formation by a mechanism that is distinct from the action of complete medium on these cells.

Example 3: Comparison of Angiogenic Activity of Exosomes Derived from a Human Embryonic Progenitor Cell Line and Exosomes Derived from Adult Bone Marrow-Derived Mesenchymal Stem Cells (BM-MSCs)

Exosomes were prepared from an embryonic stem cell derived PureStem® cell line, 30-MV2-6, and from adult bone marrow-derived mesenchymal stem cells (BM-MSCs) from two different commercial sources (Lonza and Promocell), according to methods described in Example 1. The angiogenic activity was assessed using the in vitro endothelial tube formation assay described in Example 2. Briefly, the exosomes ($2 \times 10^8$ particles/50 µl) were incubated with human umbilical cord vascular endothelial (HUVEC) cells for 12-16 hours on low growth factor Matrigel using a µ-well slide (Ibidi, Verona, Wis.). Tube length was assessed by image capture and analyzed using Angiogenesis Analyzer in ImageJ (http://rsb.info.nih.gov/ij/) image processing program. Total tube length formed per image/µ-well was calculated relative to total tube length formed for HUVEC in complete EGM-MV2 medium (CM) containing angiogenic growth factors (VEGF and FGF2) and fetal bovine serum (FBS).

Figure 4:
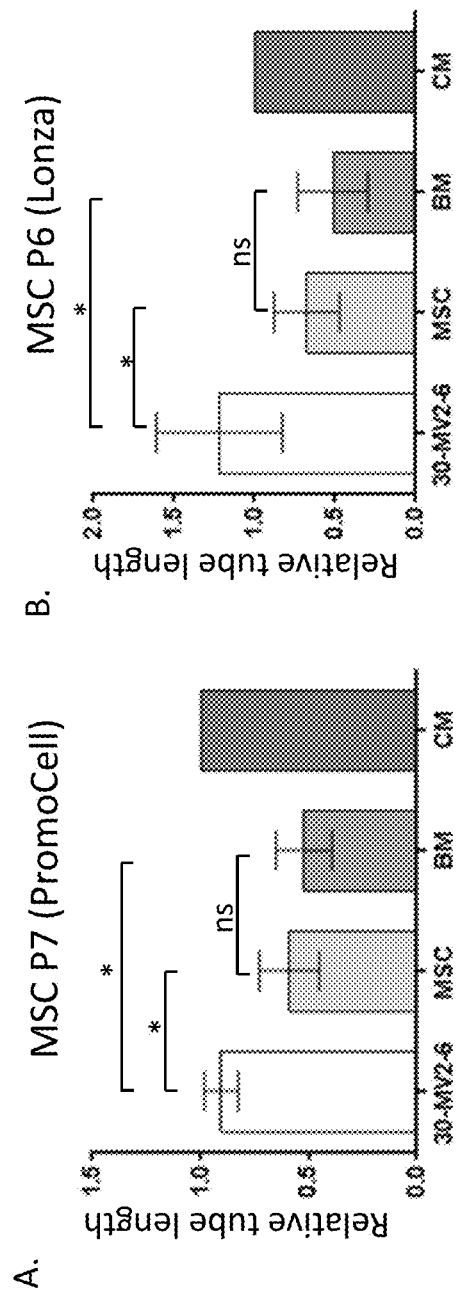
FIG. 4 shows comparison of in vitro angiogenic activity of exosomes isolated from the human clonal endothelial cell line 30-MV2-6 versus exosomes isolated from bone marrow mesenchymal stem cells (BM-MSC). Two different commercially available sources of BM-MSCs were used, Promocell (panel A) and Lonza (panel B). 30-MV2-6: exosomes derived from 30-MV2-6 cell line; MSC: exosomes derived from BM-MSC; BM: basal medium, negative control; CM: complete growth medium. Results were normalized to tube length obtained using complete growth medium (CM).

Exosomes derived from the 30-MV2-6 cell line were compared to early passage BM-MSCs from the two different sources, Promocell (Heidelberg, Germany) (FIG. 4, panel A) and from Lonza (Basel, Switzerland) (FIG. 4, panel B). In both cases the angiogenic activity of 30-MV2-6 derived exosomes was greater than the angiogenic activity of BM-MSC derived exosomes. The total tube length of HUVECs incubated in basal medium with 30-MV2-6 derived exosomes (in PBS) was similar to HUVECs incubated in complete EGM-MV2 medium and significantly greater than BM-MSC derived exosomes (from either source) or HUVEC incubated in basal EGM-MV2 medium and PBS alone. The total tube length resulting from BM-MSC derived exosomes was on average slightly higher than PBS in basal medium (BM) but the difference was not statistically significant ($p<0.05$). These results indicate that embryonic endothelial progenitor stem cell line derived exosomes are advantageous over adult BM-MSC derived exosomes for inducing angiogenic activity in endothelial cells.

Figure 5:
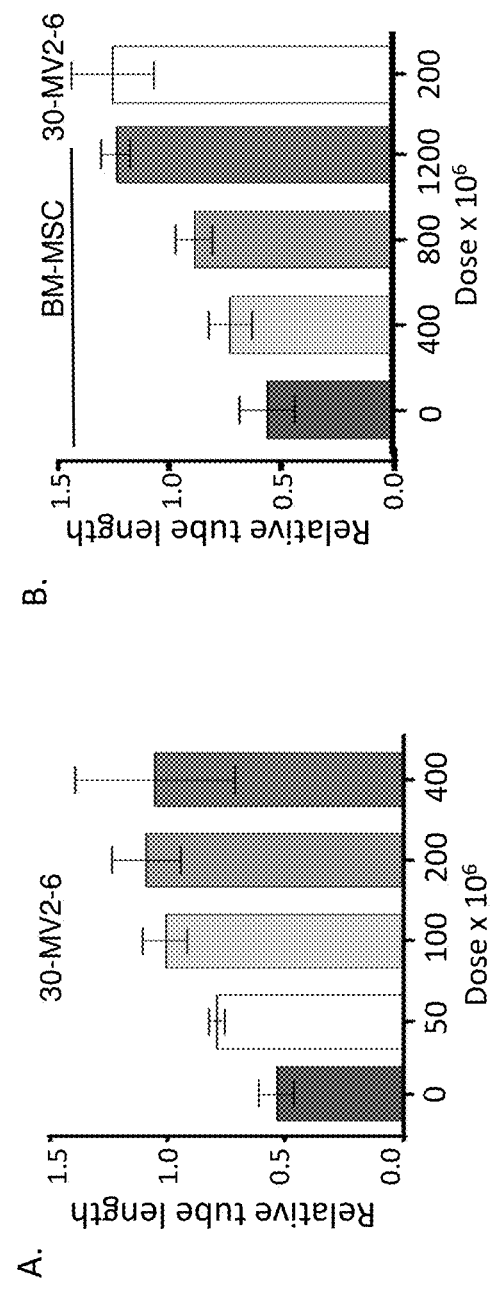
FIG. 5 shows that the angiogenic activity of exosomes isolated from the 30-MV2-6 cell line is dose dependent (panel A) and at least six times more potent than the angiogenic activity of exosomes isolated from BM-MSCs (panel B).

BM-MSC and 30-MV2-6 derived exosomes were further compared in a dose response experiment to determine differences in their potency. Exosomes were prepared and their concentration determined using nanoparticle tracking analysis (NTA; Nanosight, Malvern Instruments Ltd, Malvern, Worcestershire, UK). ELISA was used to confirm the presence of transpanins CD63, CD81 and CD9 that are typically expressed on exosomes. The 30-MV2-6 exosomes were tested at doses ranging from 50 million to 400 million exosomes per well. The BM-MSC exosomes were tested at doses ranging from 400 to 1200 million exosomes per well, because no significant activity was observed at 200 million exosomes per well. The results, shown in FIG. 5 indicate that the angiogenic response of HUVEC cells to 30-MV2-6 exosomes is dose responsive starting at 50 million per well and saturating at doses of >200 million exosomes per well (FIG. 5, panel A). In contrast, the BM-MSC exosomes showed a dose response of increasing angiogenic activity at doses from 400 million to 1200 million exosomes per well (FIG. 5, panel B). The potency of 30-MV2-6 derived exosomes was at least 6-fold greater than that of BM-MSC derived exosomes, having the equivalent activity at 200 million exosomes per well as BM-MSC derived exosomes at 1200 million exosomes per well (FIG. 5, panel B).

Example 4: Comparison of miRNA Content in Exosomes Derived from a Human Embryonic Progenitor Cell Line Versus Exosomes Derived from Adult BM-MSCs The miRNA content of the 30-MV2-6 derived exosomes was analyzed and compared to the miRNA content of the less angiogenic BM-MSC exosomes. RNA was extracted and purified from exosomes using the miRNeasy mini kit according to the manufacturer's recommended protocol (Qiagen, Hilden, Germany). The exosome RNA was quantified using a Nanodrop spectrophotometer and cDNA was prepared from the RNA using the miScript II RT kit (Qiagen, Hilden, Germany) according to the manufacturer's recommended protocol. The exosome cDNA was amplified by polymerase chain reaction (PCR) using the miScript pre-AMP PCR kit (Qiagen) and miScript pre-AMP pathway primer mix (human miFinder MBHS-001Z; Qiagen) according to the manufacturer's recommended protocol. Relative miRNA levels were assessed for 84 human miRNAs by quantitative PCR using the human miFinder miScript miRNA PCR array (#331221; Qiagen) according to the manufacturer's recommended protocol. The results were analyzed using the $\Delta\Delta CT$ method of relative quantitation available at (http://perdataanalysis.sabiosciences.com/mirna).

Figure 6A:
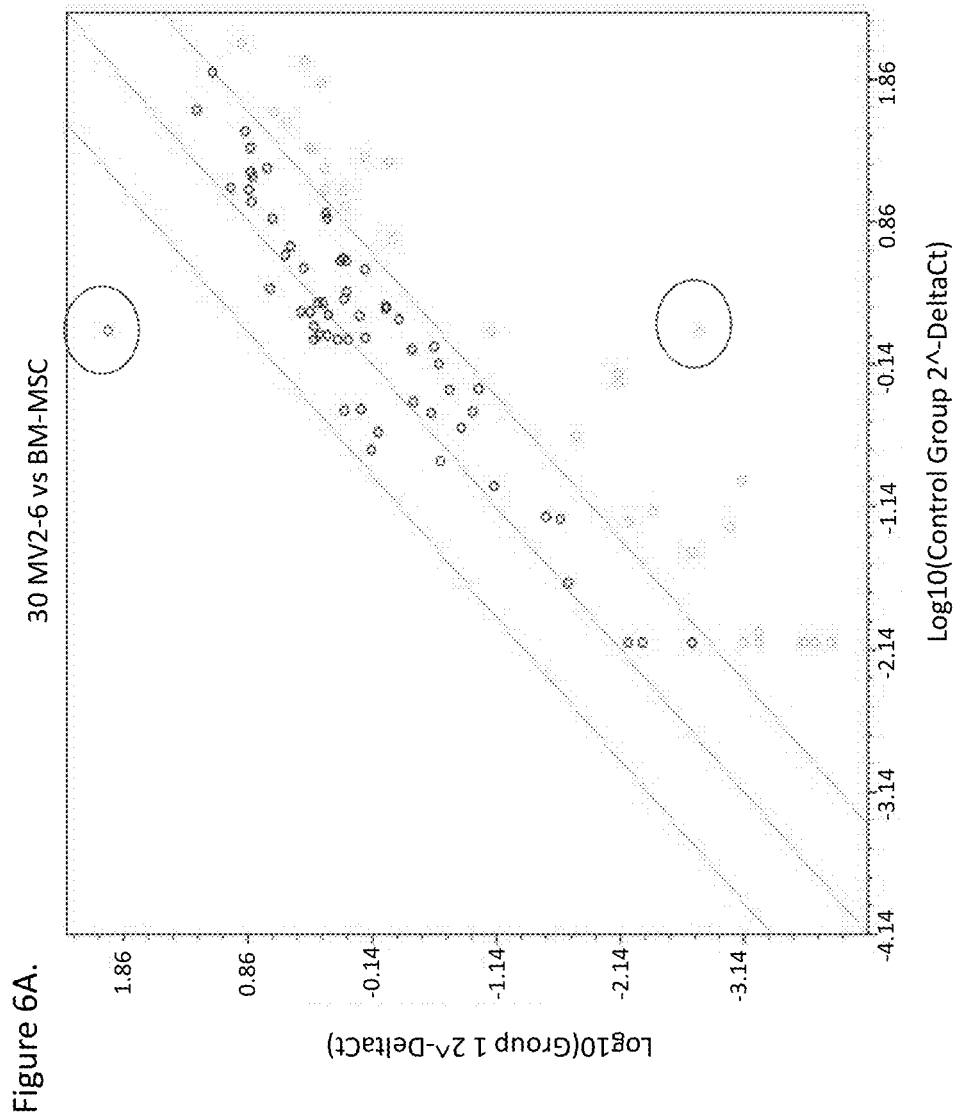
FIG. 6A depicts analysis of miRNA content in 30-MV2-6 derived exosomes versus BM-MSC derived exosomes. 30-MV2-6 exosome RNA was compared to BM-MSC RNA for miRNA content using an 84 miRNA PCR array. The scatter plot indicates miRNAs with greater than 6-fold differences. The upper circled dot represents miRNA miR-126-3p, which is expressed at 77.6-fold higher in 30-MV2-6 exosomes than in BM-MSC exosomes. The lower circled dot represents miRNA miR-376c-3p which is expressed at 752-fold lower in 30-MV2-6 exosomes than in MB-MSC exosomes.

There were substantial differences in the miRNA content of the 30-MV2-6 derived exosomes and BM-MSC derived exsomes. The miRNAs with greater than 6-fold difference between 30-MV2-6 exosomes and BM-MSC exosomes are shown in FIG. 6A scatter plot. Table 2 lists miRNAs that are more than 2-fold overexpressed in 30-MV2-6 exosomes relative to BM-MSC exosomes and Table 3 lists miRNAs that are more than 2-fold underexpressed in 30-MV2-6 exosomes relative to BM-MSC exosomes.

TABLE 2 miRNAs overexpressed in 30-MV2-6 exosomes compared to BM-MSC exosomes

| miRNA Mature ID | Fold Difference |
| --- | --- |
| hsa-miR-155-5p | 3.98 |
| hsa-miR-18a-5p | 2.54 |
| hsa-miR-374a-5p | 2.69 |
| hsa-miR-126-3p | 77.60 |

TABLE 3 miRNAs underexpressed in 30-MV2-6 exosomes compared to BM-MSC exosomes

| miRNA Mature ID | Fold Difference |
| --- | --- |
| hsa-miR-142-5p | −56.29 |
| hsa-miR-9-5p | −14.69 |
| hsa-miR-27b-3p | −6.92 |
| hsa-miR-101-3p | −4.82 |
| hsa-let-7d-5p | −3.12 |
| hsa-miR-16-5p | −10.56 |
| hsa-let-7g-5p | −7.60 |
| hsa-miR-30c-5p | −3.26 |
| hsa-miR-96-5p | −11.14 |
| hsa-miR-185-5p | −3.44 |
| hsa-miR-142-3p | −17.38 |
| hsa-miR-24-3p | −9.55 |
| hsa-miR-181b-5p | −2.03 |
| hsa-miR-302b-3p | −42.52 |
| hsa-miR-30b-5p | −3.34 |
| hsa-miR-21-5p | −16.16 |
| hsa-miR-15b-5p | −4.08 |
| hsa-miR-223-3p | −18.36 |
| hsa-miR-194-5p | −2.69 |
| hsa-miR-15a-5p | −4.25 |
| hsa-miR-125b-5p | −38.36 |
| hsa-miR-99a-5p | −10.43 |
| hsa-miR-29b-3p | −15.10 |
| hsa-miR-29a-3p | −35.08 |
| hsa-miR-141-3p | −4.30 |
| hsa-let-7a-5p | −4.03 |
| hsa-miR-124-3p | −13.56 |
| hsa-miR-92a-3p | −2.28 |
| hsa-miR-23a-3p | −5.74 |
| hsa-miR-25-3p | −3.16 |
| hsa-let-7e-5p | −2.35 |
| hsa-miR-376c-3p | −752.81 |
| hsa-miR-144-3p | −57.26 |
| hsa-miR-195-5p | −10.03 |
| hsa-miR-143-3p | −82.38 |
| hsa-miR-191-5p | −4.88 |
| hsa-let-7i-5p | −9.62 |
| hsa-miR-302a-3p | −17.39 |
| hsa-miR-222-3p | −2.31 |
| hsa-let-7b-5p | −35.56 |
| hsa-miR-186-5p | −3.40 |
| hsa-miR-196b-5p | −71.33 |
| hsa-miR-27a-3p | −3.42 |
| hsa-miR-22-3p | −4.58 |
| hsa-miR-130a-3p | −2.68 |
| hsa-let-7c-5p | −10.92 |

TABLE 3-continued miRNAs underexpressed in 30-MV2-6
exosomes compared to BM-MSC exosomes

| miRNA Mature ID | Fold Difference |
|---|---|
| hsa-miR-29c-3p | −24.99 |
| hsa-miR-140-3p | −2.98 |
| hsa-miR-128-3p | −2.77 |
| hsa-let-7f-5p | −2.89 |
| hsa-miR-122-5p | −9.20 |
| hsa-miR-100-5p | −10.00 |
| hsa-miR-302c-3p | −144.85 |

The miRNA with the highest relative expression in 30-MV2-6 exosomes compared to BM-MSC exosomes is miR-126-3p (77.6-fold difference, Table 2). MiR-126 is a known angiogenic miRNA ("angiomiR") that is endothelial cell-specific and has been shown to regulate both vascular integrity and developmental angiogenesis. Fish et al. (2008) Dev. Cell 15(2):272; Zou et al. (2011) Circ. Res. 108 (2):201; Jakob and Landmesser (2012) Cardiovasc. Res. 93(4):614; Nicoli et al. (2010) Nature 464(7292): 1196. Induction of miR-126 in endothelial cells and transport of miR-126 via exosomes has been shown to be important for the effective treatment of myocardial infarction (MI) using transplanted cardiosphere derived cells in a mouse model. Ong et al. (2014) Circulation 130 (11 Suppl 1):S60.

Accordingly, the clonal human embryonic progenitor cell line derived, miR-126-containing exosomes of the instant invention can be used in in vitro angiogenesis studies as well as in treatment of myocardial infarction and other ischemic conditions, either by themselves or in combination with transplanted cells.

RNA from 30-MV2-6 exosomes was also used to compare the miRNA content of angiogenic versus non-angiogenic exosomes. Exosomes derived from HT1080 cells (a human sarcoma cell line) are not angiogenic in the HUVEC in vitro angiogenesis assay at 2.0×10⁸ exosomes, a dose at which 30-MV2-6 exosomes show maximum angiogenic activity. HT1080 exosome RNA was analyzed on the miFinder miScript PCR array of 84 human miRNAs as described above and compared to 30-MV2-6 and BM-MSC exosome RNA (Table 4).

TABLE 4

Exosomal miRNAs in BM-MSC and 30-MV2-6
Relative to HT1080 exosomes

| miRNA Mature ID | BM-MSC/HT1080 Fold Difference | 30-MV2-6/HT1080 Fold Difference |
|---|---|---|
| hsa-miR-142-5p | 13.3253 | 0.2367 |
| hsa-miR-9-5p | 19.9437 | 1.3579 |
| hsa-miR-150-5p | 4.3783 | 3.3457 |
| hsa-miR-27b-3p | 100.911 | 14.5862 |
| hsa-miR-101-3p | 14.0298 | 2.9096 |
| hsa-let-7d-5p | 26.3588 | 8.441 |
| hsa-miR-103a-3p | 4.5649 | 5.7031 |
| hsa-miR-16-5p | 38.0552 | 3.605 |
| hsa-miR-26a-5p | 41.3044 | 24.3186 |
| hsa-miR-32-5p | 15.9192 | 14.3894 |
| hsa-miR-26b-5p | 52.2677 | 31.9112 |
| hsa-let-7g-5p | 76.0374 | 10.0027 |
| hsa-miR-30c-5p | 17.5335 | 5.3714 |
| hsa-miR-96-5p | 1.1148 | 0.1 |
| hsa-miR-185-5p | 29.375 | 8.5466 |
| hsa-miR-142-3p | 0.5468 | 0.0315 |
| hsa-miR-24-3p | 40.061 | 4.1927 |
| hsa-miR-155-5p | 1.0346 | 4.118 |
| hsa-miR-146a-5p | 1.4501 | 1.0803 |
| hsa-miR-425-5p | 3.3003 | 2.8192 |
| hsa-miR-181b-5p | 16.2276 | 8.0058 |
| hsa-miR-302b-3p | 45.0196 | 1.0589 |
| hsa-miR-30b-5p | 19.9194 | 5.9589 |
| hsa-miR-21-5p | 52.4899 | 3.2475 |
| hsa-miR-30e-5p | 4.4078 | 3.3143 |
| hsa-miR-200c-3p | 2.2547 | 1.3309 |
| hsa-miR-15b-5p | 22.3822 | 5.4881 |
| hsa-miR-223-3p | 202.2804 | 11.0146 |
| hsa-miR-194-5p | 8.5348 | 3.1718 |
| hsa-miR-210-3p | 1.8074 | 0.957 |
| hsa-miR-15a-5p | 17.2702 | 4.0614 |
| hsa-miR-181a-5p | 28.6581 | 16.7792 |
| hsa-miR-125b-5p | 31.2942 | 0.8158 |
| hsa-miR-99a-5p | 13.0061 | 1.2466 |
| hsa-miR-28-5p | 11.1092 | 8.1182 |
| hsa-miR-320a | 17.2154 | 13.7088 |
| hsa-miR-125a-5p | 13.0238 | 8.8833 |
| hsa-miR-29b-3p | 9.9121 | 0.6563 |
| hsa-miR-29a-3p | 51.1831 | 1.4592 |
| hsa-miR-141-3p | 7.9244 | 1.841 |
| hsa-miR-19a-3p | 4.5159 | 3.3341 |
| hsa-miR-18a-5p | 7.7906 | 19.7947 |
| hsa-miR-374a-5p | 45.91 | 123.3183 |
| hsa-miR-423-5p | 20.4698 | 18.6725 |
| hsa-let-7a-5p | 25.3493 | 6.294 |
| hsa-miR-124-3p | 20.2226 | 1.4916 |
| hsa-miR-92a-3p | 14.4072 | 6.3169 |
| hsa-miR-23a-3p | 52.5584 | 9.1492 |
| hsa-miR-25-3p | 23.7331 | 7.5106 |
| hsa-let-7e-5p | 22.9181 | 9.7439 |
| hsa-miR-376c-3p | 2411.7739 | 3.2037 |
| hsa-miR-126-3p | 123.9456 | 9618.223 |
| hsa-miR-144-3p | 114.87 | 2.0061 |
| hsa-miR-424-5p | 57.34 | 92.8881 |
| hsa-miR-30a-5p | 3.966 | 3.4279 |
| hsa-miR-23b-3p | 19.0703 | 13.0079 |
| hsa-miR-151a-5p | 12.8604 | 25.4071 |
| hsa-miR-195-5p | 40.2617 | 4.0149 |
| hsa-miR-143-3p | 273.1733 | 3.316 |
| hsa-miR-30d-5p | 3.9436 | 4.0508 |
| hsa-miR-191-5p | 21.2256 | 4.3493 |
| hsa-let-7i-5p | 62.9552 | 6.545 |
| hsa-miR-302a-3p | 37.209 | 2.14 |
| hsa-miR-222-3p | 22.8182 | 9.8699 |
| hsa-let-7b-5p | 129.1842 | 3.6327 |
| hsa-miR-19b-3p | 5.758 | 3.3451 |
| hsa-miR-17-5p | 4.6186 | 7.3351 |
| hsa-miR-93-5p | 16.2937 | 16.7172 |
| hsa-miR-186-5p | 14.8015 | 4.3526 |
| hsa-miR-196b-5p | 15.3129 | 0.2147 |
| hsa-miR-27a-3p | 48.4243 | 14.148 |
| hsa-miR-22-3p | 13.8229 | 3.0157 |
| hsa-miR-130a-3p | 11.5632 | 4.3074 |
| hsa-let-7c-5p | 93.5201 | 8.5615 |
| hsa-miR-29c-3p | 39.8245 | 1.5935 |
| hsa-miR-140-3p | 9.8899 | 3.3169 |
| hsa-miR-128-3p | 21.7273 | 7.8472 |
| hsa-let-7f-5p | 30.5392 | 10.5782 |
| hsa-miR-122-5p | 71.7561 | 7.8014 |
| hsa-miR-20a-5p | 4.6119 | 9.1362 |
| hsa-miR-106b-5p | 5.093 | 8.4218 |
| hsa-miR-7-5p | 4.8173 | 6.4945 |
| hsa-miR-100-5p | 14.7509 | 1.4748 |
| hsa-miR-302c-3p | 120.5214 | 0.832 |

Figure 6B:
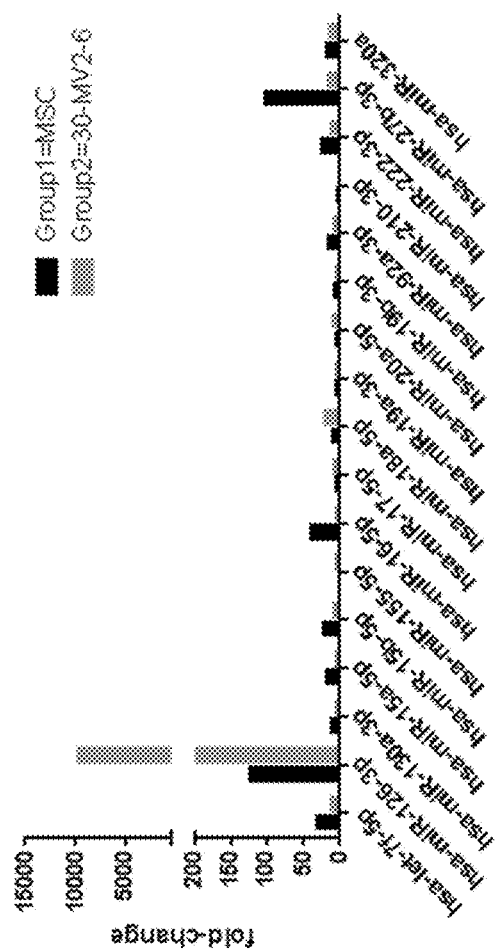
FIG. 6B is a bar graph illustrating the differences (measured as fold-change) in miRNA expression profile between 30-MV2-6-derived exosomes versus BM-MSC-derived exosomes.

The data in Table 4 and FIG. 6B illustrate the dramatic differences in the miRNA content of the three types of exosomes. These data show that HT1080 exosomes contain the lowest amount of miRNA for all miRNAs tested, except for miR-96-5p and miR-142-3p, which are lowest in 30-MV2-6 exosomes. The miRNA miR-142-3p is expressed at highest levels in HT1080 exosomes and is known to repress several inhibitors of oncogenic transformation. It is mimicked by Kaposi sarcoma viral miRNA, miR-K10a. Forte et al. (2015) *J Virol* 89(4): 2333. The miR-96-5p miRNA is present in highest levels in BM-MSC exosomes and is higher in HT1080 exosomes than 30-MV2-6 exosomes. This miRNA is thought to be involved in osteogenic and adipogenic differentiation in BM-MSCs (Laine et al. (2012) *J Cell Biochem.* 113(8):2687) but is also involved in tumor cell proliferation (Lin et al. (2010) *Plos One* 5(12): e15797; Haflidadottir et al. (2013) *Plos One* 8(8):e72400). Strikingly the miRNA with the highest levels in 30-MV2-6 exosomes relative to HT1080 exosomes is miR-126-3p. This known angiogenic miRNA is present at a 9618-fold higher level in 30-MV2-6 exosomes than HT1080 exosomes. MiR-155 is 4-fold higher in 30-MV2-6 exosomes than BM-MSC or HT1080 exosomes and is anti-angiogenic but pro-arteriogenic. Pankrtaz et al. (2015) *Circulation* 131(18):1575. Of the 9 remaining miRNAs that are highest in 30-MV2-6 exosomes, 6 are known to be involved in angiogenesis. The miRNAs miR-18a-5p, miR-20a-5p, miR-424-5p, miR-17-5p, and miR-7-5p miRNAs have anti-angiogenic activity. However, none of these anti-angiogenic miRNAs are more than 2.5-fold enriched in 30-MV2-6 exosomes compared to BM-MSC exosomes. The pro-angiogenic miR-106b is 9-fold enriched in 30-MV2-6 but only 4-fold enriched in BM-MSC exosomes compared to HT1080 exosomes. It is needed for neovascularization after hind limb ischemia. Semo et al. (2014) *Eur Heart J.* 35(45):3212.

Notably, several anti-angiogenic miRNAs, including miR-143-3p (Climent et al. (2015) *Circ Res.* 116(11):1753), miR-223-3p (Dai et al. (2014) *Plos One* 9(10):e108468), miR-222-3p (Suarez and Sessa (2009) *Circ Res.* 104(4): 442), miR-15a, miR-15b and miR-16 (Spinetti et al. (2013) *Circ Res.* 112(2):335; Liu et al. (2012) *Cell Physiol Biochem.* 29(5-6):851)) were enriched for and/or present at highest level in the BM-MSC-derived exosomes.

Example 5: Comparison of Angiogenic Activity of Exosomes Derived from Various Clonal Embryonic Stem Cell Lines and Exosomes Derived from the Parental Pluripotent Stem Cell Lines Clonal embryonic progenitor cell lines were previously established from human pluripotent stem (hPS) cell lines using methods previously described. West et al. (2008) *Regen Med.* 3(3):287. The resulting cell lines are not immortalized but have higher replicative potential than primary cell lines because of their long telomere length that is near that of the parental hPS cell line from which they are derived. A wide diversity of cell types was produced by exposing hPS cells to an array of cell culture medium, cell matrix, and growth conditions followed by selective pressure for clonal growth and scalability. Over 140 such cell types have been determined to be distinct by analysis of total transcribed RNA using standard Illumina microarrays. The in vitro angiogenesis assay (described in detail in Example 2) was used to screen clonal embryonic progenitor cells for production of angiogenic exosomes. As shown in Table 5, most embryonic endothelial progenitor cell-derived exosomes have angiogenic activity in the range of 30-MV2-6 derived exosomes (+; relative tube length (RTL) >0.75 and <1.25). The 30-MV2-9 exosomes scored highest (++; RTL >1.25). Two endothelial progenitor lines scored negative (-; RTL <0.75). Exosomes from an osteochondral line, primary fibroblasts (BJ), BM-MSCs, and a human sarcoma cell line (HT1080) were also negative. The two clonal smooth muscle cell progenitor cell lines and one clonal pericyte line tested were positive in the in vitro vascular tube formation assay. Exosomes prepared from conditioned medium of the parental human embryonic stem cell lines H9 (WA09) and ESI-017 were also positive in the in vitro vascular tube formation assay.

TABLE 5

TABLE 5: Angiogenic activity of PureStem vascular progenitors and other cell lines.

| Cell Line | Source | Cell Type | Relative tube length | Angiogenic Index |
|---|---|---|---|---|
| 30-MV2-9 | PureStem | Endothelial | 1.67 | ++ |
| 30-MV2-6 | PureStem | Endothelial | 1.07 | + |
| 30-MV2-7 | PureStem | Endothelial | 0.94 | + |
| 30-MV2-17 | PureStem | Endothelial | 0.76 | + |
| 30-MV2-19 | PureStem | Endothelial | 0.84 | + |
| RP1-MV2-8 | PureStem | Endothelial | 1.07 | + |
| 30-MV2-14 | PureStem | Endothelial | 1.00 | + |
| 30-MV2-15 | PureStem | Endothelial | 1.00 | + |
| RP1-MV2-8 | PureStem | Endothelial | 1.07 | + |
| 30-MV2-24 | PureStem | Endothelial | 0.41 | - |
| 30-MV2-4 | PureStem | Endothelial | 0.72 | - |
| W10 | PureStem | Smooth Muscle | 0.83 | + |
| Z11 | PureStem | Smooth Muscle | 0.92 | + |
| E164 | PureStem | Pericyte | 0.86 | + |
| PC-M | hES | Pericyte | 0.47 | - |
| BJ | Primary | Foreskin Fibroblast | 0.61 | - |
| SM30 | PureStem | MSC-like | 0.71 | - |
| MSCs | Primary | Adult BM-MSC | 0.68 | - |
| HT1080 | Transformed | Sarcoma | 0.71 | - |
| H9 | Embryonic | Pluripotent | 1.06 | + |
| ESI-017 | Embryonic | Pluripotent | 1.27 | + |

Example 6: In Vivo Angiogenic Activity of Embryonic Progenitor Stem Cell Derived Exosomes Angiogenic activity of exosomes was assessed in vivo using the Matrigel plug assay in mice as previously described. Sahoo et al. (2011) *Circ Res.* 109(7):724. Immunocompromised mice (Female Nu/J mice aged 6-8 weeks; 2 plugs/mouse; 2 mice/group) were injected subcutaneously with approximately 300 µl of Matrigel containing PBS, $4\times10^8$/ml exosomes, or 150 ng/ml bFGF plus 60 ng/ml VEGF (positive control). The plugs were removed at day 14 after implant followed by fixation and paraffin embedding. The sections were stained with hematoxylin and Eosin (H&E) for histological examination and stained with von Willabrand factor antibody for detection of endothelial cells.

Figure 7:
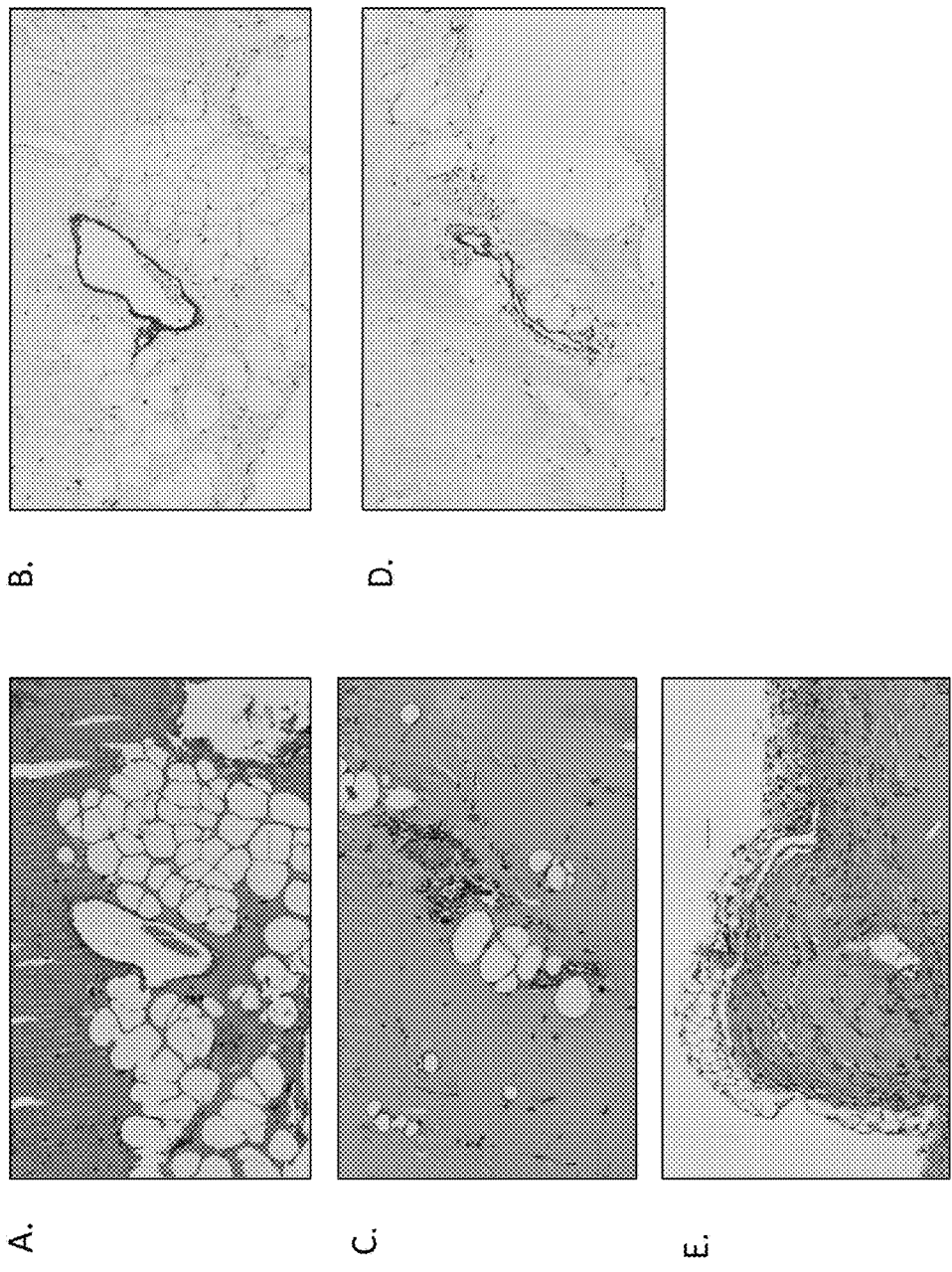
FIG. 7 consists of 5 photomicrographs showing in vivo angiogenic activity of human clonal endothelial cell line 30-MV2-6 in the Matrigel plug assay in immunocompromised mice. Blood vessel-like structures are seen in the exosome treated plugs (panels A and C) but not in the control plug (panel E). Endothelial cell content is confirmed by staining with anti-Von Willebrand factor antibody (panels B and D).

The data indicate that 30-MV2-6 exosomes are angiogenic in the Matrigel plug assay (FIG. 7). The exosome containing plugs show regions of infiltration of cells into the plug with vessel formation (FIG. 7, panels A and C). The positive control plugs containing growth factors have regions of vessel formation (not shown) Immunostaining with antibody against von Willabrand factor (FIG. 7, panels B and D) confirmed the endothelial identity of cells lining the vessel structures observed by H&E staining. The PBS control plugs show less cell infiltration and no vessel formation (FIG. 7, panel E).

Example 7: Scale-Up of Clonal Embryonic Progenitor Stem Cells for Exosome Production Clonal embryonic progenitor cell lines described here are advantageous over other sources of biologically active exosomes because of their scalability. The parental pluripotent stem cell line to 30-MV2-6 which also produces angiogenic exosomes is costly to scale up because of the requirements for specialized medium and cell matrix (e.g. Matrigel). Primary endothelial stem cells or mesenchymal stromal cells rapidly lose differentiation and proliferative capacity upon culture in vitro. Typically MSCs begin to senesce in culture after 7-12 passages (approximately 10 population doublings) and show multiple changes including altered surface marker expression and increased autofluorescence. Wagner et al. (2008) *Plos One* 3(5):e2213. In contrast, human embryonic clonal progenitor lines such as the cell lines of the instant invention are grown under standard tissue culture conditions and medium and are highly scalable with typical replicative lifespans of 60 to 100 population doublings.

The Terumo Quantum Cell Expansion system (the bioreactor used in the instant example) is an automated hollow fiber cell culture platform designed for GMP compatible production of cells for use in cell therapy. The bioreactor was seeded at a density of approximately 900 cells/cm$^2$ with approximately $4.0 \times 10^7$ 30-MV2-6 cells (passage 9) and the cells were cultured for 13 days under their standard growth conditions of EGM-MV2 medium and 5% oxygen. The exosomes were collected by exchanging the complete medium for conditioning medium (basal EGM-MV2 medium without serum added; alternatively PBS may be also used). The conditioning medium was left in the bioreactor for 16 hours and collected for exosome purification. The cells were harvested by exchanging medium with a 0.25% trypsin solution to remove cells for the reactor, tested for viability and counted. Cells were scaled over 10-fold from the initial 40 million to approximately 440 million. The purified exosomes were quantified using CD63 detection ELISA (alternatively, nanoparticle tracking analysis as described in Example 1 may be used to quantify the exosomes). The yield of exosomes from one bioreactor run is at least $2.3 \times 10^{10}$, which is equivalent to the approximate exosome yield from 72 T-225 flasks of 30-MV2-6 cells.

Figure 8:
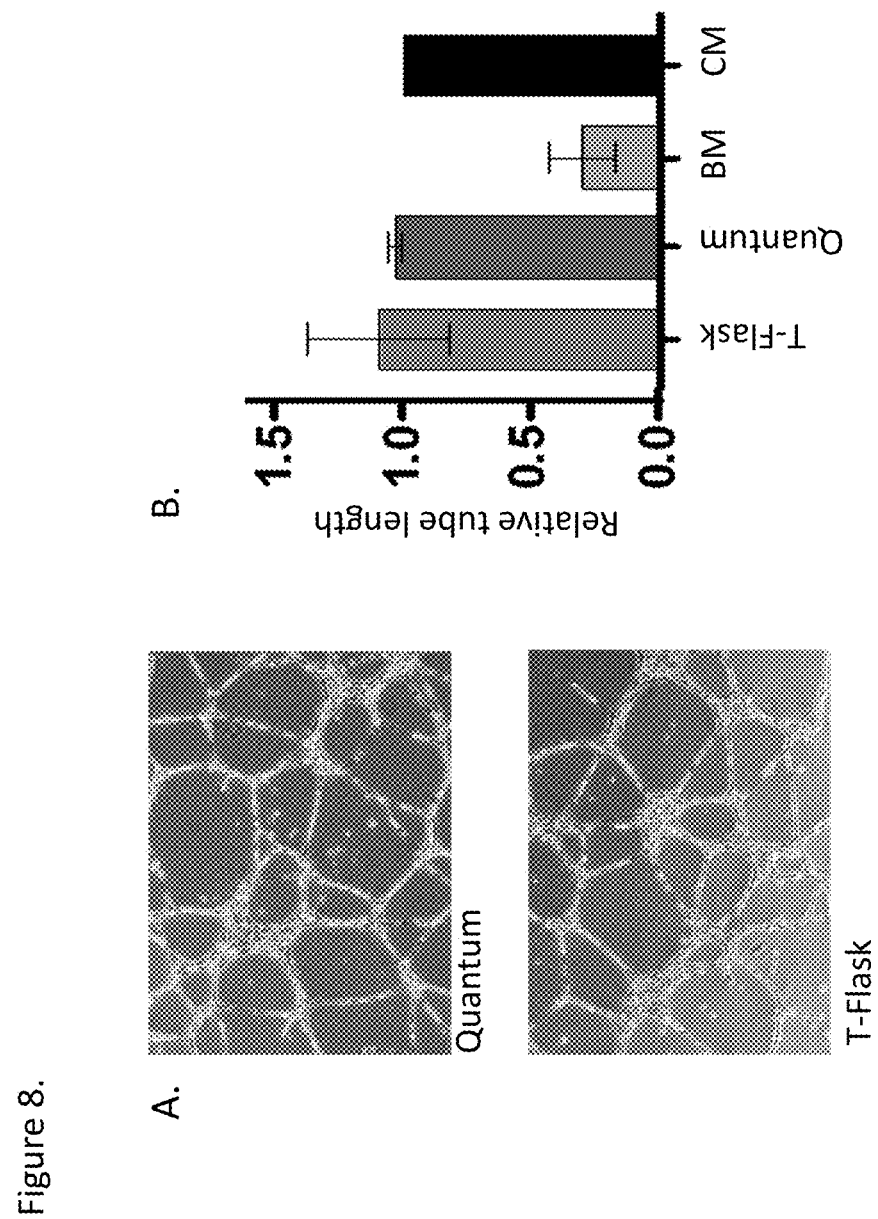
FIG. 8 shows that the in vitro angiogenic activity of exosomes derived from 30-MV2-6 cells grown in T-flasks is comparable to the in vitro angiogenic activity of exosomes derived from 30-MV2-6 cells grown in the Quantum cell expansion bioreactor. Panel A depicts tube network formation and panel B depicts quantitative analysis of tube length using Image J angiogenesis analyzer software. BM: basal medium, negative control; CM: complete growth medium.

The purified exosomes were tested for angiogenic activity at a dose of $2.0 \times 10^6$ exosomes per well in the in vitro tube formation assay (described in detail in Example 2). As shown in FIG. 8, the angiogenic activity of exosomes prepared from media conditioned by 30-MV2-6 cells grown in T-flasks was equivalent to the angiogenic activity of exosomes prepared from medium conditioned by 30-MV2-6 cells grown in the Quantum Cell Expansion system.

Example 8: Effect of Oxygen Concentration and Conditioning Medium on Exosome Activity Hypoxia has been reported to increase exosome production from mammalian cells (Tadokoro et al. (2013) *J Biol Chem.* 288(48):34343; King et al. (2012) *BMC Cancer* 12:241). Furthermore, clonal embryonic progenitor cell lines are derived and maintained under low oxygen (5%). West et al. (2008) *Regen Med.* 3(3): 287. Therefore, 1% oxygen was tested for exosome production to determine if increasing hypoxia will increase exosome production or angiogenic activity.

Other stress conditions can also have an effect on exosome yield or activity. Serum starvation is used to induce exosome production. Nutrient deprivation was tested by using PBS as the conditioning medium. The use of PBS versus basal EGM-MV2 medium for conditioning the cells was also tested.

Figure 9:
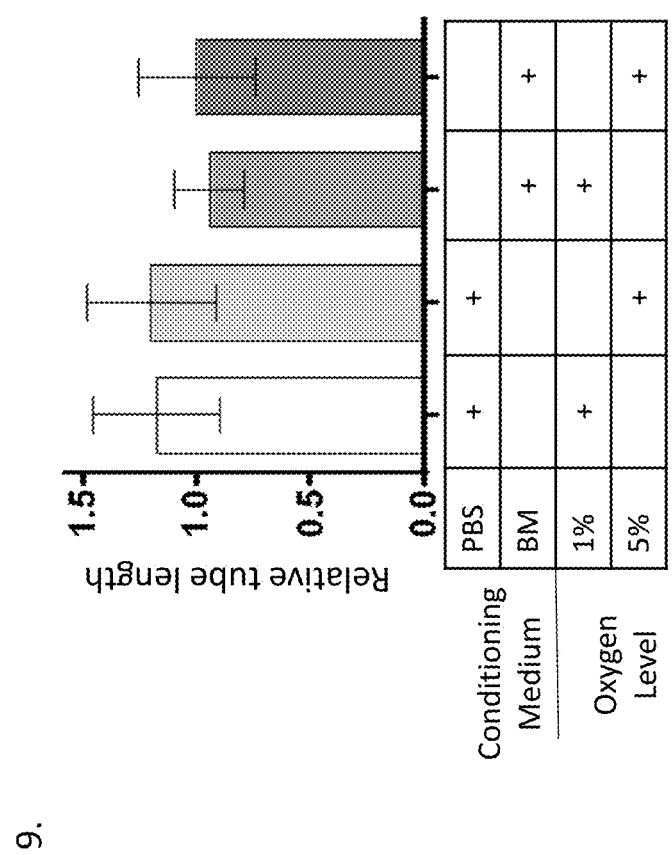
FIG. 9 is a bar graph illustrating the effect of oxygen level and conditioning medium used on the angiogenic activity of exosomes derived from 30-MV2-6 cells. Use of PBS versus basal medium as the conditioning medium had no significant effect on the angiogenic activity of the 30-MV2-6 exosomes. Similarly, no significant effect on the angiogenic activity was observed in conditioning the cells in 1% versus 5% oxygen.

The results shown in FIG. 9 indicate that there is no significant difference in angiogenic activity of isolated exosomes when the medium was conditioned by cells incubated in 1% or 5% oxygen. These data also indicate the exosome angiogenic activity is not significantly different when PBS is used as the conditioning media compared to when the basal medium is used as the conditioning medium, although there is a trend toward higher activity when PBS is used.

Example 9: Quantitation of Exosome Concentration by ELISA Detection of CD63 on Intact Exosomes There is a need for simple and convenient method to measure the concentration of exosome particles in a purified preparation of exosomes. Currently available ELISA kits for measuring exosome concentration (System Biosciences, Inc., Mountain View, Calif.) require lysing exosomes and have a lower limit of detection of approximately $2.0 \times 10^8$ exosomes. It is advantageous to measure low concentration samples directly without diluting the sample in a lysis buffer. Moreover, lysing the exosomes releases other proteins and nucleic acids that potentially interfere with the assay. The method described herein takes advantage of markers commonly presented on the surface of exosomes, such as transpanins CD63, CD9 and CD81 and allows for quantitation of intact exosomes.

A standard curve is prepared from exosome samples of known concentration (ranging from $5 \times 10^8$ to $8 \times 10^7$ exosomes/mL). The unknown samples are prepared in PBS or a buffer exchanged into PBS. Samples of intact exosomes are bound to 96 well ELISA plate wells in PBS at 50 µl/well for at least 16 hours at 37° C. The wells are washed 3×5 minutes in wash buffer (e.g. TBS-Tween). The wells are incubated with a mouse monoclonal antibody prepared in a suitable blocking buffer (e.g. PBS containing exosome depleted FBS and 0.05% Tween 20) that recognizes the extracellular domain of CD63 on intact exosomes for 1 hour at room temperature. The wells are washed again 3×5 minutes at room temperature. The wells are incubated with a suitable secondary antibody in a blocking buffer for detection of mouse anti-CD63 antibody bound to exosomes on the plate surface (e.g. HRP conjugated goat anti-mouse IgG) for 1 hour at room temperature. The wells are washed again 3×5 minutes at room temperature and the wells incubated with 50 µl of HRP substrate (e.g. Supersensitive TMB ELISA substrate) for 30 minutes at room temperature. The wells are washed 3×5 minutes at room temperature and 50 µl of stop buffer (0.16M sulfuric acid) is added to provide a fixed endpoint. The concentration of exosomes is quantitated by measuring the absorbance of each well at 450 nm.

Figure 10:
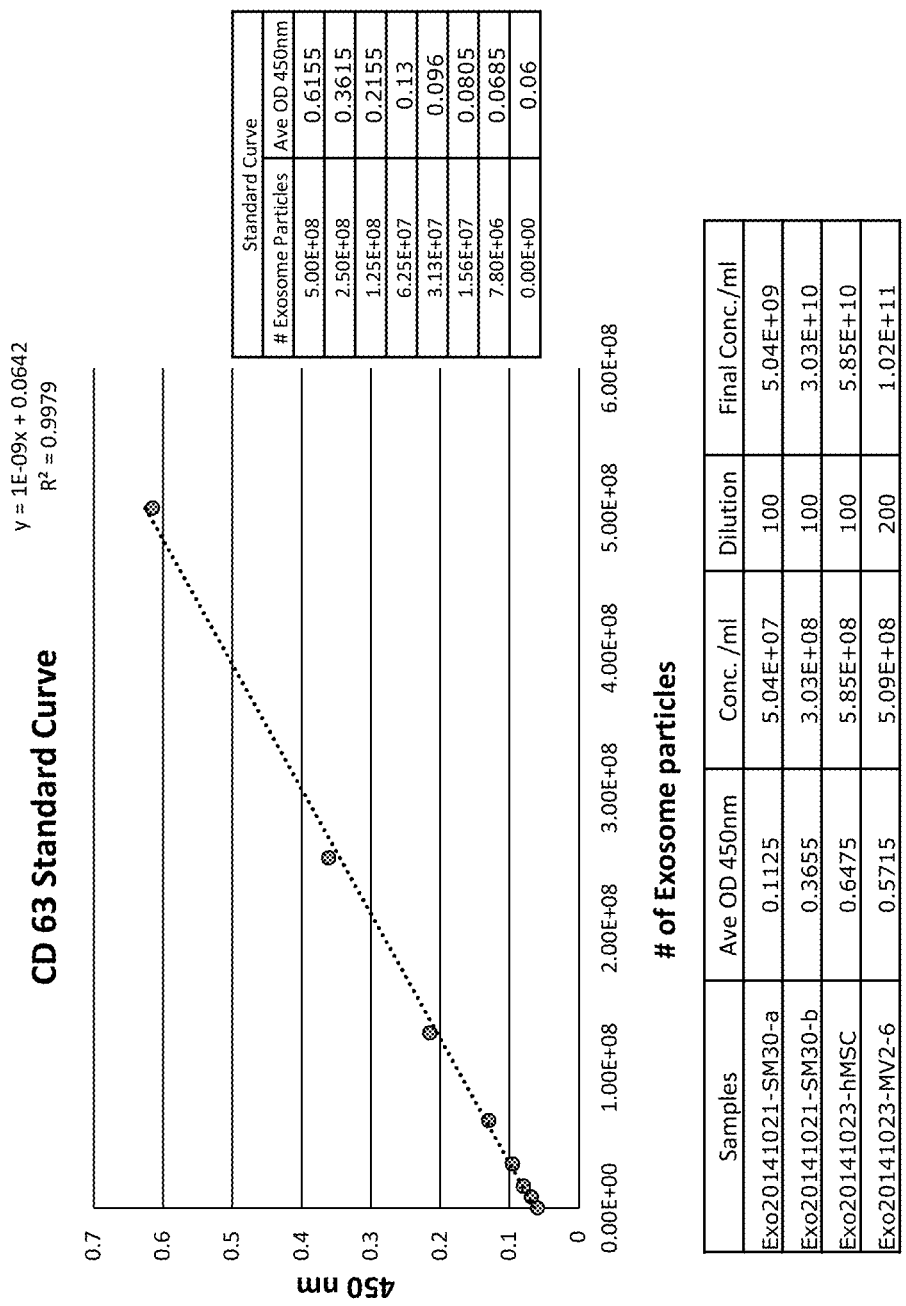
FIG. 10 shows ELISA detection of CD63 on intact exosomes to determine exosome concentration. The standard curve was prepared using exosomes (from HT1080 cells) of known concentration as determined by nanoparticle analysis (NTA). Quantitation of exosomes in samples of unknown concentration was calculated from OD value at 450 nm. The assay assumes CD63 content of exosomes derived from various different cells remains relatively constant.
Figure 11:
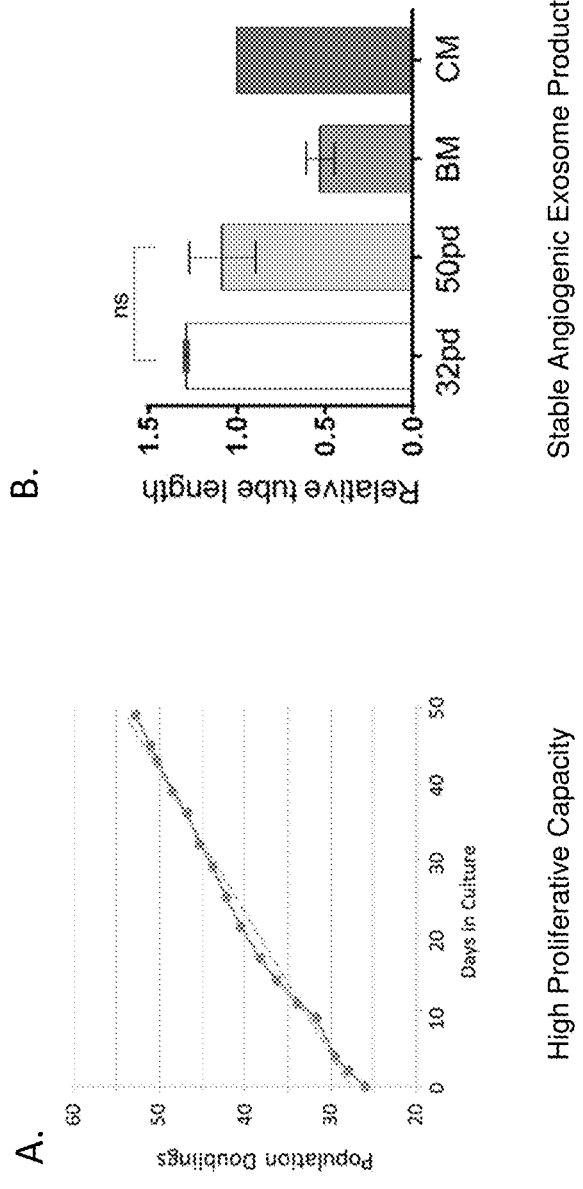
FIG. 11 depicts the high proliferative capacity and stable angiogenic exosome production of the clonal human embryonic progenitor cell line 30-MV2-6. The 30-MV2-6 cells continue to proliferate in cell culture past 50 population doublings (panel A). Similarly, exosomes that retain their angiogenic activity as measured by the in vitro tube formation assay may be prepared from 30-MV2-6 cells that have been cultured for at least 50 population doublings (panel B).
Figure 12:
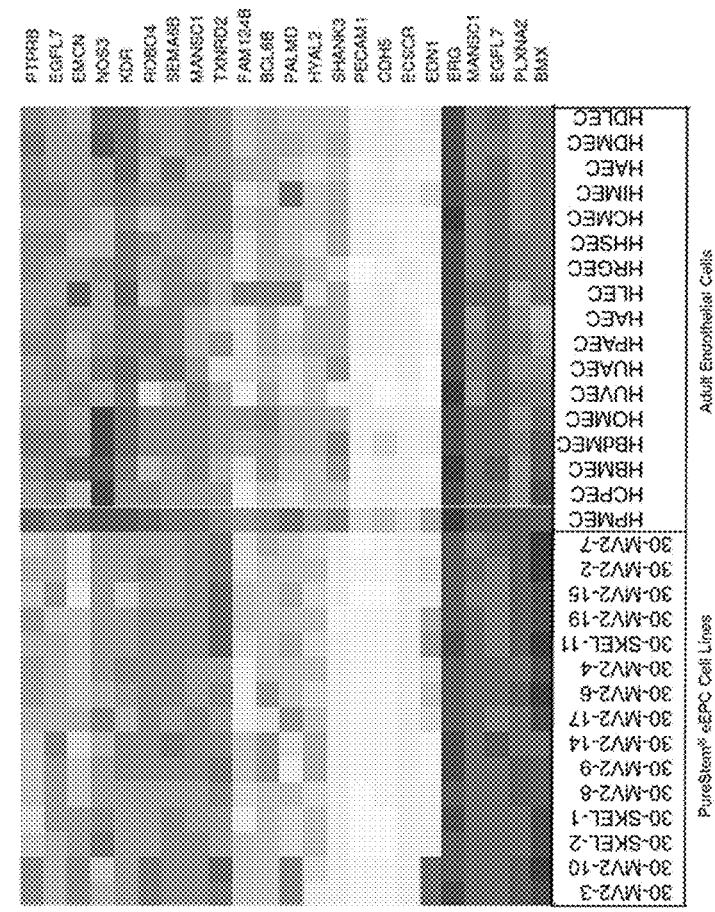
FIG. 12 is a heat map of Illumina gene expression array (Illumina, Hayward, Calif.) data showing that the clonal embryonic epithelial progenitor cell lines derived from the embryonic stem cell line ESI-017 have similar endothelial specific gene expression pattern as various adult endothelial cells from different sources.

An example of a standard curve and quantitation of samples is shown in FIG. 10.

What is claimed is:

1. An exosome isolated from an expanded clonal progenitor cell line, wherein said expanded clonal progenitor cell line is positive for the expression of PCDHB2.

2. The exosome of claim 1, wherein the clonal progenitor cell line is a human clonal progenitor cell line.

3. The exosome of claim 1, wherein the clonal progenitor cell line is an endothelial progenitor cell line.

4. The exosome of claim 1, wherein the exosome contains CD63.

5. The exosome of claim 1, wherein the exosome contains one or more angiogenic miRNAs.

6. The exosome of claim 1, wherein the exosome contains miR-126.

7. The exosome of claim 1, wherein the clonal progenitor cell line expresses CD31 and CD34.

8. The exosome of claim 1, wherein the clonal progenitor cell line expresses one or more genes listed in Table 1.

9. An exosome isolated from an expanded clonal progenitor cell line, wherein said expanded clonal progenitor cell line is positive for the expression of PCDHB2, and wherein the clonal progenitor cell line is 30-MV2-6.

10. The exosome of claim 1, wherein the exosome enhances the formation of vascular tube-like formations when contacted with an endothelial cell.

11. The exosome of claim 1 further comprising a pharmaceutical carrier.

12. A purified preparation of clonal progenitor cell line exosomes comprising the exosome of claim 1, and wherein the exosomes comprise an elevated level of miRNA miR-126 relative to that in adult bone marrow-derived mesenchymal stem cell exosomes.

13. The purified preparation of claim 12, wherein the exosomes further comprise a lower level of miRNA miR-376c-3p relative to that in adult bone marrow-derived mesenchymal stem cell exosomes.

14. The exosome preparation of claim 12, wherein the levels of miR-126 and miR-376c-3p in the clonal progenitor cell line exosomes differ from those in the adult bone marrow-derived mesenchymal stem cell exosomes by greater than six-fold.

15. The exosome preparation of claim 12, wherein the exosomes further comprise an elevated level of one or more of miR-155-5p, miR-18a-5p, and miR-374a-5p relative to those in adult bone marrow-derived mesenchymal stem cell exosomes.

16. The exosome preparation of claim 12, wherein the exosomes further comprise a lower level of one or more of miR-142-5p, miR-9-5p, miR-27b-3p, miR-101-3p and let-7d-5p relative to those in adult bone marrow-derived mesenchymal stem cell exosomes.

17. The exosome preparation of claim 12, which induces dose dependent angiogenic activity in human umbilical cord vascular endothelial cells.

18. The exosome preparation of claim 12, which induces angiogenic activity in human embryonic stem cell derived perivascular embryonic progenitor cells.

19. The exosome preparation of claim 18, wherein the angiogenic activity is dose dependent.

20. A purified preparation of clonal progenitor cell line exosomes comprising the exosome of claim 9.

* * * * *